US 6,677,498 B2

(12) United States Patent
Chen et al.

(10) Patent No.: US 6,677,498 B2
(45) Date of Patent: *Jan. 13, 2004

(54) CENTER-FILL ABSORBENT ARTICLE WITH A WICKING BARRIER AND CENTRAL RISING MEMBER

(75) Inventors: Fung-jou Chen, Appleton, WI (US); Jeffrey Dean Lindsay, Appleton, WI (US); Joseph DiPalma, Neenah, WI (US); Julie Marie Bednarz, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 10/290,905

(22) Filed: Nov. 8, 2002

(65) Prior Publication Data

US 2003/0097105 A1 May 22, 2003

Related U.S. Application Data

(63) Continuation of application No. 09/411,259, filed on Oct. 1, 1999, now Pat. No. 6,492,547.

(51) Int. Cl.⁷ .............................. A61F 13/15; A61F 13/20
(52) U.S. Cl. .................................. 604/378; 604/385.01
(58) Field of Search ..................... 604/385.01, 385.101, 604/385.12, 378, 385.17

(56) References Cited

U.S. PATENT DOCUMENTS

| | | | |
|---|---|---|---|
| 2,064,431 A | 12/1936 | Jurgensen | |
| 2,683,457 A | 7/1954 | Cunningham | |
| 2,747,575 A | 5/1956 | Mercer | |
| 3,126,888 A | 3/1964 | Woldman | |
| 3,156,242 A | 11/1964 | Crowe, Jr. | |
| 3,294,091 A | 12/1966 | Morse | |

(List continued on next page.)

FOREIGN PATENT DOCUMENTS

| | | |
|---|---|---|
| AU | 699325 | 12/1998 |
| CA | 884608 | 11/1971 |
| DE | 196 40 451 A1 | 4/1998 |
| EP | 0136524 A1 | 4/1985 |
| EP | 0360285 A2 | 3/1990 |
| EP | 0 400 895 A1 | 12/1990 |

(List continued on next page.)

OTHER PUBLICATIONS

Kim, S.H. et al., "Synthesis and Characterization of Dextran–Based Hydrogel Prepared By Photocrosslinking," Carbohydrate Polymers, vol. 40, No. 3, Sep. 1999, pp. 183–190.

Krema, Radko et al., "What's New In Highloft Production?" Nonwovens Industry, Oct. 1997, pp. 74–78.

Lee, Seungsin et al., "Antimicrobial and Blood Repellent Finishes for Cotton and Nonwoven Fabrics Based on Chitosan and Fluoropolymers," Textile Research Journal, 69(2), Feb. 1999, pp. 104–112.

Rahn, K. et al., "New Cellulosic Polymers By Subsequent Modification of 2,3–Dialdehyde Cellulose," Cellulose Chemistry and Technology, 32, 1998, pp. 173–183.

Primary Examiner—Weilun Lo
Assistant Examiner—Michele Kidwell
(74) Attorney, Agent, or Firm—Pauley Petersen Kinne & Erickson

(57) ABSTRACT

An absorbent article is disclosed comprising a central absorbent member, an outer absorbent member, and a central rising member for urging the central absorbent member toward the body of the user when compressed laterally inward by the legs of the user. The article is able to achieve good center-fill performance when in use and maintain excellent body fit. Also disclosed is a lateral wicking barrier for inhibition of wicking from the central regions of the article to an outlying outer absorbent member. The combination of a wicking barrier isolating the central absorbent member from the longitudinal sides of the article and a central rising member urging the central absorbent member toward the body yields an article with excellent absorbency and leakage protection.

25 Claims, 23 Drawing Sheets

U.S. PATENT DOCUMENTS

| | | |
|---|---|---|
| 3,575,174 A | 4/1971 | Mogor |
| 3,667,466 A | 6/1972 | Ralph |
| 3,860,003 A | 1/1975 | Buell |
| 3,881,489 A | 5/1975 | Hartwell |
| 3,881,491 A | 5/1975 | Whyte |
| 3,921,232 A | 11/1975 | Whyte |
| 3,989,867 A | 11/1976 | Sisson |
| 4,015,604 A | 4/1977 | Csillag |
| 4,100,324 A | 7/1978 | Anderson et al. |
| 4,195,634 A | 4/1980 | DiSalvo et al. |
| 4,247,362 A | 1/1981 | Williams |
| 4,285,343 A | 8/1981 | McNair |
| 4,324,246 A | 4/1982 | Mullane et al. |
| 4,342,314 A | 8/1982 | Radel et al. |
| 4,397,644 A | 8/1983 | Matthews et al. |
| 4,405,326 A | 9/1983 | Lenaghan |
| 4,421,812 A | 12/1983 | Plant |
| 4,425,130 A | 1/1984 | DesMarais |
| 4,463,045 A | 7/1984 | Ahr et al. |
| 4,476,180 A | 10/1984 | Wnuk |
| 4,480,516 A | 11/1984 | Leroy |
| 4,490,147 A | 12/1984 | Pierce et al. |
| 4,496,359 A | 1/1985 | Pigneul |
| 4,536,181 A | 8/1985 | Cook |
| 4,556,146 A | 12/1985 | Swanson et al. |
| 4,556,560 A | 12/1985 | Buckingham |
| 4,573,986 A | 3/1986 | Minetola et al. |
| 4,576,596 A | 3/1986 | Jackson et al. |
| 4,576,597 A | 3/1986 | Hlaban et al. |
| 4,578,070 A | 3/1986 | Holtman |
| 4,589,876 A | 5/1986 | Van Tilburg |
| 4,608,047 A | 8/1986 | Mattingly |
| 4,654,040 A | 3/1987 | Luceri |
| 4,655,759 A | 4/1987 | Romans-Hess et al. |
| 4,662,876 A | 5/1987 | Wiegner |
| 4,687,478 A | 8/1987 | Van Tilburg |
| 4,701,177 A | 10/1987 | Ellis et al. |
| RE32,649 E | 4/1988 | Brandt et al. |
| 4,738,677 A | 4/1988 | Foreman |
| 4,753,644 A | 6/1988 | Cottenden et al. |
| 4,758,240 A | 7/1988 | Glassman |
| 4,804,380 A | 2/1989 | Lassen et al. |
| 4,846,824 A | 7/1989 | Lassen et al. |
| 4,879,170 A | 11/1989 | Radwanski et al. |
| 4,886,513 A | 12/1989 | Mason, Jr. et al. |
| 4,936,839 A | 6/1990 | Molee et al. |
| 4,950,264 A | 8/1990 | Osborn, III |
| 4,961,736 A | 10/1990 | McCloud |
| 4,964,857 A | 10/1990 | Osborn |
| 4,973,325 A | 11/1990 | Sherrod et al. |
| 5,007,906 A | 4/1991 | Osborn, III et al. |
| 5,009,653 A | 4/1991 | Osborn, III |
| 5,030,314 A | 7/1991 | Lang |
| 5,147,343 A | 9/1992 | Kellenberger |
| 5,147,345 A | 9/1992 | Young et al. |
| 5,151,092 A | 9/1992 | Buell et al. |
| 5,171,302 A | 12/1992 | Buell |
| 5,188,625 A | 2/1993 | Van Iten et al. |
| 5,217,445 A | 6/1993 | Young et al. |
| 5,217,447 A | 6/1993 | Gagnon |
| 5,219,342 A | 6/1993 | Hatch et al. |
| 5,235,515 A | 8/1993 | Ungpiyakul et al. |
| 5,236,428 A | 8/1993 | Zajaczkowski |
| 5,267,992 A | 12/1993 | Van Tilburg |
| 5,300,055 A | 4/1994 | Buell |
| 5,308,346 A | 5/1994 | Sneller et al. |
| 5,324,278 A | 6/1994 | Visscher et al. |
| 5,324,575 A | 6/1994 | Sultze et al. |
| 5,342,337 A | 8/1994 | Runeman et al. |
| 5,342,342 A | 8/1994 | Kitaoka |
| 5,350,624 A | 9/1994 | Georger et al. |
| 5,354,400 A | 10/1994 | Lavash et al. |
| 5,360,420 A | 11/1994 | Cook et al. |
| 5,389,094 A | 2/1995 | Lavash et al. |
| 5,399,175 A | 3/1995 | Glaug et al. |
| 5,399,412 A | 3/1995 | Sudall et al. |
| 5,401,267 A | 3/1995 | Couture-Dorschner et al. |
| 5,413,568 A | 5/1995 | Roach et al. |
| 5,415,643 A | 5/1995 | Kolb |
| 5,429,628 A | 7/1995 | Trinh et al. |
| 5,429,629 A | 7/1995 | Latimer et al. |
| 5,429,630 A | 7/1995 | Beal et al. |
| 5,445,628 A | 8/1995 | Gipson et al. |
| 5,447,507 A | 9/1995 | Yamamoto |
| 5,462,166 A | 10/1995 | Minton et al. |
| 5,476,457 A | 12/1995 | Roessler et al. |
| 5,487,736 A | 1/1996 | Van Phan |
| 5,489,283 A | 2/1996 | Van Tillburg |
| 5,506,035 A | 4/1996 | Van Phan et al. |
| 5,514,104 A | 5/1996 | Cole et al. |
| 5,518,801 A | 5/1996 | Chappell et al. |
| 5,520,674 A | 5/1996 | Lavon et al. |
| 5,533,991 A | 7/1996 | Kirby et al. |
| 5,542,941 A | 8/1996 | Morita |
| 5,545,156 A | 8/1996 | DiPalma et al. |
| 5,547,745 A | 8/1996 | Hansen et al. |
| 5,562,645 A | 10/1996 | Tanzer et al. |
| 5,562,650 A | 10/1996 | Everett et al. |
| 5,567,260 A | 10/1996 | McFall |
| 5,575,785 A | 11/1996 | Gryskiewicz et al. |
| 5,591,146 A | 1/1997 | Hasse |
| 5,591,148 A | 1/1997 | McFall et al. |
| 5,591,150 A | 1/1997 | Olsen et al. |
| 5,599,339 A | 2/1997 | Horney |
| 5,601,544 A | 2/1997 | Glaug et al. |
| 5,611,790 A | 3/1997 | Osborn, III et al. |
| 5,618,282 A | 4/1997 | Schlangen |
| 5,620,430 A | 4/1997 | Bamber |
| 5,624,423 A | 4/1997 | Anjur et al. |
| 5,649,917 A | 7/1997 | Roberts et al. |
| 5,672,248 A | 9/1997 | Wendt et al. |
| 5,692,939 A | 12/1997 | DesMarais |
| 5,693,411 A | 12/1997 | Hansen et al. |
| 5,702,378 A | 12/1997 | Widlund et al. |
| 5,704,928 A | 1/1998 | Morita et al. |
| 5,704,930 A | 1/1998 | Lavash et al. |
| 5,704,932 A | 1/1998 | Hibbard |
| 5,711,970 A | 1/1998 | Lau et al. |
| 5,720,738 A | 2/1998 | Clark |
| 5,725,821 A | 3/1998 | Gannon et al. |
| 5,746,729 A | 5/1998 | Wada et al. |
| 5,753,343 A | 5/1998 | Braun et al. |
| 5,756,039 A | 5/1998 | McFall et al. |
| 5,766,213 A | 6/1998 | Hackman et al. |
| 5,769,834 A | 6/1998 | Reiter et al. |
| 5,772,967 A | 6/1998 | Wannlund et al. |
| 5,773,120 A | 6/1998 | Deka et al. |
| 5,779,860 A | 7/1998 | Hollenberg et al. |
| 5,795,921 A | 8/1998 | Dyer et al. |
| H1750 H | 9/1998 | Dobrin |
| 5,800,417 A | 9/1998 | Goerg-Wood et al. |
| 5,817,079 A | 10/1998 | Bergquist et al. |
| 5,817,081 A | 10/1998 | LaVon et al. |
| 5,817,394 A | 10/1998 | Alikhan et al. |
| 5,820,616 A | 10/1998 | Horney |
| 5,824,004 A | 10/1998 | Osborn, III et al. |
| 5,846,230 A | 12/1998 | Osborn, III et al. |
| 5,851,648 A | 12/1998 | Stone et al. |
| 5,853,867 A | 12/1998 | Harada et al. |
| 5,858,011 A | 1/1999 | Brown et al. |
| 5,858,021 A | 1/1999 | Sun et al. |

| | | | |
|---|---|---|---|
| 5,865,824 A | 2/1999 | Chen et al. | |
| 5,869,033 A | 2/1999 | Schulz | |
| 5,874,070 A | 2/1999 | Trinh et al. | |
| 5,874,071 A | 2/1999 | Yu et al. | |
| 5,876,393 A | 3/1999 | Ahr et al. | |
| 5,910,137 A | 6/1999 | Clark et al. | |
| 5,954,705 A | 9/1999 | Sawaki et al. | |
| 5,957,909 A | 9/1999 | Hammons et al. | |
| 5,990,377 A | 11/1999 | Chen et al. | |

FOREIGN PATENT DOCUMENTS

| | | |
|---|---|---|
| EP | 0520884 A1 | 12/1992 |
| EP | 0 117 613 B2 | 3/1993 |
| EP | 0 564 307 A1 | 10/1993 |
| EP | 0687453 A1 | 12/1995 |
| EP | 0 612 233 B1 | 4/1996 |
| EP | 0 552 345 B1 | 9/1996 |
| EP | 0 516 964 B1 | 11/1996 |
| EP | 0758543 A1 | 2/1997 |
| EP | 0768070 A1 | 4/1997 |
| EP | 0 638 303 B1 | 11/1997 |
| EP | 0804914 A1 | 11/1997 |
| EP | 0815817 A1 | 1/1998 |
| EP | 0 652 736 B1 | 10/1998 |
| EP | 0868894 A1 | 10/1998 |
| EP | 0 419 434 B2 | 11/1998 |
| EP | 0 758 220 B1 | 12/1998 |
| EP | 0 893 517 A2 | 1/1999 |
| EP | 0945110 A2 | 9/1999 |
| GB | 2168612 A | 6/1986 |
| GB | 2306333 A | 5/1997 |
| WO | WO 83/03051 A1 | 9/1983 |
| WO | WO 92/07535 A1 | 5/1992 |
| WO | WO 93/21879 A1 | 11/1993 |
| WO | WO 94/24973 A1 | 11/1994 |
| WO | WO 95/24878 A1 | 9/1995 |
| WO | WO 97/19808 A1 | 6/1997 |
| WO | WO 97/24283 A1 | 7/1997 |
| WO | WO 98/22059 A1 | 5/1998 |
| WO | WO 98/24391 A2 | 6/1998 |
| WO | WO 98/43684 A1 | 10/1998 |
| WO | WO 99/00093 A1 | 1/1999 |
| WO | WO 99/12502 A1 | 3/1999 |
| WO | WO 00/19955 A2 | 4/2000 |
| WO | WO 00/19956 A1 | 4/2000 |
| ZA | 98/4033 | 5/1998 |

CENTER-FILL ABSORBENT ARTICLE WITH A WICKING BARRIER AND CENTRAL RISING MEMBER

CROSS REFERENCE TO RELATED APPLICATION

This application is a continuation of application Ser. No. 09/411,259, filed on Oct. 1, 1999 now U.S. Pat. No. 6,492,547.

BACKGROUND OF THE INVENTION

To prevent leakage of body exudates from absorbent articles such as feminine care pads or napkins and disposable diapers, it is desirable that the exudates not reach the edges of the absorbent material in the article. A "center fill" strategy is desirable for leakage control, wherein fluids are preferentially held in a central region of the article. Unfortunately, in traditional absorbent articles, there is generally no barrier to bulk flow or capillary wicking from the target region to the edges of the article, so leaking from the edges of the article is a persistent problem. Thus, in traditional articles, fluid entering the center of the article still has the potential to travel to the sides and leak. Flow from the center to the sides can be especially rapid when the article is compressed, bringing the wet central portion of the article in contact with absorbent material at the sides of the article.

What is needed is an article with good center fill performance that can reduce leakage to the sides of the article. Further, the article should offer excellent body fit through a three-dimensional topography that becomes more pronouncedly three-dimensional when the article is worn and compressed between the legs of the wearer while still maintaining comfort.

SUMMARY OF THE INVENTION

It has been discovered that improved body fit and leakage control can be obtained in absorbent articles by providing an absorbent core comprising an outer absorbent member and a central absorbent member operatively associated with a central rising member. The central rising member, described more fully hereafter, is an element which deflects upwards when laterally compressed from the side. The central absorbent member is operatively associated with the central rising member such that the upward deflection of the central rising member also causes the central absorbent member to deflect upward (i.e., toward the source of fluid exudates to be absorbed). In addition, a wicking barrier is incorporated between the outer absorbent member and central absorbent member. The wicking barrier can be an impermeable film or a liquid pervious web offering substantial resistance to wicking and flow.

Desirably, the wicking barrier has a vertical component spanning a vertical distance between the central absorbent member and the outer absorbent member, and also desirably, has a horizontal component spanning a distance on the body-side surface of the outer absorbent member.

The horizontal component or "ledge" that is part of the wicking barrier in preferred embodiments helps prevent contact between the outer absorbent member and the central absorbent member when the article is bunched together during use. The combination of improved body fit due to the action of the central rising member and the fluid isolation of the central absorbent member by the wicking barrier results in a particularly efficient absorbent article with reduced potential for leakage. The wicking barrier can also help control the geometry of the absorbent article when in use under dynamic conditions, permitting flexure or folding such that the central absorbent member is deflected toward the body. When the outer absorbent member is provided with a central void, as hereinafter described, the wicking barrier desirably lines all or a portion of the walls of the central void.

The ledge can also provide increased stability, strength, and resiliency to an absorbent article. This is particularly so when the ledge is adhesively or otherwise attached to the cover or topsheet of an absorbent article and/or to one or more elements of the absorbent core. A problem in some previous attempts at providing isolated chambers in an absorbent article is that a film or other barrier between adjacent chambers eliminates the fiber—fiber bonding or entanglement between fibers that holds an absorbent core together, resulting in an absorbent core which can come apart in tension or compression or during bending. In preferred embodiments of the present invention, the ledge of the wicking barrier is easily attached to the cover and can further be attached to either or both of the central absorbent member and the outer absorbent member adhesively, by thermal or ultrasonic bonds, or by other attachment means known to one skilled in the art. By geometric considerations alone, a wicking barrier with a ledge can effectively hold the central absorbent member in place between the wicking barrier and the cover when the ledge is attached to the cover or to the surface of the outer absorbent member.

Desirably, the ledge (the horizontal component of the wicking barrier) covers about 30% or more, specifically about 50% or more and most specifically about 80% or more of the body-side surface of the outer absorbent member along the transverse axis of the article, with essentially 100% coverage in the target zone being desirable in many embodiments.

The central absorbent member can be formed from any known absorbent material such as cellulosic fibrous webs and the like. It generally is the primary absorbent component of the article and is at least partially surrounded by an outer absorbent member a width (taken as the total edge-to-edge span in the transverse direction) greater than the width of the central absorbent member.

The outer absorbent member typically serves as a frame or shaping element for the absorbent article, in part by virtue of its ability to remain dry and resilient in use. The outer absorbent member can also serve as a backup absorbent reservoir when the central absorbent member is becoming saturated or threatened with leakage. The outer absorbent member can be both wider and longer than the central absorbent member, and has a central void for receiving at least a portion of the central absorbent member and optionally for receiving the central rising member. In the target zone, folding of the outer absorbent member in use coupled with the upward deflection of the central absorbent member generally results in a W-shaped absorbent article well suited for maintaining good body fit and for absorbing fluids effectively from the body of the wearer.

The central rising member can be operatively associated with the central absorbent member in several ways. The central rising member can be disposed below the central absorbent member, either in direct contact with the central absorbent member or with a wicking barrier or other element disposed therebetween. Alternatively, the central rising member can be a structure embedded within the absorbent material of the absorbent core and specifically within the central absorbent member, capable of upwardly deflecting the central absorbent member or at least the absorbent material in the central absorbent member that lies above the central rising member. Also alternatively, the central rising member itself can be an absorbent component of the central absorbent member or can be the major component of the central absorbent member, forming at least the predominant part of the central absorbent member. Thus, the central rising member can rise toward the body in response to lateral compression and then directly absorb body exudates.

Further improvements in body fit and deformation of the article in use can be achieved by adding additional features to the articles of the present invention. For example, improved deformation can also be promoted or assisted by one or more shaping lines and/or one or more crease lines in the absorbent core. A crease line lies away from the longitudinal centerline and promotes downward folding or bending of the article along the crease line (e.g., a valley fold) during lateral compression from the longitudinal sides of the article. A shaping line resides in the central absorbent member and promotes upward folding or bending (e.g., a mountain fold) during lateral compression from the longitudinal sides of the article. A shaping line coupled with at least two crease lines works to establish a W-fold geometry in the article when laterally compressed, offering good control over the upward deflection of a central absorbent member in the absorbent core. Crease lines and shaping lines, as defined therein, will be generally referred to hereafter as "bending lines."

Hence, in one aspect, the invention resides in an absorbent article having two longitudinal sides and a target zone, comprising:

a) a liquid impervious backsheet;
b) a liquid pervious topsheet attached to the backsheet; and
c) an absorbent core positioned between the topsheet and the backsheet, the absorbent core comprising an outer absorbent member, a central absorbent member operatively associated with a central rising member, and a wicking barrier disposed between the outer absorbent member and the central absorbent member, the outer absorbent member having a width in the target zone greater than the width of the central absorbent member in the target zone, whereby lateral compression of the absorbent core from the longitudinal sides causes the central rising member to deflect the central absorbent member away from the backsheet.

In another aspect, the invention resides in an absorbent article having a target zone, a longitudinal direction, a transverse direction, and a vertical direction substantially normal to both the longitudinal and transverse directions, the absorbent article comprising:

a) an absorbent core having a central absorbent member and an outer shaping member, the outer shaping member defining a central void for receiving at least a portion of the central absorbent member, whereby an interface is defined between the central absorbent member and the outer shaping member, the interface spanning a vertical distance,
b) a wicking barrier disposed along the interface between the central absorbent member and the outer absorbent member; and
c) at least one of a central rising member and a central inflatable member disposed beneath the central absorbent member.

In another aspect, the invention resides in an absorbent article comprising a topsheet, a backsheet joined to the topsheet, an absorbent core disposed between the backsheet and the topsheet, the absorbent core comprising a central absorbent member operatively associated with a central rising member, the central rising member having longitudinal sides and a longitudinally central hinge dividing the central rising member into a first portion and second portion, the article (or more specifically, the absorbent core) further comprising attachment means in cooperative relationship with the central rising member, wherein application of inwardly lateral compressive force to the longitudinal sides of the central rising member causes the central rising member to deflect upward along the longitudinally central hinge, and wherein the attachment means holds the central rising member in an upwardly deflected state when the inwardly lateral compressive force is relaxed.

In the absorbent article of the above embodiment, the central rising member can further comprise a garment-side surface, and the attachment means can comprise a first attachment section on the garment-side surface of the first portion of the central rising member and a second attachment section on the garment-side surface of the second portion of the central rising member, wherein the first attachment section connects to the second attachment section when the garment-side surface of the first portion of the central rising member is brought into contacting relationship with the garment-side surface of the second portion of the central rising member. The attachment means can comprise a mechanical attachment means such as a hook and loop system disposed on the garment-side surface of the central rising member. The attachment means can also be a ratchet-and-prawl analog, wherein the longitudinal sides of the central rising member such as an absorbent web superposed over a narrow pledget engage elevated ratchet-like structures (depressions, elevated barriers, grooves, and the like) on the surface of a resilient wicking barrier, wherein lateral compression of the absorbent web can move the longitudinal sides of the absorbent web closer to the longitudinal centerline, whereupon the longitudinal sides of the absorbent web can then be restrained by the ratchet-like wicking barrier to hold the absorbent web in an upwardly flexed state even after lateral compressive forces are removed or-relaxed.

In another aspect, the invention resides in a method for producing an absorbent article having a central absorbent member, the method comprising:

a) preparing an outer absorbent member, wherein the outer absorbent member has a central void;
b) disposing a wicking barrier over the outer absorbent member;
c) disposing a central absorbent member in the central void and over a portion of the wicking barrier;
d) disposing a central rising member beneath the central absorbent member;
e) disposing a backsheet beneath the central rising member and beneath the outer absorbent member;
f) disposing a topsheet above the central absorbent member and the outer absorbent member; and
g) attaching the topsheet to the backsheet.

In yet another aspect, the invention resides in a method for producing an absorbent article having a central absorbent member, the method comprising:

a) preparing an outer absorbent member, wherein the outer absorbent member has a central void;
b) disposing a central rising member in the central void;
c) disposing a layer of a flexible barrier material over the central void; and d) inserting a section of absorbent material into the central void and over the barrier material to form a central absorbent member, such that a portion of the barrier material separates the central absorbent member from the outer absorbent member along a vertical distance.

The above method may further comprise disposing a backsheet beneath the absorbent core; disposing a topsheet above the absorbent core; and attaching a portion of the topsheet to a portion of the backsheet.

In yet another aspect, the invention resides in a method for producing an absorbent article having a central absorbent member, a garment side, and a body side, the method comprising:

a) providing a section of an absorbent web;

b) slitting the absorbent web longitudinal to form a central strip and two side strips;

c) placing a composite insert beneath the central strip and above the two side strips, the composite insert having a width greater then the width of the central strip, the composite insert comprising a wicking barrier attached to a central rising member, the central rising member being placed beneath the central strip, wherein the central strip, the two side strips, and the composite insert form an absorbent core having a garment side and a body side;

d) joining a backsheet to the garment side of the absorbent core;

e) disposing a topsheet above the absorbent core; and f) attaching the topsheet to the backsheet.

Possible uses of the present invention include absorbent articles for intake, distribution, and retention of human body fluids. Examples include feminine care pads and related catamenial devices or sanitary napkins, including "ultra-thin" pads and pantiliners and maxipads. Likewise, the present invention can be applied to diapers, disposable training pants, other disposable garments such as swimming garments, incontinence articles, bed pads, medical absorbents, wound dressings or other absorbent articles. The articles of the present invention provide significant leakage protection, fluid center-fill absorptive performance, and other desirable attributes for absorbent articles.

DEFINITIONS

"Absorbency Under Load"(AUL) is a measure of the liquid retention capacity of a material under a mechanical load. It is determined by a test which measures the amount in grams of an aqueous solution, containing 0.9 weight percent sodium chloride, a gram of a material can absorb in 1 hour under an applied load or restraining force of about 2 kPa (0.3 pound per square inch).

The AUL apparatus comprises a Demand Absorbency Tester (DAT) as described in U.S. Pat. No. 5,147,343, issued Sep. 15, 1992 to Kellenberger, herein incorporated by reference, which is similar to a GATS (Gravimetric Absorbency Test System), available from M/K Systems, Danners, Mass.

As used herein, a material is said to be "absorbent" if it can retain an amount of water equal to at least 100% of its dry weight as measured by the test for Intrinsic Absorbent Capacity given below (i.e., the material has an Intrinsic Absorbent Capacity of at about 1 or greater). Desirably, the absorbent materials used in the absorbent members of the present invention have an Intrinsic Absorbent Capacity of about 2 or greater, more specifically about 4 or greater, more specifically still about 7 or greater, and more specifically still about 10 or greater, with exemplary ranges of from about 3 to about 30 or from about 4 to about 25 or from about 12 to about 40.

As used herein, "absorbent capacity" refers to the total mass of water that a specified quantity of absorbent material can hold, and is simply the Intrinsic Absorbent Capacity multiplied by the dry mass of the absorbent material. Thus 10 g of material having an Intrinsic Absorbent Capacity of 5 has an absorbent capacity of 50 g (or about 50 ml of fluid).

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity and 23° C.) after conditioning for at least four hours. Samples should be essentially flat and uniform under the area of the contacting platen. Bulk is expressed as volume per mass of fiber in cc/g and density is the inverse, g/cc.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

As used herein, "Central Elevation" is defined as the height difference between the center of the central absorbent member along the transverse centerline of the article and the average height of the longitudinal sides of the central absorbent member along the transverse centerline of the article at the end of the Vertical Deformation Test hereinafter described. The Central Elevation for absorbent articles of the present invention can be at least about 0.5 cm, specifically at least about 1 cm, and more specifically at least about 1.2 cm and up to about 10 cm. Desirably, an absorbent article of the present invention exhibits an increase in Central Elevation in the crotch region of at least about 20%, and more specifically at least about 50%, relative to the Central Elevation in the crotch region exhibited by an essentially identical absorbent article without a shaping line.

As used herein, the "crotch region" of an absorbent article refers to the generally central region that will be in contact with the crotch of the user, near the lowermost part of the torso, and resides between the front and rear portions of the article. Typically the crotch region contains the transverse centerline of the article and generally spans approximately 7 to 10 cm in the longitudinal direction.

Many articles of the present invention are intended to be worn in the crotch of a wearer, and thus have crotch regions. However, the present invention can also be applied to other articles such as underarm pads or wound dressings where a crotch region may not exist. In such cases, the article will have a region where fluid intake is intended to occur, termed the "target region." The portion of the article including the longitudinal length of the target region and the full transverse width of the article normal to length of the target region is defined herein as the "target zone." For articles intended to be worn in the crotch, the terms "target zone" and "crotch region" are generally synonymous, whereas "target region" generally excludes the portions of the absorbent core near the longitudinal sides since the intended area for fluid intake is generally substantially central in the absorbent article.

As used herein, the term "extensible" refers to articles that can increase in at least one of their dimensions in the x-y plane by at least 10% and desirably at least 20%. The x-y plane is a plane generally parallel to the faces of the article. The term extensible includes articles that are stretchable and elastically stretchable (defined below). In the case of a sanitary napkin comprising an absorbent core, for example, the article and the absorbent core are desirably extensible both in length and width. The absorbent article, however, may only be extensible in one of these directions. Preferably, the article is extensible at least in the longitudinal direction. Examples of extensible materials and articles, and their methods of preparation, are disclosed in U.S. Pat. No. 5,611,790, issued Mar. 18, 1997 to Osborn, herein incorporated by reference in its entirety.

As used herein, a bulk material (e.g., the absorbent components of the article or the material providing shape in the outer shaping member) is considered "flexible" if a straight, TAPPI-conditioned (50 percent relative humidity at 23° C.) strip of the material 25 cm long with a cross-section of 1 cm×1 cm can be bent 180° around a 5-cm diameter rod without breaking and without requiring application of more than 6 Newtons of force to the ends of the strip to cause the bending over a 3-second span of time.

As used herein, the term "flexure-resistant" refers to an element which will support a bending moment, in contrast to an element which will support only axial forces. Likewise, as used herein, "flexure resistance" is a means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of Peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. For comfort, the absorbent article desirably has a flexure-resistance of less than or equal to about 1,500 grams, more specifically about 1000 grams or less, more specifically still about 700 grams or less and most specifically about 600 grams or less. For shaping performance, the central absorbent member as well as the outer absorbent member can have a flexure resistance of at least about 30 grams, more specifically at least about 50 grams, and most specifically at least about 150 grams.

As used herein, "Free Swell Capacity" (FS) is the result of a test which measures the amount in grams of an aqueous solution, containing 0.9 weight percent sodium chloride, that a gram of a material can absorb in 1 hour under negligible applied load. The test is done as described above for the AUL test, except that the 100 gm weight used in the AUL test is not placed on the sample.

The Free Swell Capacity of the materials of the present invention can be above 8, more specifically above 10, more specifically above 20, and most specifically above 30 grams/gram.

As used herein, "Free Swell:AUL Ratio" is the ratio of Free Swell Capacity to AUL. It will generally be greater than one. The higher the value, the more sensitive the material is to compressive load, meaning that the sample is less able to maintain its potential pore volume and capillary suction potential under load. Desirably, the materials of the present invention have "Free Swell:AUL Ratio" of about 4 or less, more specifically about 2 or less, more specifically still about 1.5 or less, and more specifically about 1.3 or less, with an exemplary range of from about 1.2 to about 2.5.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin.

As used herein, the term "horizontal," refers to directions in the plane of the article that are substantially parallel to the body-side surface of the article, or, equivalently, substantially normal to the vertical direction of the article, and comprises the transverse direction and the longitudinal direction of the article, as well as intermediate directions. The orientation of components in an article, unless otherwise specified, is determined as the article lies substantially flat on a horizontal surface.

As used herein, the term "hydrophobic" refers to a material having a contact angle of water in air of at least 90 degrees. In contrast, as used herein, the term "hydrophilic" refers to a material having a contact angle of water in air of less than 90 degrees.

As used herein, "Intrinsic Absorbent Capacity" refers to the amount of water that a saturated sample can hold relative to the dry weight of the sample and is reported as a dimensionless number (mass divided by mass). The test is performed according to Federal Government Specification UU-T-595b. It is made by cutting a 10.16 cm long by 10.16 cm wide (4 inch long by 4 inch wide) test sample, weighing it, and then saturating it with water for three minutes by soaking. The sample is then removed from the water and hung by one corner for 30 seconds to allow excess water to be drained off. The sample is then re-weighed, and the difference between the wet and dry weights is the water pickup of the sample expressed in grams per 10.16 cm long by 10.16 cm wide sample. The Intrinsic Absorbent Capacity value is obtained by dividing the total water pick-up by the dry weight of the sample. If the material lacks adequate integrity when wet to perform the test without sample disintegration, the test method may be modified to provide improved integrity to the sample without substantially modifying its absorbent properties. Specifically, the material may be reinforced with up to 6 lines of hot melt adhesive having a diameter of about 1 mm applied to the outer surface of the article to encircle the material with a water-resistant band. The hot melt should be applied to avoid penetration of the adhesive into the body of the material being tested. The corner on which the sample is hung in particular should be reinforced with external hot melt adhesive to increase integrity if the untreated sample cannot be hung for 30 seconds when wet.

"Papermaking fibers," as used herein, include all known cellulosic fibers or fiber mixes comprising cellulosic fibers. Fibers suitable for making the webs of this invention comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, and aspen. Woody fibers can be prepared in high-yield or low-yield forms and can be pulped in any known method, including kraft, sulfite, high-yield pulping methods, and other known pulping methods. Chemically treated natural cellulosic fibers can be used such as mercerized pulps, chemically stiffened or crosslinked fibers, or sulfonated fibers. Suitable papermaking fibers can also include recycled fibers, virgin fibers, or mixes thereof.

As used herein, a "pledget" refers to an absorbent insert within an absorbent core having at least one of a width and a length smaller than the respective width and length of the absorbent core. A pledget is generally used to cause deformation or shaping of an adjoining layer of an absorbent article, and in the present invention, can be of use in shaping a pad or creating a medial hump in the pad for improved fit against the body of the wearer.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as panty liners, or other absorbent articles such as diapers or incontinence pads. The term "feminine care pad" as used herein is synonymous with sanitary napkin.

The term "stretchable", as used herein, refers to articles that are extensible when stretching forces are applied to the article and offer some resistance to stretching. The terms "elastically stretchable" or "elastically extensible" are intended to be synonymous. These terms, as used herein, mean that when in-plane stretching forces are removed, the article or absorbent fibrous structure will tend to return toward its unextended or unstretched dimensions (or original dimensions). It need not return all the way to its unstretched dimensions, however. It may return to relaxed dimensions between its unstretched dimensions and extended (or stretched dimensions).

As used herein, "thickness" of a fluff pad or other absorbent element refers to thickness measured with a platen-based thickness gauge having a diameter of 7.62 cm at a load of about 0.05 pounds per square inch (psi) [about 35 kilograms per square meter]. The thickness of the central absorbent member or the outer absorbent member or of the absorbent article in general can be from about 2 mm to about 50 mm, more specifically from about 3 mm to about 25 mm, more specifically still from about 3 mm to about 15 mm, and most specifically from about 4 mm to about 10 mm. Ultrathin articles can have a thickness less than about 6 mm.

As used herein, the term "transverse" refers to a line, axis, or direction which lies within the plane of the absorbent article and is generally perpendicular to the longitudinal direction. The z-direction is generally orthogonal to both the longitudinal and transverse centerlines. The term "lateral" refers to substantially in-plane directions having a predominately transverse component. Likewise, "inwardly lateral compression" refers to compression directed from the longitudinal sides of an article toward the longitudinal centerline thereof, applied substantially in the transverse direction.

The degree of elevation of the central absorbent member can be quantified in terms of a Vertical Deformation test. As used herein, "Vertical Deformation" refers to the height increase experienced by the body-side surface of an absorbent article when the longitudinal sides in the crotch reason are gripped and steadily moved inward toward the longitudinal axis of the article, decreasing the span between the longitudinal sides by 1.5 cm. The Vertical Deformation test apparatus comprises two clamps having a clamp width (longitudinal length of the clamped portion of the edge of the article) of 5 cm. One clamp is stationary and the other is on a track that permits the clamp to slide to increase or decrease the distance between the clamps while keeping the clamp aligned and parallel to the other clamp. The clamps should be tilted downward at an angle of 20 degrees relative to horizontal, such that both outer edges of the absorbent article are slightly elevated relative to the nearest crease line, thus somewhat simulating the positioning of the outward edges of the absorbent article that may be induced by panties with elevated elastic edges in the crotch region. The clamps are 5 cm above the surface of the track, permitting a pad to be suspended in air between the clamps, gripped in the crotch area such that a portion of the longitudinal sides of the absorbent core are held, with the clamps extending inward no more than about 3 mm from the outer edge of the absorbent core. The article should be held substantially taut in the region between the clamps without damaging the article, such that the crotch region is substantially horizontal before lateral compression begins. At a rate of about 0.5 centimeters per second (cm/s), the slideable clamp is moved smoothly toward the fixed clamp by a distance of 50% of the initial width of the article in the crotch region (or less if the article become incompressible such that more than about 5 kg of force is required to further compress the article). The height of the center of the pad or absorbent article is recorded before the clamp is moved and after the clamp is moved, yielding a difference that is reported as the Vertical Deformation. An increase in height is reported as a positive number, while a decrease is reported as a negative number. Desirably, the Vertical Deformation of the absorbent article is at least about 0.5 cm. Specifically, the Vertical Deformation is at least about 1 cm, and more specifically is at least about 1.5 cm and up to about 10 cm. Desirably, an absorbent article of the present invention exhibits an increase in Vertical Deformation in the crotch region of at least about 20%, and more specifically at least about 50%, relative to the Vertical Deformation in the crotch region exhibited by an essentially identical absorbent article without a shaping line.

As used herein, "Wet Bulk" is based on a caliper measurement of a sample according to the definition of "bulk" above (at 0.344 kPa), except that the conditioned sample is uniformly misted with deionized water until the moistened mass of the sample is approximately 250% of the dry mass of the sample (i.e., the added mass of the moisture is 150% of the dry sample weight). If the sample cannot absorb and retain enough moisture from misting to increase the mass by 150%, then the highest level of achievable moisture add-on below 150% but still above 100% moisture add on should be used. The Wet Bulk in cc/g is calculated as the thickness of the substantially planar moistened sample under a load of 0.344 kPa (0.05 psi) divided by the oven-dry sample basis weight. Absorbent materials in the absorbent members of the present invention can have a Wet Bulk of about 4 cc/g or greater, more specifically about 6 cc/g or greater, more specifically still about 10 cc/g or greater, more specifically still about 10 cc/g or greater, and most specifically about 15 cc/g or greater, with an exemplary range of from about 5 cc/g to about 20 cc/g.

DETAILED DESCRIPTION OF THE DRAWINGS

Figure 1:
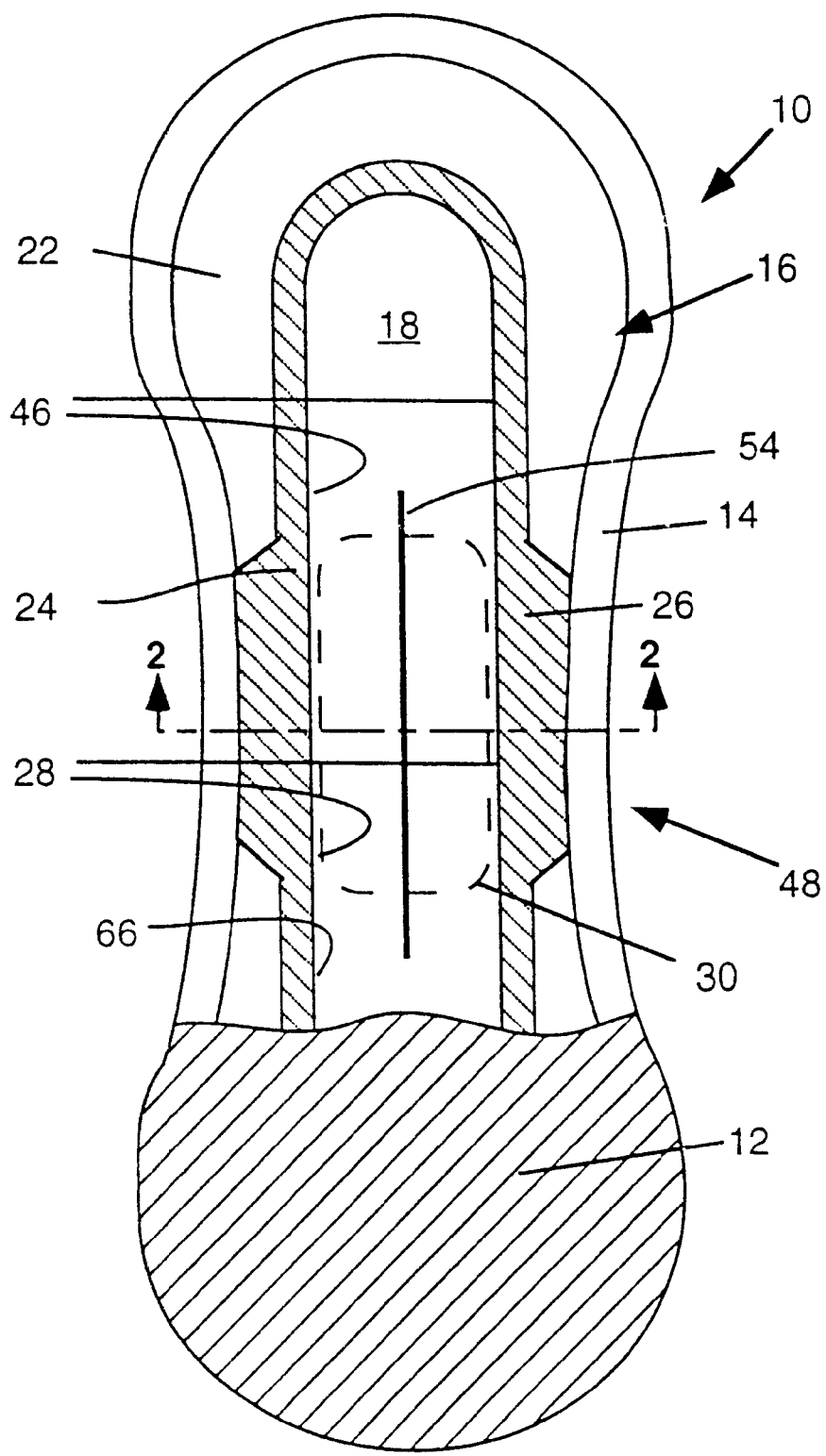
FIG. 1 depicts a top view of a sanitary napkin according to the present invention.

FIG. 1 presents a top view of an absorbent article 10 according to the present invention as viewed from above. The article is covered with a topsheet 12, which is cut away for most of the article 10 to show underlying components. The topsheet 12 is connected to the backsheet 14, which is intended to be against the garments of the wearer. Between the topsheet 12 and the backsheet 14 is the absorbent core 16, which includes a central absorbent member 18 surrounded by an outer absorbent member 22. The outer absorbent member 22 in this case is said to surround the central absorbent member 18 because, when viewed from above, the outer absorbent member 22 has portions lying outside of the longitudinal edges 46 of the central absorbent member 18. The outer absorbent member 22 need not surround the central absorbent member 18 along any transverse cross-section, but should surround the central absorbent member 18 in the target zone 48 of the absorbent article 10, where leakage is most likely to occur in traditional articles.

The outer absorbent member 22 has a central void 66 for receiving the central absorbent member 18. The central void 66 of the outer absorbent member 22 desirably is a region of reduced basis weight relative to the other regions of the outer absorbent member 22, but can also be a region which has been compressed in thickness substantially such that a depression is defined which can receive an absorbent insert to serve as a central absorbent member 18.

The central absorbent member 18 has an optional shaping line 54 (e.g., a slit) to help direct upward flexure of the central absorbent member 18 in the shape of an inverted "V" during lateral compression. The central absorbent member 18 can comprise between about 10% and 90% of the mass of the absorbent core 16 on a dry basis, more specifically between about 20% and 70%, more specifically still between about 20% and 60%, and most specifically from about 25% to less than 50%.

Figure 2:
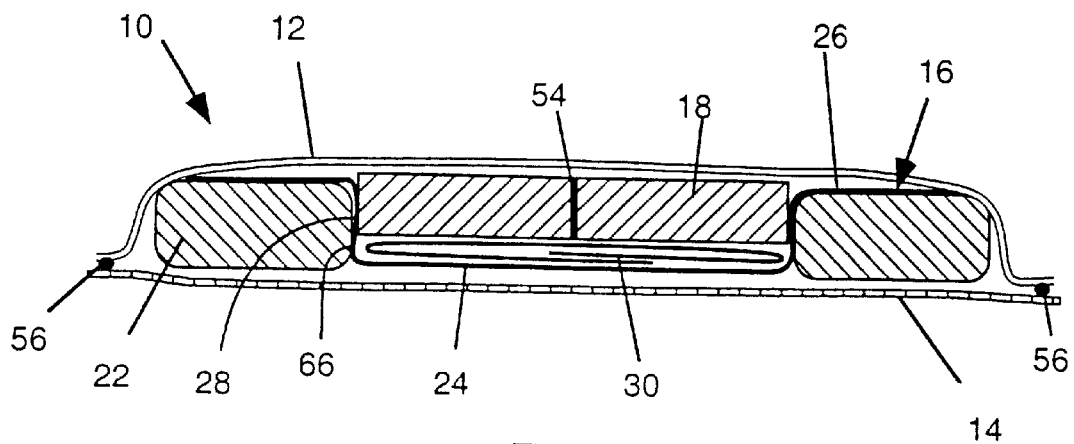
FIG. 2 depicts a cross-section of sanitary napkin of the present invention having a central rising member disposed below the central absorbent member.

In one preferred embodiment, the central absorbent member 18 should be able to deflect upward without being substantially restrained by the outer absorbent member 22, as is the case in FIGS. 1 and 2, where the central absorbent member 18 is substantially unattached to the central absorbent member 22 apart from the common restraint offered by the backsheet 14 and topsheet 12.

The central absorbent member 18 is separated from the outer absorbent member 22 by a wicking barrier 24, which has a vertical component 28 extending into the thickness direction (z-direction) of the article 10 between the outer absorbent member 22 and the central absorbent member 18, and further has a horizontal component 26 extending over a portion of the body-side surface of the outer absorbent member 22. When viewed from above through a translucent topsheet 12, generally only the horizontal component 26 of the wicking baffler 24 will be the visible. The horizontal component 26 has increased width in the target zone 48 (here, the crotch region) such the outer absorbent member 22 is substantially covered in the target zone 48 by the horizontal component 26 of the wicking barrier 24.

The wicking barrier 24 serves to hinder lateral flow from the longitudinal sides 46 of the central absorbent member 18 to the sides of the outer absorbent member 22. Desirably, it spans a finite vertical distance in the absorbent article 10 of about 1 mm or greater, specifically about 2 mm or greater, more specifically about 5 mm or greater, and most specifically from about 3 mm to about 15 mm. In a preferred embodiment, the vertical component 26 spans a vertical distance that is at least about 20 percent, more specifically at least about 50 percent, more specifically still at least about 70 percent, and desirably up to about 100 percent of the average thickness of the central absorbent member 18.

The wicking barrier 24 can be a polymeric film or plastic film; a nonwoven web; a layer of rubber, silicone, or other non-absorbent materials; or a less pervious paper sheet including, for-example, glassine, wax paper, impregnated papers, paper-polymer composites, densified tissue, paper or tissue containing internal sizing to render it less hydrophilic, paper or tissue treated with hydrophobic matter such as wax, silicone, thermoplastic material, or polyolefins. Flexible hydrophobic foams may also be used, such as a closed-cell polyurethane foam or a silicone foam. A hydrophobic web such as a meltblown web of a polyolefin without surfactants or other hydrophilic treatments can also be used, provided that a useful barrier function is achieved. Such materials can include the transfer delay barrier materials disclosed in the commonly owned U.S. patent application Ser. No. 60/079, 657, "An Absorbent System for Personal Care Products Having Controlled Placement of Visco-Elastic Fluids" by A. S. Burnes et al. Desirably, the barrier material will have a porosity less than 20%, specifically less than 10%, more specifically less than 5%, and more specifically the barrier material will be substantially nonporous or substantially impermeable, though a small number of apertures or small openings can be provided in selected portions of the barrier material to prevent oversaturation of the central absorbent section 18. With apertures added, it is still desirable that the average open area of the barrier material be less than 20% and more specifically less than about 5%. (A useful exception is when the wicking barrier is designed to hinder horizontal flow but to allow substantial vertical flow of fluid to an underlying absorbent layer beneath the central absorbent section 18, in which case a large central aperture or hole may be provided in the central portion of the wicking barrier 24 while the outer portions are substantially impervious, particularly the portion that forms the horizontal component 26 around the central absorbent section 18.) In some cases, such as when a barrier material in the form of a flexible polymer sheet is used, including a polypropylene or polyethylene web, the barrier material can have a thickness of about 0.2 mm or less, more specifically about 0.1 mm or less, and most specifically about 0.08 mm or less, with an exemplary range of from about 0.02 mm to about 0.3 mm. A preferred material for the wicking barrier 24 is a thin, flexible polyolefin film desirably having a basis weight less than 40 grams per square meter (gsm) and specifically less than 25 gsm, optionally comprising coloring agents and pigments or fillers such as titanium dioxide or calcium carbonate for opacity.

The wicking barrier 24 can also comprise hydrophobic matter that is used to impregnate a portion of the absorbent core 16 to reduce lateral wicking. Such hydrophobic matter can include hot melt adhesives added to the absorbent article while molten; wax; pastes or emulsions comprising waxes; silicone-based fluids, gels, pastes, or caulk; phenolic resins or other resins which are cured after impregnating the fibrous material of the central absorbent member or outer absorbent member; polyolefins or other plastic or hydrophobic material added as powder, particularly sintered powder, or held in place by adhesives, or by thermal bonding. In addition to the impregnating material, which helps prevent lateral fluid flow in the article, it is also desirable that there be a distinct break, gap, or slit between the central absorbent member 18 and the outer absorbent member 22 in the target zone 48 to further impede fluid communication, especially by removing or severing fibrous pathways between the central absorbent member 18 and the outer absorbent member 22.

Desirably, the Intrinsic Absorbent Capacity (hereafter described) of the wicking barrier 24 is about 1 or less, more specifically less than about 0.5, more specifically still less than about 0.3, and most specifically less than about 0.1. The wicking barrier 24 desirably is substantially non-absorbent. The permeability or porosity or surface chemistry of the wicking barrier 24 can vary with position such that wicking is hindered to differing degrees at different locations.

A central rising member 30, described in more detail below, is disposed beneath the central absorbent member 18 to cause upward deflection of the central absorbent member 18 when the longitudinal sides of the article 10 are compressed laterally inward.

The absorbent material of either the central absorbent member 18 or the outer absorbent member 22 can comprise cellulosic airlaid webs of comminuted fibers (commonly termed "airfelt"); cellulose-superabsorbent mixtures or composites; hydroentangled webs comprising cellulosic fibers; composites of synthetic fibers and papermaking fibers such as coform, as disclosed in U.S. Pat. No. 4,879,170, issued Nov. 7, 1989 to Radwanski et al.; rayon; lyocell or other solvent-spun hydrophilic fibers, such as those disclosed in U.S. Pat. No. 5,725,821, issued Mar. 10, 1998 to Gannon et al.; cellulosic foams including regenerated cellulose foams; hydrophilic, flexible foams or absorbent foams produced from high internal phase emulsions (HIPE), such as the foams disclosed in U.S. Pat. No. 5,692,939, issued Dec. 2, 1997 to DesMarais; fiber-foam composites; the foam-structured fibrous absorbent materials of F. -J. Chen et al. disclosed in the commonly owned, copending U.S. patent application "Fibrous Absorbent Material and Methods of Making the Same," Ser. No. 09/083,873, filed May 22, 1998; absorbent nonwoven webs; cotton; wool or keratin fibers; peat moss and other absorbent vegetable matter, and the like.

In one embodiment, at least one component of the absorbent core 16 comprises a molded, three-dimensional high bulk wet laid cellulosic web, such as an uncreped through-air dried web as taught by F. -J. Chen et al. in commonly owned U.S. patent application, Ser. No. 08/912,906, "Wet Resilient Webs and Disposable Articles Made Therewith," filed Aug. 15, 1997 or U.S. Pat. No. 5,399,412, issued to S. J. Sudall and S. A. Engel on Mar. 21, 1995. Such uncreped structures can offer a plurality of flow channels along the surface of the web. When stacked or layered with other planar materials such as a polymer film, void space can still exist adjacent the surface of the tissue web to permit rapid flow of fluid parallel to the plane of the tissue web. Further, the uncreped tissues show excellent wet resiliency and high bulk under load when wet.

The absorbent core 16 may also comprise free flowing absorbent materials such as fiber nits, particularly eucalyptus nits, formed by dispersing high-consistency pulp to entangle fibers into dense bundles. With added debonding agents, surfactants, lubricants, silicone compounds, or the like, substantially free-flowing nits can be formed with a desirable mean particle size less than about 1 mm, suitable for incorporation into an absorbent pocket in the absorbent core of articles of the present invention. Principles for the formation of nits and their incorporation into absorbent articles are disclosed in commonly owned copending application Ser. No. 60/129,746, "Absorbent Particles with Nits and Free-Flowing Particles," filed Apr. 16, 1999. Principles for combining nits with superabsorbent particles in absorbent articles are also disclosed in U.S. Pat. No. 5,800,417, "Absorbent Composition Comprising Hydrogel-Forming Polymeric Material and Fiber Bundles," issued to K. Goerg-Wood et al., Sept. 18, 1998. Discrete pockets of nits or other free-flowing particles in the absorbent core 16 can be formed by adhesively laminated two fibrous webs together with regions of adhesive material joining the webs.

Useful sources of cellulosic fibers include wood fibers, such as bleached kraft softwood or hardwood, high-yield wood fibers, and chemithermomechanical pulp fibers; bagasse; milkweed; wheat straw; kenaf; hemp; pineapple leaf fibers; or peat moss. High-yield fibers such as BCTMP can be flash-dried and compressed into dense pads which expand substantially when wetted. High-yield fiber pads that expand when wetted can be used for the absorbent cores of the present invention, as well as other expandable materials such as densified regenerated cellulose sponge materials, curled chemically stiffened cellulose fibers, and the like.

The absorbent capacity of the absorbent members can be optimized for the intended use of the article. For some uses, such as in sanitary napkins, it is desirable that the absorbent capacity of the central absorbent section 18 be at least 7 ml of fluid, specifically at least 10 ml, more specifically at least 16 ml, more specifically still at least 20 ml, and most specifically from about 15 ml to about 35 ml. In larger articles such as diapers, the absorbent capacity of the central absorbent member generally should be greater than 60 ml and can be about 300 ml or less of fluid, more specifically about 200 ml or less, more specifically still about 150 ml or less, with exemplary ranges of from about 80 ml to about 250 ml or from about 100 ml to about 300 ml.

For ultrathin pads and other absorbent articles, it is desirable that the dry components of the absorbent core 16 have a total thickness between about 2 mm and about 15 mm, and more specifically from about 3 mm to about 8 mm. When wetted, the central absorbent section 18 may increase substantially in thickness and void volume, such as a thickness increase of about 100% or greater, more specifically about 200% or greater, and more specifically still about 300% or greater. An example of a low-cost cellulosic component capable of increasing in thickness when wet is the absorbent material of Chen and Lindsay disclosed in U.S. Pat. No. 5,865,824, "Self-texturing Absorbent Structures and Absorbent Articles Made Therefrom," issued Feb. 2, 1999 to Fung-Jou Chen and J. D. Lindsay, or the densified structures of Hollenberg et al. in U.S. Pat. No. 5,779,860, "High-density Absorbent Structure," issued Jul. 14, 1998. Regenerated cellulose sponge materials are also capable of expanding significantly when wet and can be used to enhance body fit and conformability by providing the materials in nonuniform basis weights that expand in a three-dimensional shape. Densified cross-linked cellulosic mats can also be used.

Desirably, the AUL value (hereafter defined) of the absorbent material of the absorbent core 16 is about 10 grams/gram or greater.

Either the central absorbent member 18 or the outer absorbent member 22 or both, or individual plies thereof, may be embossed for improved control over fluid wicking, if desired. The absorbent members likewise may be apertured, slitted for improved flexibility and body conformability, perf-embossed, calendered, or pleated.

Dimensions of the components of the absorbent article 10 can be suited and optimized for particular functions. For feminine care pads, for example, the outer absorbent member 22 can have a transverse width (distance from one outer longitudinal side to the other across the transverse centerline, not the smaller edge width defined previously) of from about 4 cm to about 8 cm and a length of from about 15 cm to about 30 cm. The central void 66 in the outer absorbent member 22 may have a transverse width of from about 2 cm to about 6 cm, more specifically from about 3 cm to about 5 cm, and can have a length of from about 4 cm to about 30 cm, more specifically from about 6 cm to about 20 cm, resulting in a desirable distance from the longitudinal sides 46 of the central absorbent member 18 to the nearest outer longitudinal side of the outer absorbent member 22 (which can also be the edge width of the outer absorbent member 22, assuming no significant gap between the outer absorbent member 22 and the central absorbent member 18) of from about 0.3 cm to about 2.5 cm, and more specifically from about 0.5 cm to about 2 cm, and more specifically still from about 0.7 cm to about 1.5 cm. Appropriately larger dimensions would be desirable for diapers and many other absorbent articles. For example, the central absorbent member 18 may be from about 4 cm to about 10 cm in width in a diaper.

Basis weights of the components of the absorbent core can be adjusted and optimized for particular purposes over a wide range. Generally, it is desirable that the basis weight of the central absorbent member 18 be greater than the outer absorbent member 22 because the central absorbent member 18 is intended to contain the primary source of absorbent material for the article 10, and the outer absorbent member 22 can desirably function as a secondary source of absorbent material when the absorbent capacity of the central absorbent member 18 is exceeded. Thus, the basis weight of the central absorbent member 18 can range, for example, from about 100 grams per square meter (gsm) to about 2500 gsm, more specifically from about 200 gsm to about 1200 gsm, and more specifically still from about 300 gsm to about 800 gsm. The basis weight of the outer absorbent member 22 (or, in some embodiments, of the outer shaping member) can range from about 100 gsm to about 2000 gsm, more specifically from about 200 gsm to about 1000 gsm, and most specifically from about 200 gsm to about 600 gsm.

The central absorbent member 18 generally can be of any shape such as circular, elliptical, rectangular, triangular, polygonal, dog-bone shaped, hourglass shaped, or diamond shaped, and is inset or inserted into a void 66 in the outer absorbent member 22. The central absorbent member 18 can be substantially as long as the absorbent core 16, or can have a length ranging from about 10 mm to about 170 mm. Especially in embodiments where the longitudinal ends of the central absorbent member 18 are contained within a longer outer absorbent member 22, the length of the central absorbent member 18 can be from about 20 mm to about 140 mm, more specifically from about 40 mm to about 100 mm, and most specifically from about 60 mm to about 85 mm. The maximum width of the central absorbent member 18 can be 100% of the width of the absorbent article but desirably is no more than about 90%, more specifically no more than about 75%, and more specifically still no more than about 60% of the width of the absorbent article 10. The absorbent article 10 in target zone generally can have a width of about 20 mm or greater, more specifically about 40 mm or greater, and more specifically still about 60 mm or greater.

The topsheet 12 is liquid permeable and, when the article 10 is in use, is in close proximity to the skin of the user. Desirably, the topsheet 12 is compliant, soft and nonirritating to the user's skin. It can be made from any of the conventional materials for this type of use. Nonlimiting examples of suitable materials include woven and nonwoven polyester, polypropylene, nylon, rayon or the like, particularly in the form of formed or apertured thermoplastic films, including those described in U.S. Pat. No. 4,324,246 issued to Mullane and Smith on Apr. 13, 1982 and U.S. Pat. No. 4,342,314 issued to Radel and Thompson on Aug. 3, 1982. Mechanically apertured forms can also be used. Other known cover materials can be employed, including those made from textured cellulosic basesheets with hydrophobic matter added to selected portions of the basesheet, particularly the most elevated portions of the basesheet, as described in commonly owned copending U.S. application, "Dual-zoned Absorbent Webs", Ser. No. 08/997,287, filed Dec. 22, 1997.

The outer surface of topsheet 12 can be treated with a surfactant to improve liquid penetration, and can have gradients in wettability created having different chemical treatments on the two surfaces of the topsheet, such that fluid is preferentially absorbed in targeted intake regions and repelled by other regions.

Desirably, the inner surface of the topsheet 12 is secured in contacting relation to the absorbent core 16 such as by tensional forces, by ultrasonic or thermal bonding, by needling entanglement, or by application of adhesive. One or more optional tissue layers (not shown) may be disposed directly beneath the topsheet 12 to assist in fluid intake and suitably to restrain superabsorbent particles or other particles that may be present, as exemplified by the teachings of European Patent 652,736-B1, published Oct. 28, 1998.

The backsheet 14 is generally impervious to liquids and, thus, prevents menstrual fluid or other body exudates which may be released from the absorbent core 16 from soiling the body or clothing of the user. Any backsheet material used in the art for such purposes can be utilized herein. Suitable materials are embossed or nonembossed polyethylene films and laminated tissue, desirably treated with sizing agents and wet strength agents. Breathable films that permit moisture transpiration to occur without significant condensation can also be used. The backsheet 14 may be embossed or provided with odor-controlling materials or provided with microencapsulated materials for skin wellness or release of anti-microbial or anti-odor agents upon wetting. The backsheet 14 may also be made of a soft, cloth-like material which is hydrophobic relative to the topsheet 12. An exemplary cloth-like backsheet material is a laminate of a polyester nonwoven material and a film such as is described in U.S. Pat. No. 4,476,180 issued to Wnuk on Oct. 9, 1984. Desirably, the backsheet is a polyethylene film having a thickness of from about 0.012 mm to about 0.051 mm. The backsheet 14 and other components may be biodegradable and/or flushable.

FIG. 2 depicts a cross-section the sanitary napkin 10 of FIG. 1 taken near the transverse centerline. The topsheet 12 is joined to the backsheet 14 with adhesive 56 or other connection means near the longitudinal sides of the article 10. In the embodiment shown, the wicking barrier 24 passes beneath the central absorbent member 18 and has a vertical component 28 extending vertically from beneath the central absorbent member 18 to the surface of the outer absorbent member 22, where it extends horizontally to define a horizontal component 26 or ledge on the surface of the absorbent core 16. Here the horizontal component 26 (or ledge) in the target zone 48 substantially covers the outer absorbent member 22, while traversing a smaller distance outside of the target zone 48, as shown in FIG. 1. When the horizontal component 26 covers only a fraction of the distance between the longitudinal sides of the central absorbent member 18 and the longitudinal sides of the outer absorbent member 22, the horizontal distance spanned by horizontal component 26 can be, by way of example, between about 0.3 millimeters (mm) and about 5 mm, and specifically between about 0.5 mm and about 3 mm, more specifically between about 1 mm and about 2.5 mm, and alternatively between about 0.2 mm and about 2 mm.

The central rising member 30 here is an "e"-folded section of flexible material, such as a densified airlaid web, capable of deflecting upwards when compressed from the sides. The central rising member 30 is above the wicking barrier 24, but can also be beneath the wicking barrier 24. In other embodiments, the central rising member 30 may reside within the central absorbent member 18, having absorbent material above and below.

The central rising member 30 can be a flexible absorbent material such as densified airlaid webs comprising pulp fibers and thermoplastic binder particles, coform, or one or more layers of creped or uncreped tissue. Many other materials can be used to construct a central rising member. Moldable foams can be used, such as a polyethylene foam sheet creased or scored to provide bending lines therein. Other suitable foams are made from such substances as polyethylene, polypropylene, polybutylene, ethylene vinyl acetate, polyurethane, thermobondable cellulose, silicone elastomerics and others. The central rising member 30 can also be made of various fibers, films or sheets of polymeric material, heavy-weight paper such as cardboard, or a combination or laminate of these or other materials. However, in many embodiments it is desirable that the central rising member 30 be substantially absorbent and more specifically comprise at least 50% by weight of cellulosic fibers.

Desirably, the central portion of the absorbent article 10 is substantially free of non-absorbent elements, apart from the topsheet 12, the backsheet 14, an optional baffle layer or wicking barrier 24 beneath the central absorbent member 18, and a small quantity of adhesive for product attachment and integrity. Thus, in a preferred embodiment, the central rising member 30 comprises absorbent materials, such that at least 50% of the mass of the central rising member is absorbent, and more specifically substantially all of the central rising member is absorbent or hydrophilic.

Figure 3:
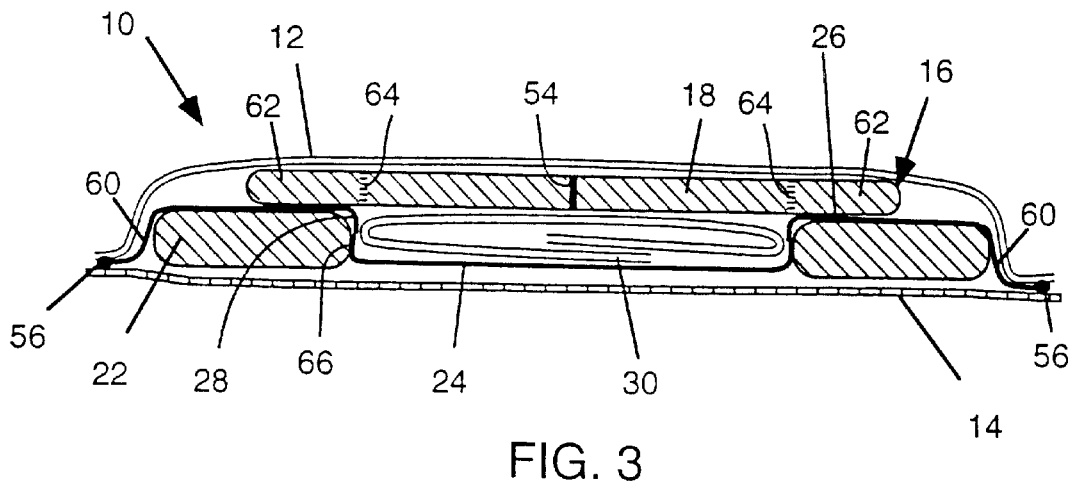
FIG. 3 depicts a cross-section of a sanitary napkin wherein the central absorbent member overlaps a portion of the outer absorbent member.

FIG. 3 is a cross-section of an embodiment similar to that of FIG. 2. In FIG. 3, the central rising member 30 occupies much of the space within the central void 66 within the outer absorbent member 22, such that the central absorbent member 18 does not necessarily descend into the central void 66. End portions 62 of the central absorbent member 18 extend past the boundary of the central void 66 and overlap the outer absorbent member 22, but do not extend to the longitudinal sides of the outer absorbent member 22 and do not extend past the longitudinal sides of the wicking barrier 24, such that a protective zone defined by the longitudinal sides of the wicking barrier 24 and the longitudinal sides of the outer absorbent member 22 surround the central absorbent member 18. The central absorbent member 18 is further provided with substantially longitudinal crease lines 64 disposed over the longitudinal sides of the central rising member 30 (or near the longitudinal walls of the central void in the outer absorbent member 22), such that the crease lines 64 naturally promote effective downward folding of the absorbent core of the article 10, while the central rising member 30 and the shaping line 54 in the central absorbent member 18 promote upward deflection of the central portion of the central absorbent member 18 during lateral compression. The wicking barrier 24 extends past the longitudinal sides of the outer absorbent member 22 and joins the periphery of the article 10, where it can be attached by adhesive 56 or other means to the backsheet 14 and topsheet 12.

The absorbent core 16 has a step change in thickness in the region laterally outward of the central void 66. At the longitudinal sides of the outer absorbent member 22, the absorbent material of the absorbent core 16 has a first thickness representing the thickness of the outer absorbent member 22. Moving transversely inward, the absorbent material of the absorbent core 16 experiences a step increase in thickness to a second thickness equal to the combined thickness of the outer absorbent member 22 and the central absorbent member 18. There is likewise a step change in basis weight. Moving further inward, a second step change in thickness or basis weight can be experienced upon encountering the region over the central rising member 30.

The configuration of the central absorbent member 18 overlapping a portion of the outer absorbent member 22 provides a restraint to urge the longitudinal sides of the outer absorbent member 22 back toward a horizontal orientation when inwardly lateral compressive forces are relaxed or relieved after having been flexed upwards by inwardly lateral compressive forces, such as by the legs of the user. In other words, the presence of the extended ledge of absorbent material from the end portions 62 of the central absorbent member 18 overlapping the outer absorbent member 22 helps to improve the mechanical properties of the article 10, giving it a more elastic or "springy" nature to help it adjust and conform to the body in a variety of positions without having excessive stiffness. Flexure regions are provided by the break between the central rising member 30 and the outer absorbent member 22, coupled with crease lines 64 in the overlying outer absorbent member 22, and a flexure region is also provided by the shaping line 54 in the central absorbent member 18, such that the absorbent core 16 readily conforms to the body without excessive stiffness, and such that a W-shape in the target zone 48 can be established, but the article 10 is not "dead" or devoid of elastic properties that allow the article 10 to flex back into a horizontal position when compressive forces are relaxed. The restraint offered by the extended central absorbent member 18 (i.e., by the longitudinal sides of the central absorbent member 18 which overlap a portion of the outer absorbent member 22) plays a useful role in providing excellent elastic and other mechanical properties of the article 10 when worn. Nevertheless, laterally outward of the central absorbent member 18 is still a protective region of a wicking barrier 24 superposed on the body-side surface of the outer absorbent member 22, which prevents lateral wicking of body fluids from the central absorbent member 18 to the longitudinal sides of the outer absorbent member 22 and which provides a clean, dry zone surrounding the central absorbent member 18. Excellent aesthetic and fluid handling properties are thereby achieved.

Figure 4:
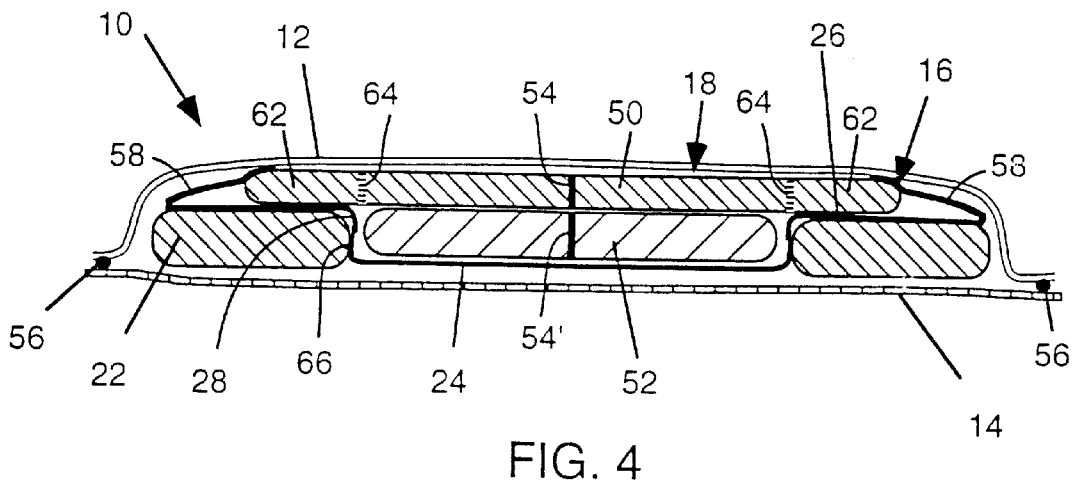
FIG. 4 depicts a cross-section of a sanitary napkin wherein the wicking barrier forms a cuff along the longitudinal sides of the central absorbent member, central rising member.

FIG. 4 resembles FIG. 3 except that the wicking barrier 24 has been modified (described hereafter) and the former "e"-folded central rising member 30 has been replaced with a lower absorbent layer 52 (e.g., an absorbent pledget, though an absorbent central rising member could be used as well), and the central absorbent member 18 is now a multilayered central absorbent member 18 comprising a lower absorbent layer 52 and an upper absorbent layer 50 with longitudinal end portions 62 that overlap the outer absorbent member 22. The lower absorbent layer 52 is also provided with a shaping line 54'. As depicted, the lower absorbent layer 52 has a thickness similar to that of the outer absorbent member 22. In a related embodiment wherein the lower absorbent layer 52 is thicker than the outer absorbent member 22, the upper absorbent layer 50 will be held in a concave upward shape prior to use and will be naturally predisposed to flex upward upon lateral compression, often without a need for a shaping line therein. In any case, the interaction of lower absorbent layer 52 with the upper absorbent layer 50 and the optional shaping lines 54, 54' provides an integral absorbent central rising member within the central absorbent member 18.

Figure 5:
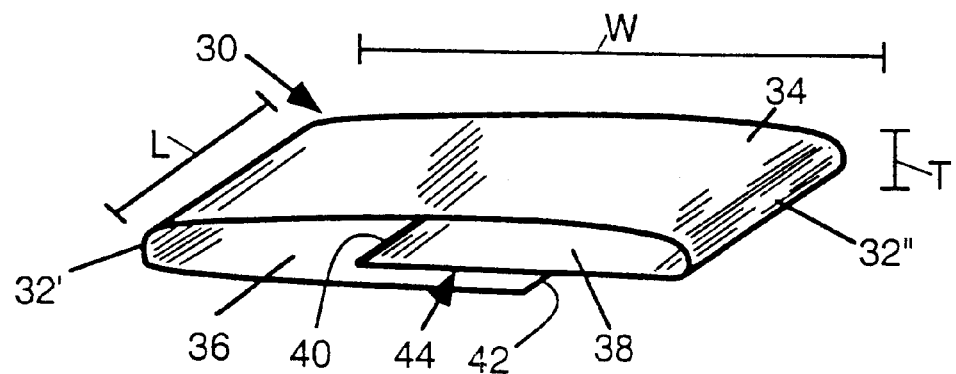
FIG. 5 depicts an "e"-folded central rising member.

FIG. 5 is a perspective view of an "e"-folded central rising member 30. The central rising member 30 comprises a sheet of material that is folded or wrapped to have two longitudinal sides 32', 32", an upper portion 34, a first lower portion 36 and a second lower portion 38, each of which terminate respectively into ends 40, 42. The terminal portions of the lower portions 36, 38 overlap in an overlapping region 44. The two lower portions 36, 38 in the overlapping region 44 may be free to slide past each other or may be joined in a fixed relationship to prevent sliding of one lower portion relative to the other. In the embodiment shown, the lower portions 36, 38 are freely slideable relative to one another.

Preferably, the upper portion 34 of the "e"-folded central rising member 30 is toward the body side of the absorbent article (toward the topsheet) and the lower portions 36, 38 are toward the garment side of the article in order to obtain the best deformation of the central rising member 30 toward the body side of the user when the article is worn and compressed laterally inward.

The material forming the central rising member 30 is shown here as folded roughly into the shape of a compressed letter "e", with the lower portion 38 corresponding to the central crossbar of an "e" that extends across only a portion of the width of the "e". In other words, the folded shape of the central rising member 30 resembles a section of material folded into a tube with overlapping ends 40, 42 in an overlapping region 44, the tube being vertically compressed to be substantially flat. When laterally compressed, the lower portions of the folded material 36,38 that terminate into overlapping ends 40, 42 can mutually slide toward the opposing longitudinal side of the article. Specifically, the end 40 of the second lower portion 38 slides toward the first longitudinal side 32', while the end 42 of the first lower portion 36 may slide toward the second longitudinal side 32" or can remain substantially immobile or fixed to underlying sections of the absorbent article. During such deformation, the upper portion 34 deflects upward.

The central rising member 30 has a transverse width W, a longitudinal length L, and a z-direction thickness T. The width W of the central rising member 30 in the absorbent article prior to use can be equal to or less than the minimum width of the absorbent article in the target zone. Specifically, the width W of the central rising member 30 can be about 90% or less, more specifically about 70% or less, more specifically still about 50% or less of the minimum width of the absorbent core in the target zone of the absorbent article. Without limitation, dimensions of width W, thickness, T, and length L for a central rising member 30 suitable for a sanitary napkin and related absorbent articles can include the following, given for the article in its unused, uncompressed state: for width W, from about 10 mm to about 60 mm, more specifically from about 15 mm to about 40 mm; for thickness T, from about 1 mm to about 15 mm, more specifically from about 3 mm to about 8 mm; for length L, from about 10 mm to about 100 mm, more specifically from about 15 mm to about 70 mm, and most specifically from about 20 mm to about 50 mm.

Figure 6:
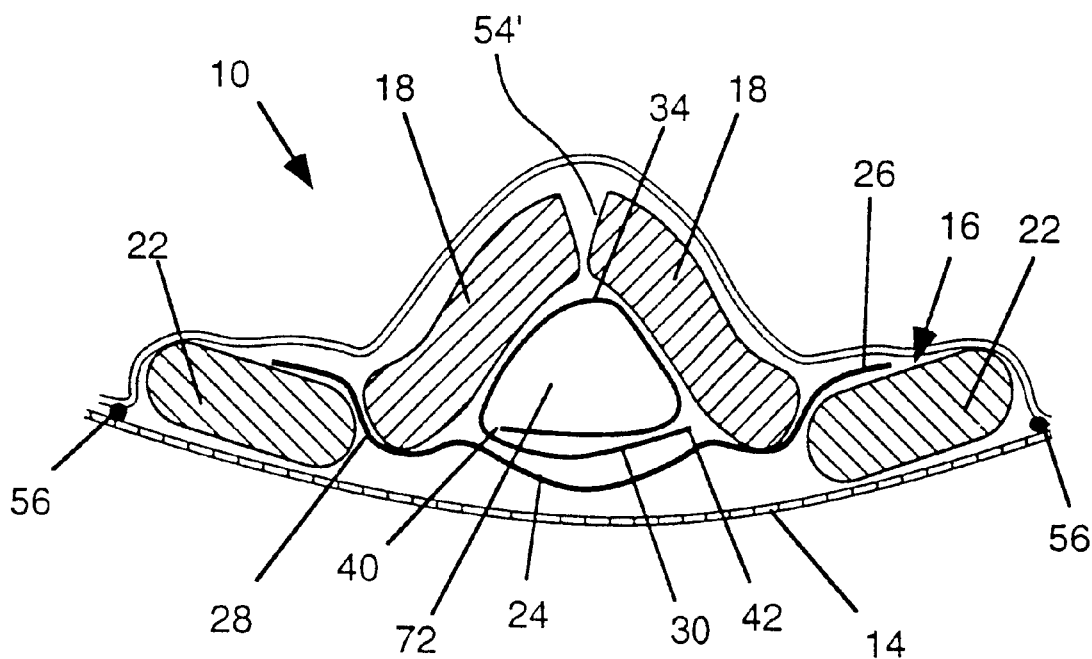
FIG. 6 depicts a cross-section of the sanitary napkin of FIG. 1 after being subjected to lateral compression.

FIG. 6 depicts the absorbent article 10 of FIGS. 1 and 2 after lateral compression, where the central rising member 30 has deflected the overlying central absorbent member 18 vertically upward. The ends 40, 42 of the central rising member 30 have moved toward the opposing longitudinal sides thereof as the upper portion 34 has deflected upward, resulting in formation of a void space 72 beneath the central absorbent member 18 and specifically within the central rising member 30.

Desirably, the horizontal component 26 of wicking barrier 24 is adhesively attached to the outer absorbent member 22, and the vertical component 28 of wicking barrier 24 is adhesively attached to the longitudinal sides of the central absorbent member 18, to provide a restraint to deform the absorbent article 10 back toward a relatively flatter state upon release of lateral compressive forces, whereby the absorbent article 10 can readjust to the body during changes in body position. It is generally not preferred that the longitudinal sides of the article 10 be easily deformable with no tendency to spring back or return to the original shape, but it is preferred that restraint means be present in the article 10. An additional layer of resilient materials such as a foam or sufficiently thick absorbent fibrous web (e.g., a thickness of about 1 mm or greater with a basis weight of about 100 gsm or greater) may be disposed below the lower absorbent member to span the width of the target zone to provide a restraint for urging the longitudinal sides of the article back toward a flat position when compressive forces are relieved. Deformable thermoplastic elements or rubber layers or elastomeric reinforcements may also be present to serve as restraint means.

Figure 7A:
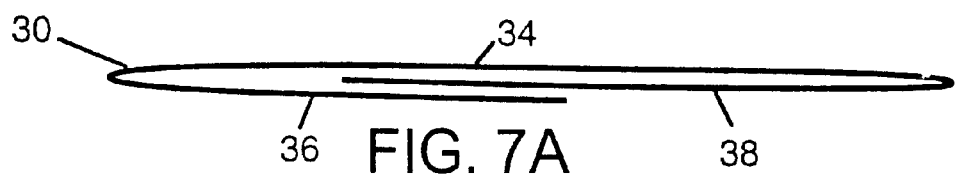
FIGS. 7A–7F depict a central rising member in various stages of lateral compression.
Figure 7B:
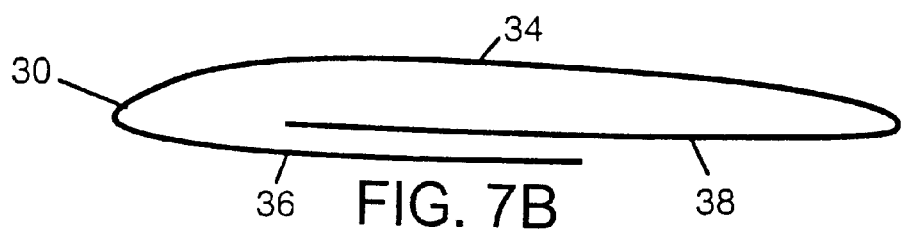
Figure 7C:
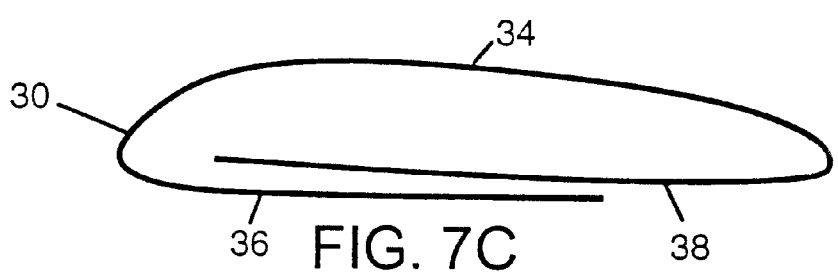
Figure 7D:
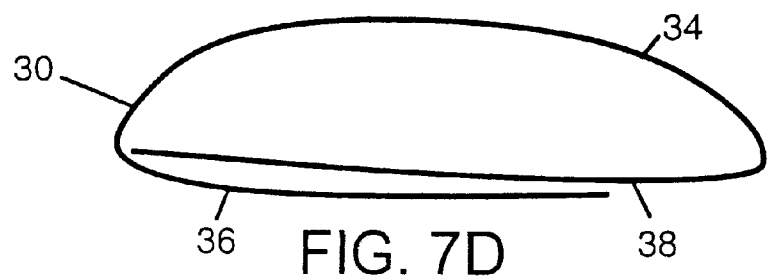
Figure 7E:
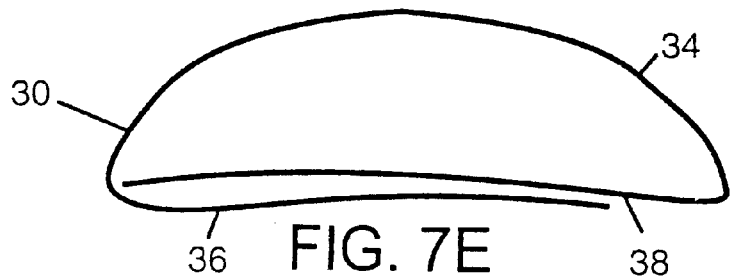
Figure 7F:
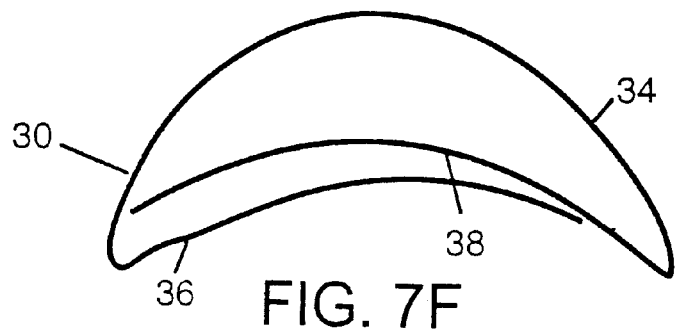

FIGS. 7A–7F depict the central rising member 30 in several states of deformation, beginning in FIG. 7A with a vertically compressed central rising member 30 under little or no lateral compression, with successively greater degrees of lateral compression and vertical deflection being displayed in FIGS. 7B through 7F. The central rising member 30 in FIG. 7F is sufficiently deformed laterally that even the lower portions 36, 38 of the folded material have deflected upward.

Figure 8:
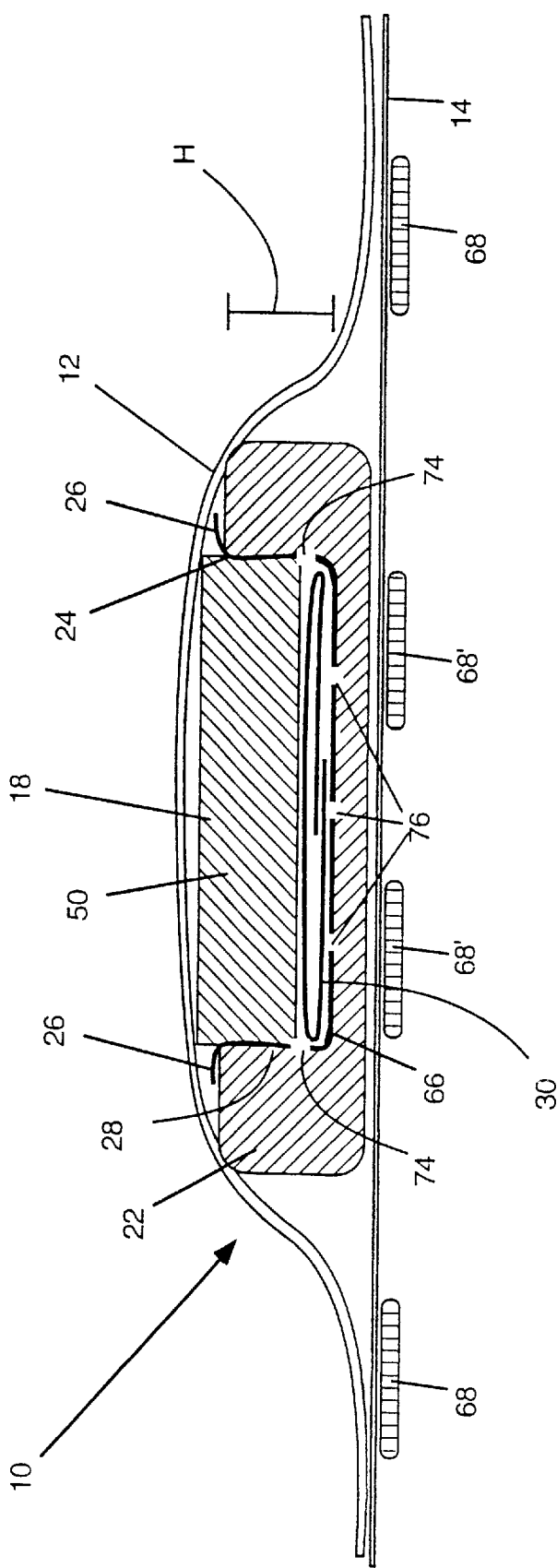
FIG. 8 depicts a sanitary napkin according to the present invention in which the outer absorbent member extends beneath the central absorbent member.

FIG. 8 is a cross-section of a related embodiment. The outer absorbent member 22 has a region of reduced basis weight or thickness having a surface which defines the boundary of a central void 66. The wicking barrier 24 spans a vertical distance H between the elevation of the body-side surface of the outer absorbent member 22 and the elevation of the lowest portion of the surface of the central void 66 in the outer absorbent member 22. H can be from about 1 mm to about 10 mm, more specifically from about 1 mm to about 5 mm, and more specifically still from about 2 mm to about 4 mm.

Flow of fluid from the central absorbent member 18 to the outer absorbent member 22 is made possible by the presence of optional apertures or openings 72, 74 in the wicking barrier 24 remote from the body-side surface of the article. It is intended that body fluid will primarily enter the absorbent article in or immediately above the central absorbent member 18, passing through topsheet 12 into the central absorbent member 18. If fluid spreads radially from the central absorbent member 18 to the outer absorbent member 22, it is intended that such movement of fluid will occur by a tortuous pathway rather than by directly wicking from the body-side surface of the central absorbent member 18 to the body-side surface of the outer absorbent member 22. A tortuous path is established by the optional apertures or openings 72, 74 in the wicking barrier 25 such that fluid entering the central absorbent member 18 must first migrate downward into the central absorbent member 18 through the openings in the wicking barrier 24 and from thence into the radially outward sections of the outer absorbent member 22, still submerged beneath the body-side surface of the outer absorbent member 22. The depth, size, and number of the openings 72, 74 can be adjusted to provide the proper balance between hindering radially outward or lateral flow toward the edges of the article and preventing oversaturation or overflowing of fluid from the central absorbent member 18. No openings are needed if the absorbent capacity of the central absorbent member 18 is adequate for the anticipated fluid loadings the absorbent article 10 will receive.

The horizontal component 26 of the wicking barrier 24 resides primarily on the body-side surface of the outer absorbent member 22. However, the horizontal component 26 may also be configured to extend along a portion of the body-surface of the central absorbent member 18 either in addition to or instead of residing on a portion of the surface of the outer absorbent member 22.

The outer surface of backsheet 14 can be coated with adhesive such as the pressure-sensitive adhesive strips 68,68'. The adhesive, for example, can provide a means for securing the pad in the crotch portion of a panty. Any adhesive or glue used in the art for such purposes can be used herein, with pressure sensitive adhesives being preferred. Also, before the article 10 is placed in use, the pressure sensitive adhesive should be covered with one or more removable release liners (not shown). Any commercially available release liners commonly used for such purposes can be utilized.

Figure 9:
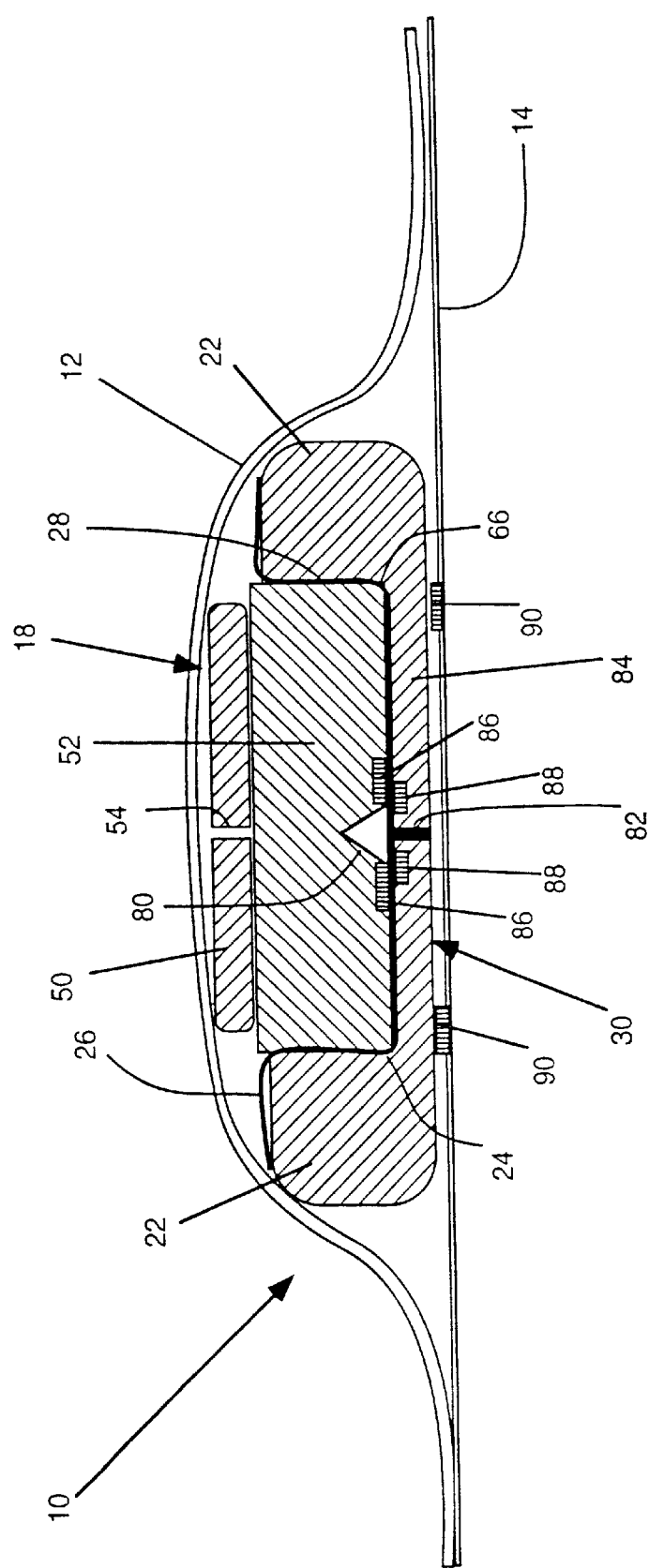
FIG. 9 depicts a cross-section of a sanitary napkin with a central rising member that is integral with the outer absorbent member.

FIG. 9 depicts the cross-section near the transverse centerline of a related absorbent article 10 according to the present invention. The central absorbent member 18 has an upper layer 50 and a lower layer 52. The upper layer 50 is thinner and narrower than the lower layer 52. The lower layer 52 is provided with a scoremark 80 to serve as a shaping line, permitting and preferably promoting upward flexure of the central absorbent member 18 during lateral compression. Preferably, the scoremark 80 is a deformation or crease in the lower layer 52 formed by a sharp upward fold made prior to assembling the article 10. Such a scoremark 80 is generally accompanied by delamination of the material on the side of the layer opposite the scoremark, causing a slightly elevated region (not shown). Alternatively, the scoremark 80 can be a notch created by removal of material in the lower layer 52, wherein the notch penetrates at least about 20% of the layer thickness and preferably at least about 40% of the layer thickness. The upper layer 50 of the central absorbent member 18 is also provided with a shaping line 82, depicted here as a slit or gap extending in the longitudinal direction.

A central portion 84 of the outer absorbent member 22 spans a region including the longitudinal centerline and forms a floor beneath the central void 66. This central portion 84 may be a densified region having substantially the same basis weight as the other portions of the outer absorbent member 22, or can have substantially the same density but a lower basis weight, or may differ in basis weight and density. Further, the central portion 84 may differ in other material properties, particularly stiffness, for it is desirable that it have a higher stiffness per unit thickness than the more outward portions of the central absorbent member 22 in order that the central portion 22 can cooperate with other components to function as an integral central rising member 30. Desirably, the central portion 84 of the outer absorbent member 22 comprises a shaping line 82 (a shaping line for upward folding) near the longitudinal centerline and desirably immediately beneath the scoremark 80.

The wicking barrier 24 is joined to a portion of the lower layer 52 of the central absorbent member 18 by adhesive strips 86 or other attachment means near the central scoremark 80, which is desirably on the longitudinal centerline of the absorbent article 10 and preferably extends longitudinally throughout the target zone. The wicking barrier 24 is further attached by adhesive means 88 or other means to the middle of the central portion 84 of the outer absorbent member 22 that resides beneath the central absorbent member 18, with attachment occurring on or near the longitudinal centerline. The central portion 84 in turn is attached to the backsheet 14 by attachments 90, such as adhesive strips, near the longitudinal sides of the central void 66.

During lateral compression from the longitudinal sides of the article 10, the scoremark 85 creates a tendency for the lower layer 52 to deflect upward, which in turn helps ensure that the deflection of the underlying central portion 84 of the outer absorbent member 22 will be upward, due to the linkage between those components created by the attachments 86, 88, 90.

In the embodiment shown, the central rising member 30 beneath the central absorbent member 18 is integral with other components of the article 10. The integral central rising member 30 thus comprises the central portion 84 of the outer absorbent member 22, the portion of the wicking barrier 24 underneath the lower layer 52 of the central absorbent member 18; and adhesive strips or other attachments 86, 88, 90.

Figure 10:
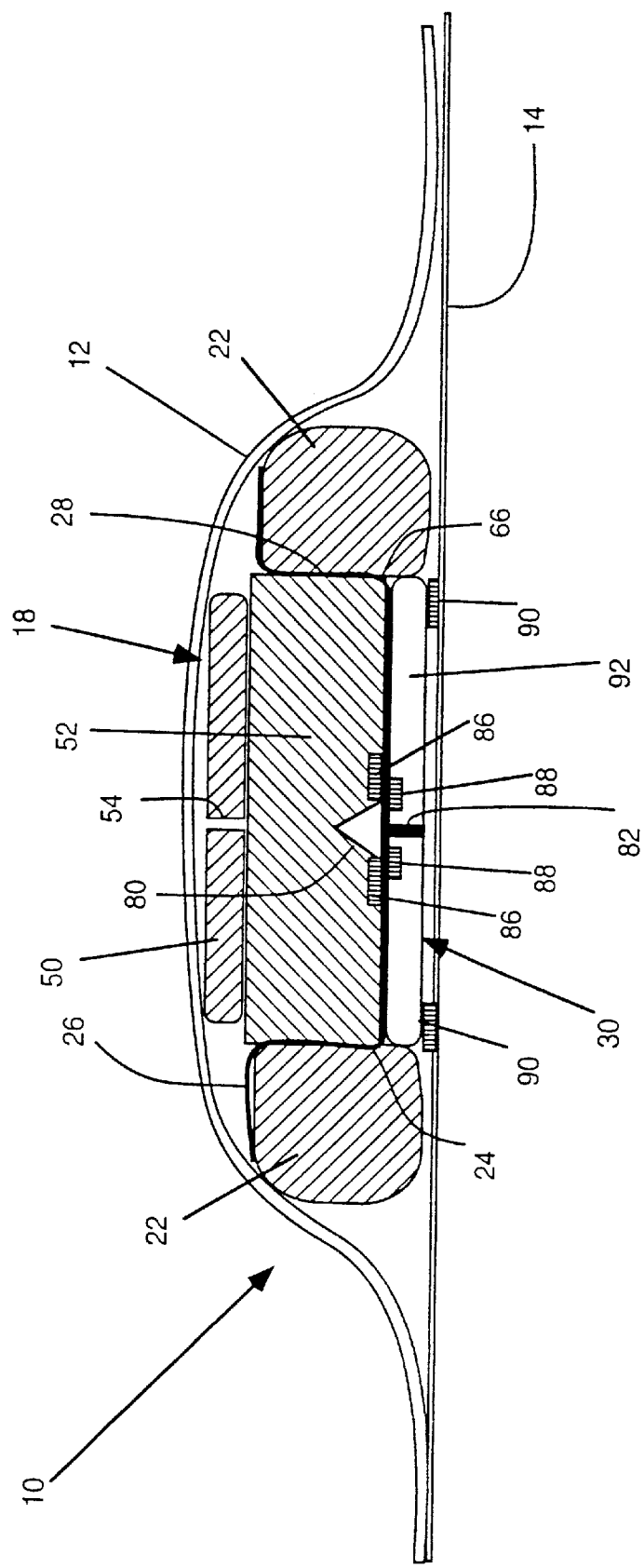
FIG. 10 depicts a cross-section of an absorbent article with a central rising member beneath a central absorbent member, the central absorbent member having a notch therein.

FIG. 10 shows a related embodiment based on FIG. 9, but wherein the central portion 84 of the outer absorbent member 22 in FIG. 9 is now replaced with a separate flexure component 92 having a longitudinally central hinge or shaping line 82 for upward folding. The flexure component 92 can be a densified airlaid material, wet laid tissue, paperboard, a stiff nonwoven web, a plastic section, or other resilient materials capable of forming an inverted V-shape when the longitudinal sides of the flexure component 92 are mutually pushed together in the plane of the flexure component toward the longitudinal centerline thereof. The flexure component 92 is attached to the wicking barrier 24 by optional adhesive deposits 88 or other bonding or joining means and optionally secured near its longitudinal sides to the backsheet 14 with additional adhesive deposits 90 or other bonding or joining means.

Since the flexure component 82 is separate from the outer absorbent member 22, the central rising member 30 is not considered to be an integral central rising member. The central rising member 30 comprises the flexure component 82 with a central hinge or shaping line 82, acting in cooperating relationship with the central absorbent member 18 and other components.

Figure 11:
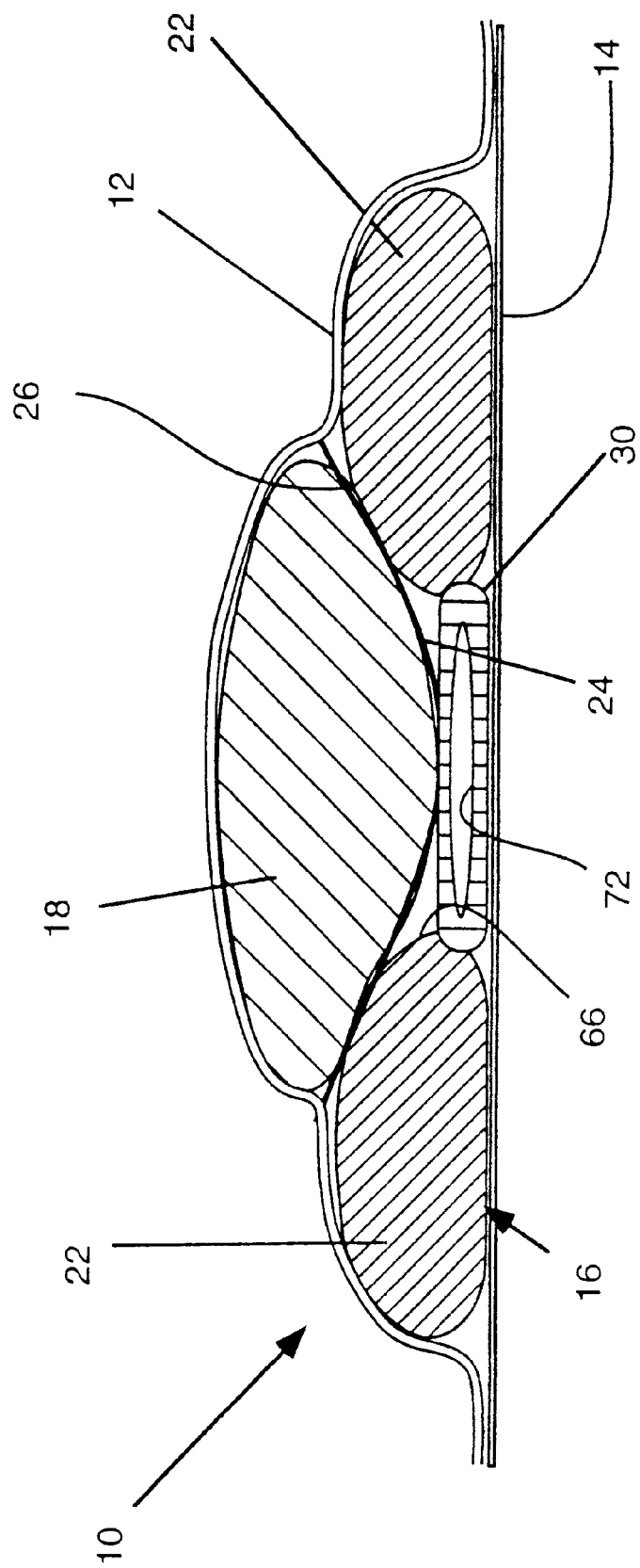
FIG. 11 depicts a cross-section of an absorbent article with tube-like central rising member.

FIG. 11 depicts a transverse cross-section of another absorbent article 10 according to the present invention. The absorbent core 16 comprises an outer absorbent member 22 (or, alternatively, an outer shaping member) which is divided into two sections along the cross-section shown to define a central void 66 which receives a central absorbent member 18. The wicking barrier 24 has a horizontal component 26 (spanning a horizontal distance on the surface of the outer absorbent member 22, even though the wicking barrier 24 does not necessarily lie in a horizontal plane). The wicking barrier 24 also spans a finite vertical distance from its nadir near the longitudinal centerline to its zenith above the outer absorbent member 22.

Situated within the central void 66 is a central rising member 30 depicted here in the form of a flattened tube of flexible material whose walls define an internal void space 72 which increases in size upon lateral compression by the legs of a wearer.

Figure 12:
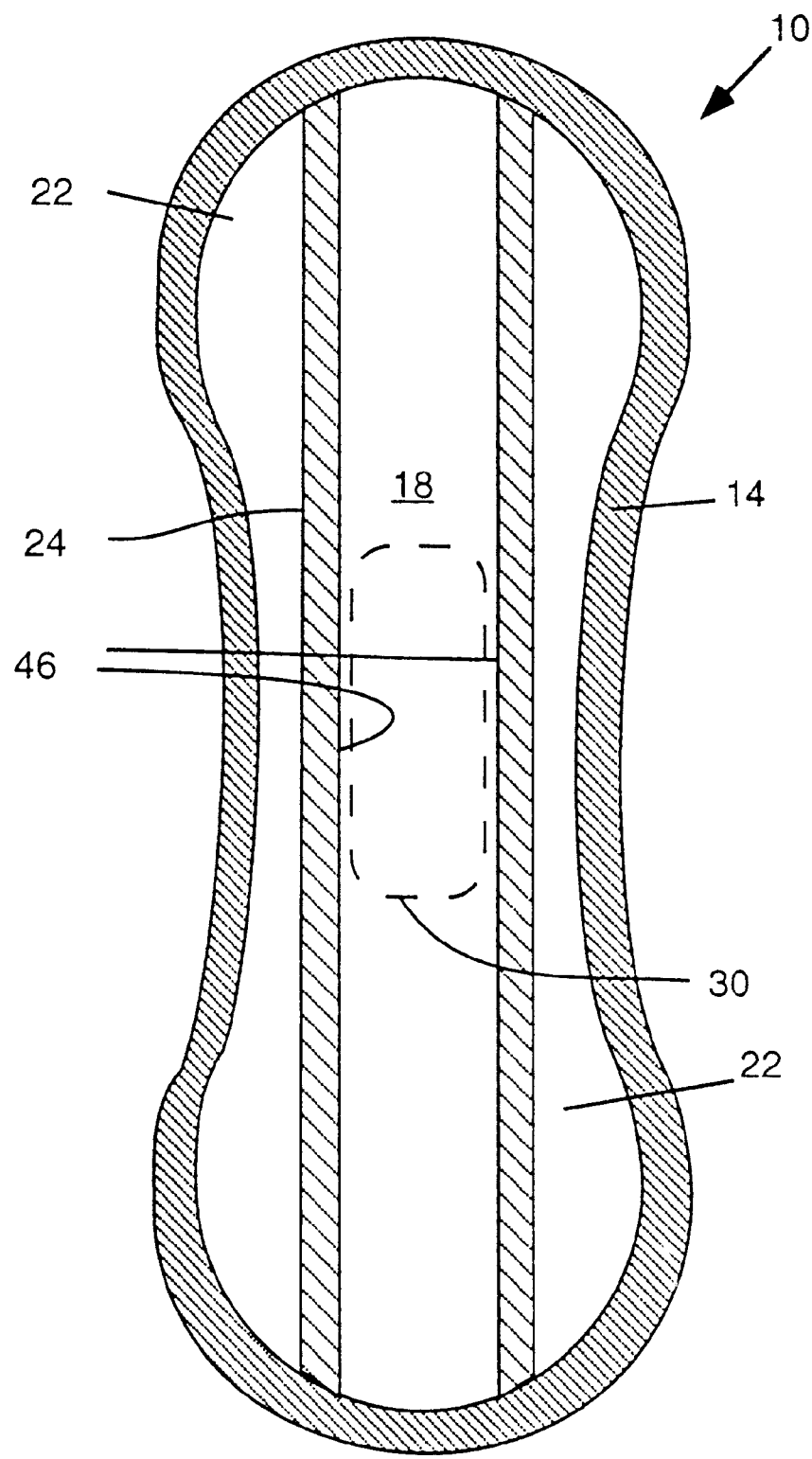
FIG. 12 is a top view of a sanitary napkin having a central absorbent member separated from the outer absorbent member by a wicking barrier forming longitudinal bands.

FIG. 12 provides an example of an article 10 in which the wicking barrier 24 prevents lateral wicking to the longitudinal sides of the article without the wicking barrier 24 forming a complete loop around the central absorbent member 18 (here the topsheet is not shown for clarity). Here the outer absorbent member 22 comprises two separate strips surrounding the central absorbent member 18 with the wicking barrier 24 therebetween. The longitudinal sides 46 of the central absorbent member 18 may be straight, as depicted, or curved. The wicking barrier 24 may be unitary or may comprise two discontiguous bands of barrier material.

Figure 13:
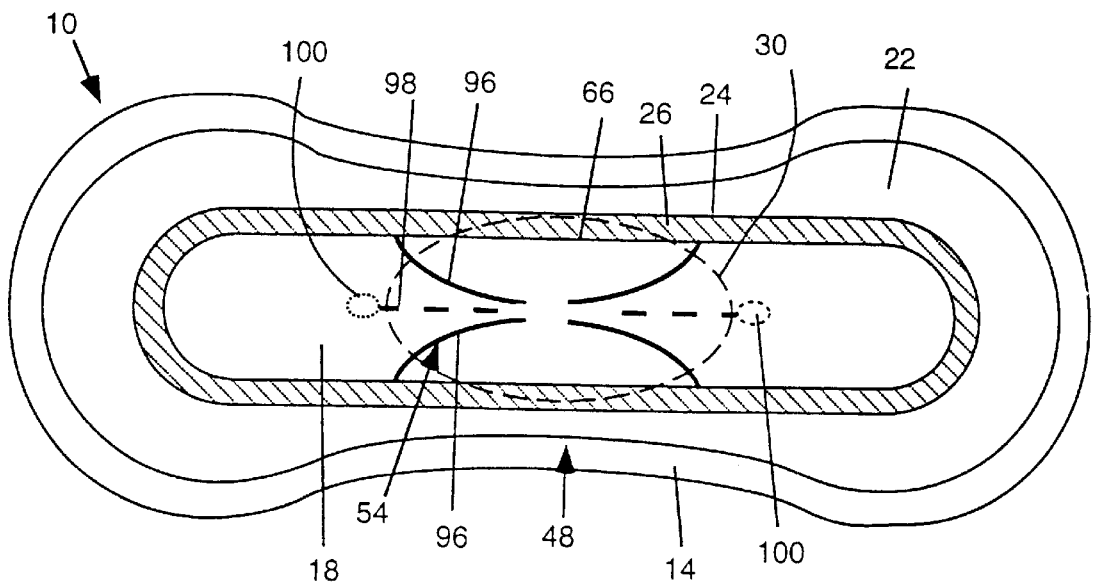
FIG. 13 is a top view of a sanitary napkin having bending lines in the central absorbent member and attachment points to guide deflection of the article in the longitudinal direction.

FIG. 13 depicts a top view of a sanitary napkin 10 according to the present invention. The central absorbent member 18 comprises a shaping line 54 comprising outwardly concave arcs 96 and a central longitudinal line 98, which may be a series of perforations, notches, cuts, tears, or slits having portions not fully perforated, notched, cut, torn, or slit along its length for increased integrity. Likewise, the arcs 96 can be, for example, slits but desirably should not completely sever a portion of the central absorbent member 18. When the article 10 is laterally compressed, not only does the central rising member 30 urge the central absorbent member 18 upward, but the interaction of the shaping line 54 with the deflection of other members allows a mountain-like structure to rise in the central absorbent member 18. The curvature of the central absorbent member 18 along the longitudinal centerline of the article (the longitudinal axis passing through the center of the article in the plane thereof, which in this case includes the central longitudinal line 98) can be beneficially controlled by forming attachment regions 100, wherein the central absorbent member 18 is connected adhesively (achievable by chemical adhesives, ultrasonic bonding, thermal bonding, etc.) or mechanically (e.g., by sewing, or by fiber entanglement from needling or embossing) to the backsheet 14 to prevent significant upward deflection in that region and to encourage upward curl of the transverse ends of the article with respect to the longitudinal centerline. The attachment regions 100 are located on or near the longitudinal centerline of the article 10 and are located roughly outside the target zone 48. Thus, when the article 10 is compressed laterally, the article 10 can more easily assume an upwardly curved shape along the longitudinal centerline and a W-fold shape in the target zone 48, substantially without a W-fold shape outside the crotch region 38.

Figure 14:
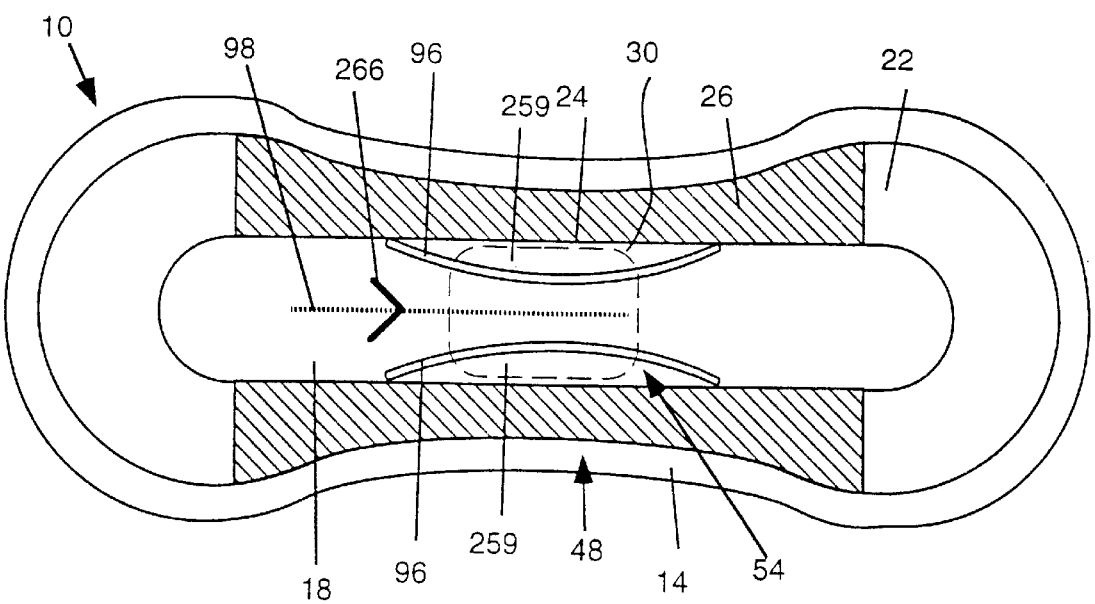
FIG. 14 is a top view of a sanitary napkin having bending lines in the central absorbent member and an extended wicking barrier in the target zone (the crotch region).

FIG. 14 depicts a top view of an absorbent article 10 similar in construction to that of FIG. 13, but wherein the wicking barrier 24 does not completely encircle the central absorbent member 18 but provides separation between the outer absorbent member 22 and the central absorbent member 18 in the target zone 48 and somewhat beyond. In effect, the 1d boundary in the target zone 48 between the outer absorbent member 22 and the central absorbent member 18 is a crease line that promoted downward folding (valley folds), which enhances the W-shape form in the target zone 48 as the shaping line 54 in the central absorbent member 18 in combination with the central rising member 30 urge deformation to an inverted-V shape in the central absorbent member 18 during lateral compression of the article 10 from the longitudinal sides thereof toward the longitudinal centerline.

Figure 15:
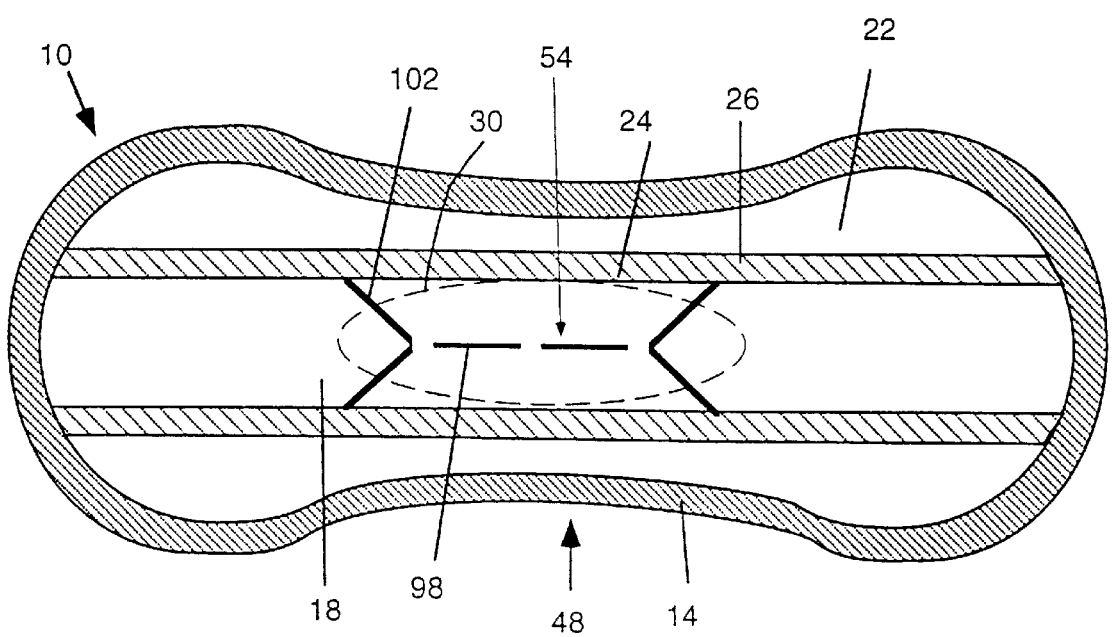
FIG. 15 is a top view of a sanitary napkin having bending lines in the central absorbent member.

FIG. 15 depicts the top view of a sanitary napkin 10 having outer absorbent member 22 split longitudinally into two zones, also having a central absorbent member 18 provided with a shaping line 54 that interacts with the underlying central rising member 30 for good body fit when laterally compressed. The shaping line 54 comprises a central longitudinal line 98 and a pair of outwardly spanning lines 102.

Figure 16:
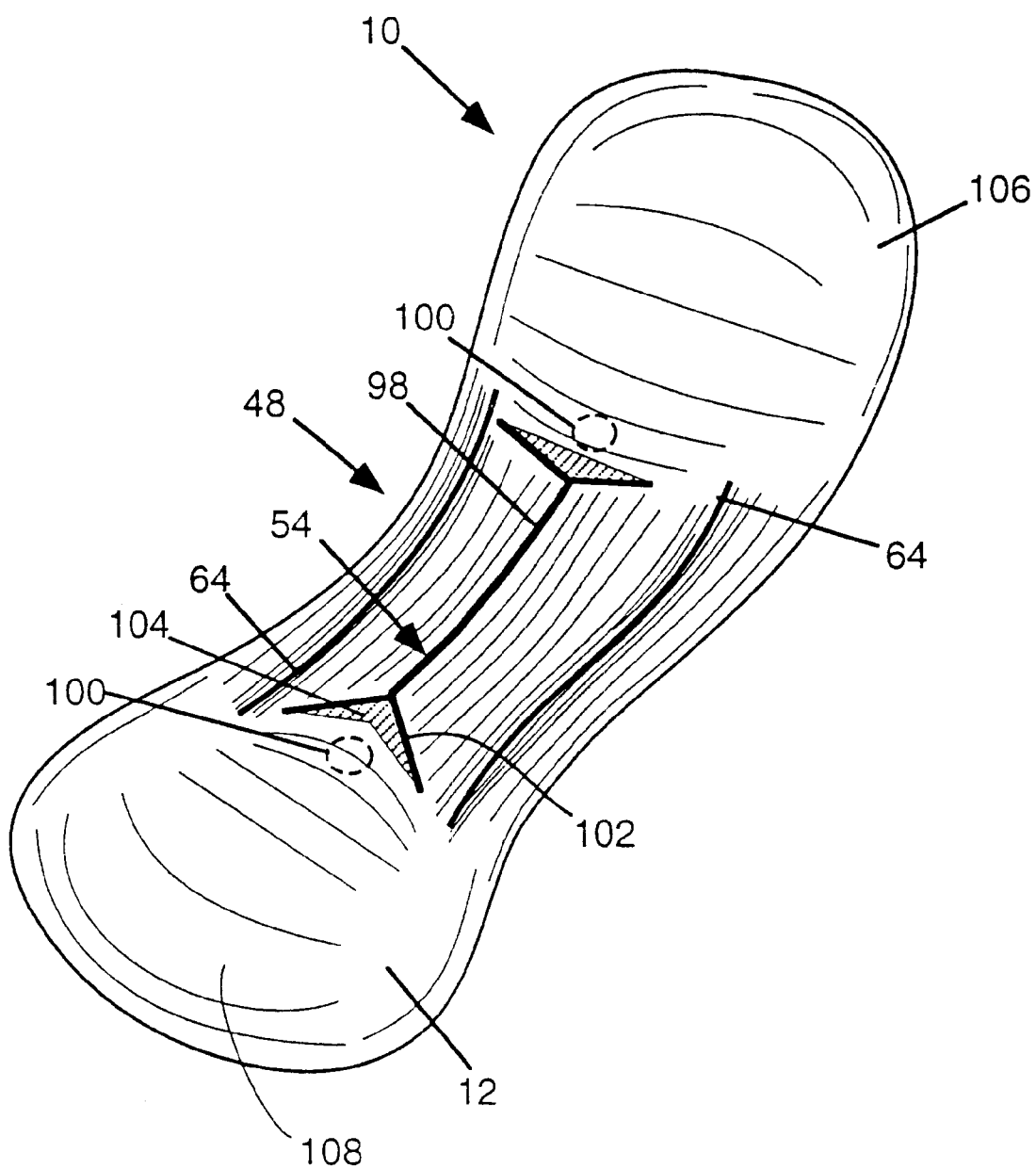
FIG. 16 shows a feminine care pad after a degree of lateral compression.

FIG. 16 shows the topography of a sanitary napkin 10 similar to the that of FIG. 15, but under lateral compression in the crotch region 48. Internal structural components such as the central rising member and the wicking barrier are not shown, and the boundary between the outer absorbent member and central absorbent member is also not shown to emphasize the topography of the upper surface which is covered with a topsheet 12. Crease lines 64 and the shaping line 54 are shown. The shaping line 54 comprises a longitudinal line 98 such as a slit or notch or groove and symmetric pairs of outwardly spanning lines 102 which comprise slits. In the crotch region 48, a W-fold geometry is achieved as a valley is formed about the crease lines 64 and an inverted-V shape is induced by the shaping line 54, which includes a central longitudinal line 98 and outwardly spanning lines 102 (oblique components) which, as depicted here, are slits that permit formation of a gap 104 under the inverted V-shaped region. The slits also partially disengage the crotch region 48 from the front region 106 and the back region 108 so that they can deform somewhat independently of the deformation in the target zone 48 and so that the front region 106 and the back region 108 have a degree of upward curl along the longitudinal centerline for better conformability. Optionally, the longitudinal curl outside the target zone 48 can be further enhanced by attaching a portion of the absorbent material in the vicinity of the attachment regions 100 to the backsheet (not shown) by embossing, adhesives, ultrasonic bonding, or other means. The attachment points 100 are desirably near but not within the inverted V-shaped elevated region, and, under lateral compression, can interact with forces transmitted along the outer portions of the absorbent material to deflect the ends of the article upward.

As with other embodiments of the present invention, the presence of the shaping line 54 permits improved body fit relative to an identical article without the shaping lines. The central rising member (not shown) within the article 10 further promotes upward deflection of the central portions of the article 10 for good body fit.

Figure 17:
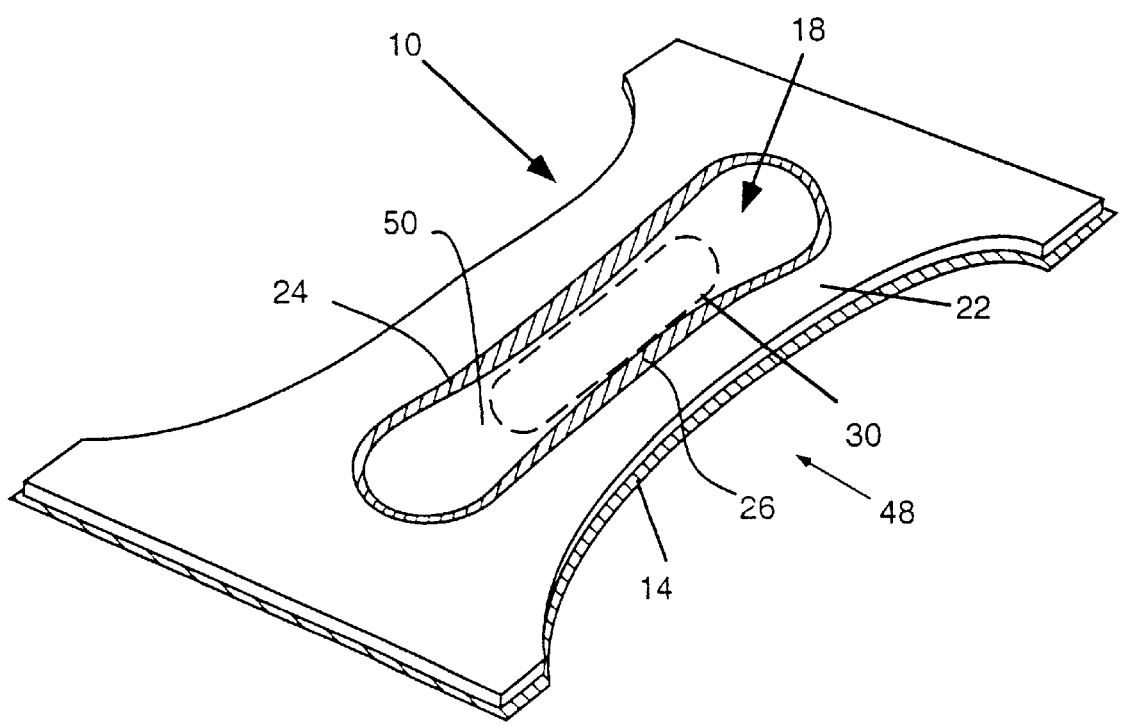
FIG. 17 shows a top view of a diaper with a central rising member beneath a central absorbent member.

FIG. 17 depicts components of an article 10 which is a diaper comprising a central absorbent member 18 having an upper layer 50 and a lower absorbent central rising member 30. The wicking barrier 24 extends below the absorbent central rising member 30. The horizontal component 26 of the wicking barrier 24 traverses a greater distance normal to the periphery of the central absorbent member 18 in the target zone 48 of the article 10 for additional leakage protection.

Figure 18A:
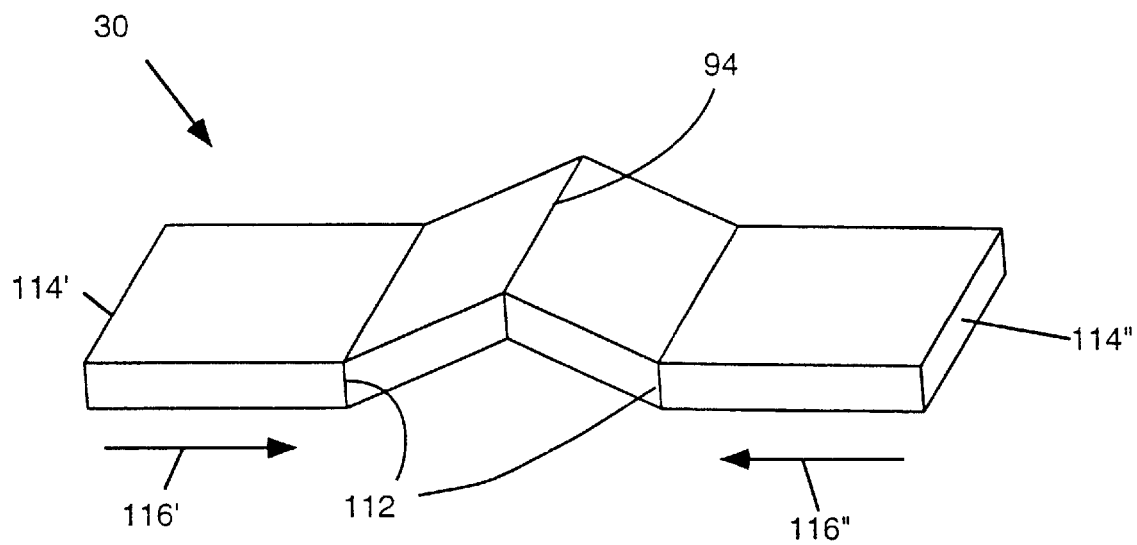
FIGS. 18A and 18B show a perspective view of two central rising members, one that is folded or creased along its longitudinal centerline and one with a loop predisposed to deflect upward.
Figure 18B:
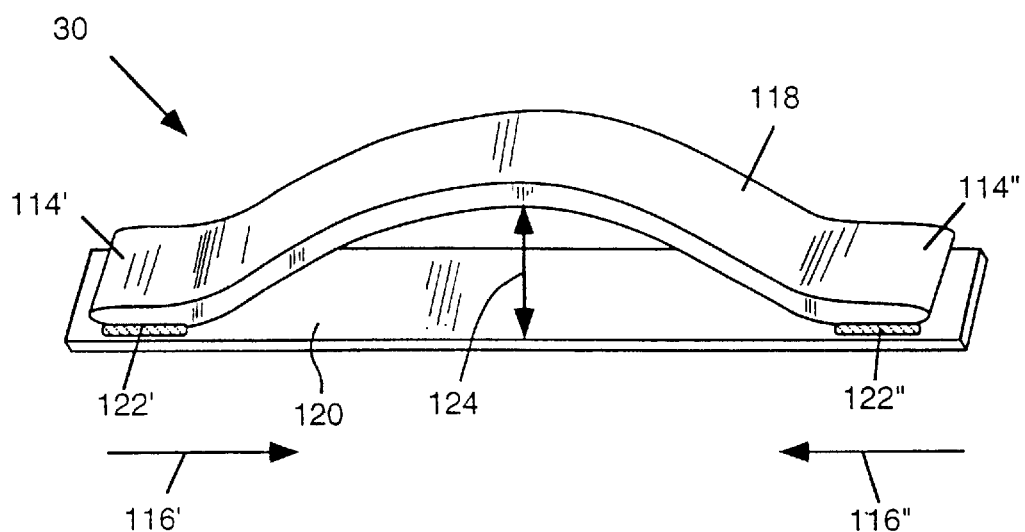

FIGS. 18A and 18B depict a form of a central rising member 30 comprising one or more layers of material that is folded or creased to form an inverted V-shape when the longitudinal sides thereof are moved inward toward the initial longitudinal centerline of the central rising member 30. Specifically, the central rising member 30 comprises a length of absorbent material having a central upward fold serving as a hinge 94, and two downward creases 112, such that moving the longitudinal ends 114', 114" toward each other in the respective directions indicated 116', 116" causes upward deflection along the central fold 94 to increase the apparent thickness of the central rising member 30 and deflect an overlying central absorbent member (not shown) in the vertical direction.

FIG. 18B depicts an embodiment of a central rising member 30 related to that of FIG. 18A, but one that is substantially free of creases or hinge elements. The central rising member 30 comprises a resilient web 118 having ends 114', 114" that are anchored to an underlying web 120 by bond areas 393', 393" which can be adhesive bonds or thermal welds and the like. The length of the resilient web 118 between the bonds areas 122', 122" is greater than the linear distance between the bond areas 122', 122", such that the resilient web 118 forms a loop that is convex toward the body side of the wearer. Prior to compression and in an unloaded state, the central rising member 30 has a gap between the central portion of the resilient web 118 and the underlying web 120 defining a distance 124 which can be about 0.5 mm or greater, and preferably less than about 5 mm, such as a gap height of about 0.7 mm to about 2 mm. When exposed to laterally inward compression, wherein the ends 114', 114" of the resilient web 118 are moved toward one another in the respective directions shown by arrows 116', 116", the gap height 124 increases and the central portion of the resilient web 118 moved vertically upward toward the body of the wearer. (As drawn, the gap height is greatly exaggerated for clarity.)

In one embodiment, the resilient web 118 comprises multiple layers of thin, flexible material such as tissue or layers of polymeric film which have been previously bent or preshaped to be predisposed to flex upward. Even with a very small gap height 124, the preshaping or prior bending of the multi-ply resilient web 118 will generally strongly promote upward flexing during lateral compression.

Figure 19A:
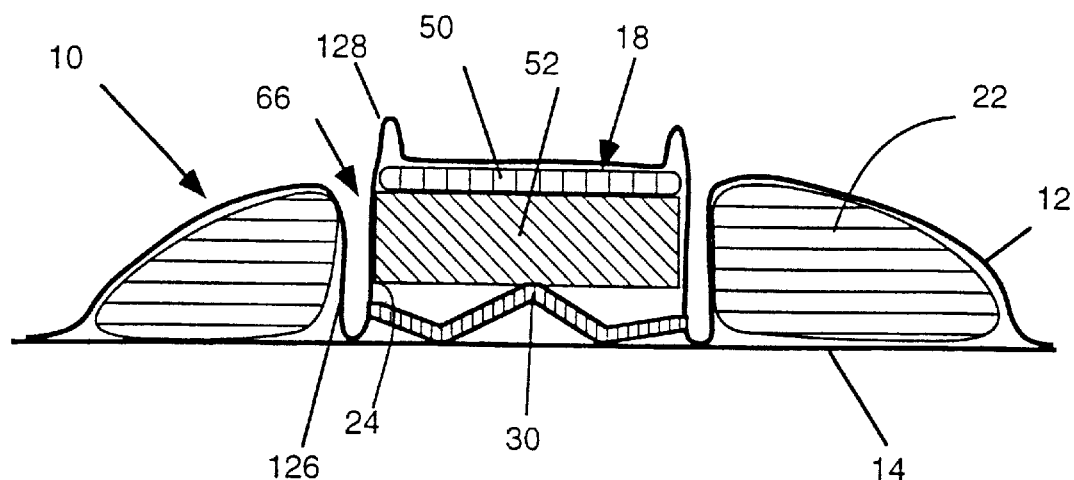
FIGS. 19A and 19B show cross-sections of two related absorbent articles each comprising a protruding loop of topsheet material forming a runoff barrier near the periphery of the central absorbent member.
Figure 19B:
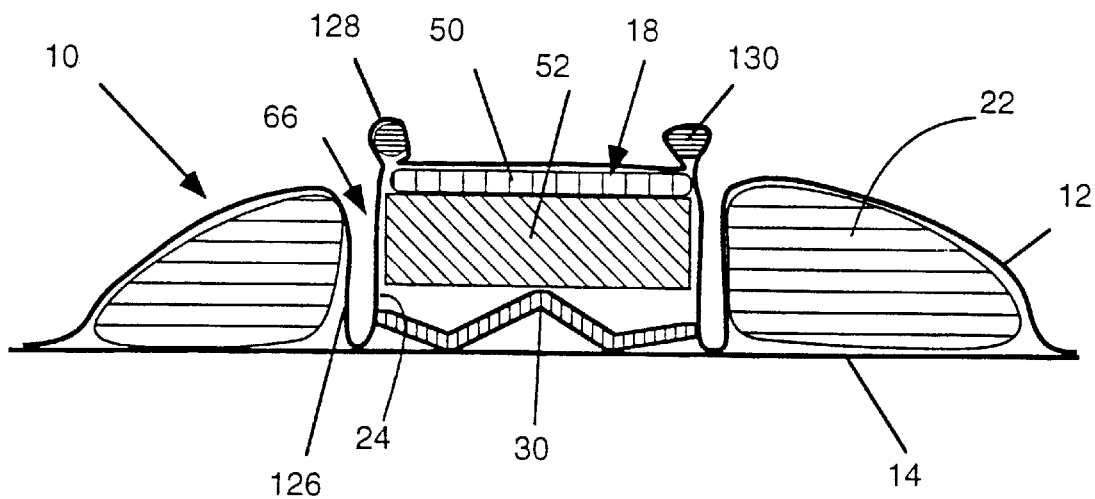

FIGS. 19A and 19B show cross-sections of an absorbent article 10 comprising a central absorbent member 402 with an upper layer 50 for intake and a lower layer 52 for retention, surrounded by an outer absorbent member 22 split into two segments defining a central void 66. Within the central void 66 and beneath the central absorbent member 18 is a central rising member 30 similar to that depicted in FIG. 18A. The central rising member 30 desirably is a fibrous absorbent material having a stiffness per unit thickness (measured in regions not containing flexure points, creases, or bending lines) substantially greater than that of the upper layer 50. A nonwoven or apertured film topsheet 12 also serves as a wicking barrier 24. A downward loop 126 of the topsheet 12 separates the central absorbent member 18 from the outer absorbent member 22 and desirably extends to contact the backsheet 14, as depicted, where it is adhesively, thermally or ultrasonically attached for good integrity. On the body-side surface, a protruding loop 128 of the topsheet 12 forms a runoff barrier near the periphery of the central absorbent member 18. In FIG. 19A, the protruding loop 128 is air filled, while in FIG. 19B, the protruding loop 128 is filled with a soft, pliable material 130 such as tow, a strip of a lofty nonwoven web, loose hydrophobic fibers, a yarn, or a pliable foam. A filled protruding loop 128 can improve the gasketing effect of the runoff barrier and improve conformability to the body. Desirably, the topsheet 12 is treated to be less wettable and/or less permeable in the loop regions 126, 128 than elsewhere on the topsheet 12. Such treatment can be achieved by coating with water repellents, heat treating to seal pores in the topsheet, or by addition of impervious material to the loop regions 126, 128, and especially to the downward loop 126. Desirably, the topsheet 12 is also rendered less pervious or liquid impervious over a portion of the body-side surface of the outer absorbent member 22 most proximate the central absorbent member 18 to provide a ledge effect.

The vertical scale in FIGS. 19A and 19B, as with many cross-sections depicted herein, is not intended to be to scale, but has been expanded to clarify the internal structure. Typically, the thickness of the central absorbent member 18 will be small relative to the transverse width thereof.

Figure 20A:
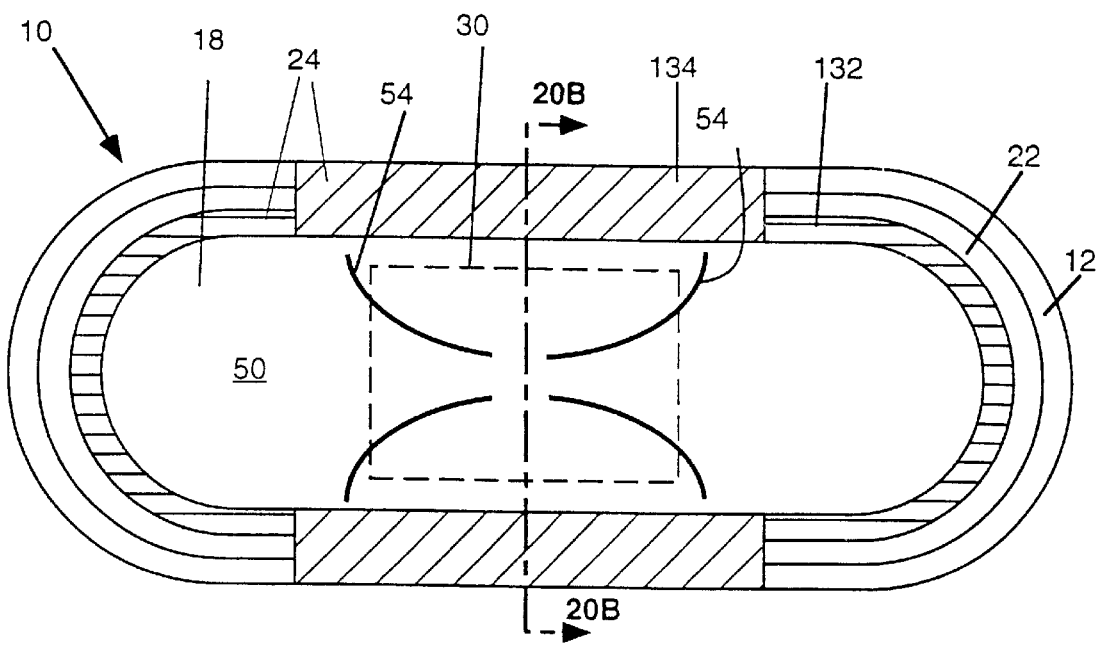
FIGS. 20A and 20B depict top and cross-sectional views, respectively, of an absorbent article 10 according to the present invention with an absorbent central rising member beneath the central absorbent member and with a multi-ply wicking barrier.
Figure 20B:
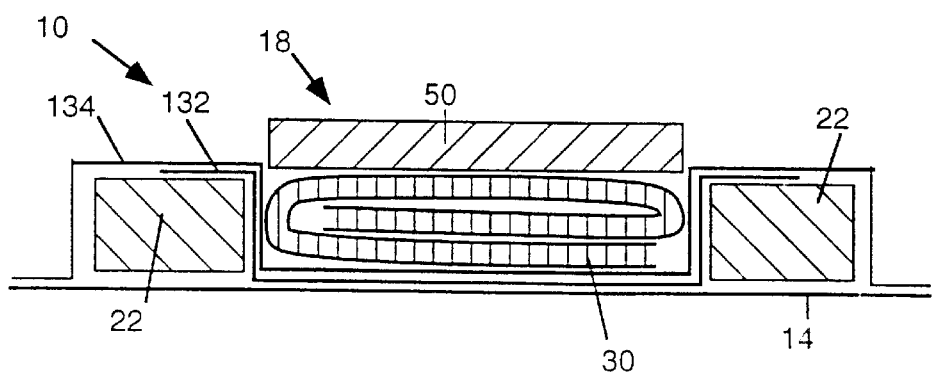

FIGS. 20A and 20B depict top and cross-sectional views, respectively, of an absorbent article 10 according to the present invention. In both figures, topsheet is not shown for clarity. The wicking barrier 24 comprises a first ply 132 and a second ply 134, each having a respective horizontal component 26, 26'. The second ply 134 wraps the outer longitudinal sides of the outer absorbent member 22 and extends along a portion of the backsheet 14. The central absorbent member 18 comprises an upper layer 50 and a lower absorbent central rising member 30 comprising a folded section of an absorbent web such as coform or an airlaid cellulosic material. The upper layer 50 of the central absorbent member 18 is provided with arcuate shaping lines 54 which can be slits to guide upward deflection of the upper layer 50 when laterally compressed.

Figure 21:
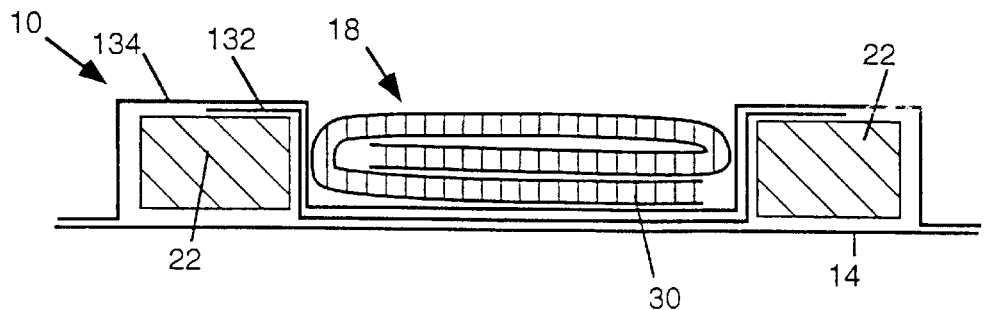
FIG. 21 shows an absorbent article according to the present invention with an absorbent central rising member also serving as the central absorbent member.

In an alternate embodiment shown in FIG. 21, an absorbent article 10 is substantially identical to that of FIG. 20B, except that upper layer 50 of the central absorbent member in FIG. 20B is removed. Now the absorbent central rising member 30 itself serves as the primary component of the central absorbent member 18. Desirably, the "e"-folded web depicted in FIG. 21 has a thickness approximately equal to that of the outer absorbent member 22.

FIGS. 22–32 are discussed in the Examples below.

Without limitation, further principles for construction of absorbent articles according to the present invention are given below in terms of the specific components.

Central Rising Member

The central rising member generally has flexure points or folded sections such as an "e"-folded web (as shown in FIG. 5, for example) such that lateral compression from the longitudinal sides of the central rising member causes at least a portion of the central rising member to deflect upwards with sufficient force that an overlying central absorbent member can be deflected toward the body (or that the central rising member itself can rise toward the body when it serves as the central absorbent member). An absorbent central rising member can also be configured as a flattened tube, as shown in FIG. 11, or an equivalent. Other shapes can also be effective, such as a layer of absorbent material folded or held in the shape of the letter "C" rotated 90 degrees to the right, similar to an inverted "U" with the ends brought together. The rotated "C" shape is especially useful when the internal void space therein is partially filled with another section of absorbent material to prevent collapse and to help predispose the shape to flex upward during lateral compression.

In a preferred embodiment, the density of the central rising member is substantially greater than the density of the outer absorbent member or of the central absorbent member. For example, the density of the central rising member may be about 0.1 g/cc or greater, more specifically about 0.3 g/cc or greater, and most specifically about 0.5 g/cc or greater, with an exemplary range of from about 0.35 g/cc to about 1.3 g/cc. It may be primarily cellulose such as tissue, paperboard, or an airlaid web; synthetic fibers, film, or sheets of polymers such as polyolefins, polyesters, nylon and other polyamides, and the like. In one embodiment, the density of the central rising member is about 30% greater than that of the outer absorbent member, and more specifically about 50% greater.

By way of example, the central rising member whether fibrous or not can have a basis weight of from about 30 grams per square meter (gsm) to about 800 gsm, more specifically from about 50 gsm to about 500 gsm, more specifically still from about 50 gsm to about 300 gsm, and most specifically from about 70 gsm to about 270 gsm.

Desirably, the central rising member comprises at least one ply of a resilient material having a wall thickness wherein the resilient material defines an internal void space due to folding or layering of the material, wherein the z-direction thickness of the internal void increases in size during lateral compression as the upper surface of the central rising member is displaced upward. Alternatively, the central rising member can lack an internal void, being a single layer of material that is folded or creased to form an inverted V-shape or U-shape when the longitudinal sides thereof are moved inward toward the initial longitudinal centerline of the central rising member. An example of this construction is shown in FIG. 18A, as discussed above.

The central rising member can comprise a thermoplastic deformation element as disclosed by K. B. Buell in U.S. Pat. No. 5,300,055, issued Apr. 5, 1994, herein incorporated by reference, but the central rising member can also be non-thermoplastic such as a densified cellulosic web. Thus, the central rising member can have a flexure means, and particularly a longitudinally extending flexure hinge, for inducing the body facing surface of the central rising member to have a convex upward configuration when the sanitary napkin is worn. In an alternative embodiment, the deformation element has a central region having a "W" shaped cross-section wherein the body facing surface of the central rising member having the convex upward configuration is located in the central region, generally symmetrically between the longitudinal side edges of the napkin. In another embodiment, the central rising member has a cup-shaped front region and a back region having a convex upward configured body-facing surface.

Preferably, the central rising member should be resilient enough that it can lift a load of 50 grams by at least 4 mm when it is resting on a solid surface and the longitudinal sides are laterally compressed toward the longitudinal centerline of the central rising member such that the longitudinal sides thereof are brought no more than 13 mm closer due to lateral compression. Rectangular blocks 50-mm long and 5-mm square in cross section, with the 50-mm long dimension aligned with the longitudinal sides of the central rising member, can be used to evenly displace the longitudinal sides toward one another. The load to be lifted is a vertically oriented spindle and foot on a device such as a Mitutoya Digimatic Indicator (e.g., Model 543-525-1). The foot is a stiff section of acrylic plastic 0.7 mm in thickness, 50 mm long and 20 mm wide, placed over the central rising member and centered beneath the spindle of the indicator to more evenly distribute the load of the spindle. The vertical displacement caused by the lateral compression of the longitudinal sides of the central rising member is the vertical distance traveled by the spindle.

The central rising member desirably can still perform its function even when fully wetted. Thus, the central rising member desirably has a degree of wet resiliency, and specifically has a Springback of about 0.7 or greater, as defined in U.S. Pat. No. 5,672,248, issued to Wendt et al. on Sept. 30, 1997. In one related embodiment, the elastic modulus (based on machine direction tensile testing with a crosshead speed of 10 in/min, jaws 2 inches wide, and a gauge length of 2 inches) of the central rising member does not decrease by more than about 30% after being uniformly wetted for five minutes with an amount of distilled water equal to the dry mass of the central rising member, and more specifically does not decrease by more than about 20%. In another embodiment, the elastic properties of the central rising member are substantially unaffected by moisture.

In another embodiment, the central rising member can be a web or layer of resilient material, including a cellulosic densified airlaid web, which is predisposed to deflect vertically upward by virtue of a central hinge element, a shaping line, or a score mark created by creasing or folding the central rising member along its longitudinal centerline. On the garment-side surface of the central rising member, disposed on opposing sides of the longitudinal centerline (or on opposing sides of a central scoremark or shaping line), are attachment means which join together upon contact and hold the opposing sides of the central rising member together to maintain an upwardly flexed shape (e.g., a mountain fold configuration) even when the inward compressive forces that brought the opposing attachment means together are subsequently removed. Velcro® and other known mechanical attachment means can be used. The attachment means can also be magnetic wafers of buttons; adhesive materials, including adhesive agents that have been microencapsulated and only exhibit their adhesive properties after the microcapsules have been broken under compressive stress; interlocking plastic ridges such as those used to seal resealable plastic bags, including ZIPLOC® bags; plastic or metallic snaps; and the like.

The central rising member can also comprise the liquid pervious spacing structure for moving the topsheet away from the core, as disclosed by R. B. Visscher et al. in U.S. Pat. No. 5,324,278, issued Jun. 28, 1994, herein incorporated by reference.

The central rising member can have a flexure resistance of about 50 grams or more, more specifically about 100 grams or more, and more specifically still about 300 grams or more. Increased flexure resistance generally correlates with increased shaping ability of the central rising member, but high flexure resistance can also mean increased stiffness of the article and increased discomfort. Desirably, the flexure resistance of the central rising member is less than 1000 grams and more specifically less than 500 grams. In some cases, good performance can still be achieved when the central rising member has a relatively low flexure resistance, such as a resistance less than 100 grams, more specifically 90 grams or less, and most specifically about 80 grams or less, particularly when the central absorbent member itself is provided with bending lines and more particularly when adhesive bonds join the central absorbent member to at least one portion of the central rising member, possibly via bonds to an interposed wicking barrier, such that the central rising member can promote upward deflection without significant stiffness and with very little risk of discomfort to the wearer.

In some embodiments, the central rising member can be wider than the central void of the outer absorbent member. For example, an absorbent article can comprise an outer absorbent member with a central elliptical hole therein. An absorbent central rising member can be disposed beneath the outer absorbent member such that a portion of the absorbent central rising member is in the hole, but side portions such as tapered sides of the central rising member can extend beyond the walls of the void and be disposed beneath the outer absorbent member. A wicking barrier could then be a polymeric film passing beneath the absorbent central rising member, wrapping the sides of the absorbent central rising member, and then rising along the walls of the central void of the outer absorbent member, whereupon the wicking barrier extends a horizontal distance over the body-side surface of the outer absorbent member toward the longitudinal sides of the article.

Central Inflatable Member

In contrast to a central rising member, which generally relies on lateral compression to cause the upward deflection for improved body fit, a useful alternative is a central inflatable member which can urge a central absorbent member upward toward the body without necessarily requiring lateral compression to cause upward deflection. Thus, an inflatable bladder or envelope may be provided below or within the central absorbent member, wherein the bladder can be filled with a gas to become inflated and thus urge the central absorbent member upward. The gas may be provided by a small deformable pouch with a one-way air intake valve that can be pumped by body motion or by action of the fingers to drive air into the bladder, which also has a one-way valve or flap to hold air in the bladder but to permit its entry. The central inflatable member may also be or comprise a sealed expandable component as disclosed in U.S. Pat. No. 5,520,674, "Disposable Absorbent Article Having a Sealed Expandable Component," issued May. 28, 1996 to Lavon et al. In a preferred embodiment, the expandable component comprises a compressed resilient element disposed within an air impermeable envelope. The air impermeable envelope can be evacuated, such as by vacuum sealing, to have an internal pressure less than the outside atmospheric pressure. The expandable component expands from a first thickness to a second thickness greater than the first thickness upon opening of the air impermeable envelope.

The air impermeable envelope can comprise a port having a releasable closure. The releasable closure can be removed at the point of use of the disposable absorbent article to permit air to enter the envelope through the port, thereby providing expansion of the expandable component. In one embodiment, the releasable closure can be resealable, so that air drawn into the port does not escape when the expandable component is subjected to compressive loading.

The resilient compressed element is preferably porous, so that when a releasable closure is removed from a port in the air impermeable envelope, expansion of the resilient element draws air into the resilient element, as well as into the space in the cavity within the air impermeable envelope not occupied by the resilient element. In one such embodiment, the resilient element can comprise a porous sponge or open celled foam.

The central inflatable member can comprise an initially collapsed bladder with a one-way intake valve that can be manually expanded prior to or during use.

Space between two gas impermeable film layers or, more generally, within a bladder or gas impermeable envelope can also be filled with gas from sources other than the atmosphere. In other words, internal gas production means within the bladder or envelope can be useful for the inflation of the central inflatable member. For example, chemical means can be used to produce gas inside the bladder or envelope. Reagents such as vinegar and baking soda can be reacted to release carbon dioxide, when a barrier or seal separating the two reagents is broken or removed. Many other known gas producing agents can be used, including those that are encapsulated and yield gas only when the capsules are broken. Several related embodiments are disclosed in U.S. Pat. Nos. 3,881,491 and 3,921,232 issued to Whyte on May 6, 1975 and Nov. 25, 1975, respectively, and U.S. Pat. No. 5,876,393, issued to N. A. Ahr et al. Mar. 2, 1999.

Additional Materials in the Absorbent Core

The article may also comprise hydrophobic material around the sides of the absorbent core to further reduce edge leakage. For example, hydrophobic fibers may be placed in discrete areas, such as around the periphery of the hydrophilic absorbent core, to provide barriers against leakage, as exemplified in U.S. Pat. No. 5,817,079, "Selective Placement of Absorbent Product Materials in Sanitary Napkins and the Like," issued to R. Bergquist et al., Oct. 6, 1998. A related approach which can be applied to the present invention is given by Csillag in U.S. Pat. No. 4,015,604, issued Apr. 5, 1977. An absorbent product is disclosed with side leakage control means comprising a narrow longitudinally extending zone along each side edge of the product but spaced away from each of the side edges. This zone is impregnated with a liquid hydrophobic material from the garment facing surface to the body facing surface of the product. The hydrophobic impregnate is applied to a hydrophilic pad as the pad passes through the manufacturing equipment. Likewise, Canadian Patent No. 884,608 issued to Levesque, Nov. 2, 1971, relates to treating the edges of a sanitary napkin product with hydrophobic material in order to prevent side leakage. In accordance with Levesque, the absorbent layer in the zone of the edges of the absorbent material is rendered hydrophobic while being maintained in a gas and moisture vapor permeable condition. The hydrophobic zone may be coated with a liquid repellent composition or chemically modified to render the fibers hydrophobic. In these embodiments with added hydrophobic fibers or hydrophobic matter toward the longitudinal sides of the absorbent core, it is nevertheless desirable that a wicking barrier such as a polymeric film passes over at least a portion of the surface of the hydrophobic areas in the crotch region of the absorbent core.

The absorbent core may also comprise a percentage of water-swellable minerals such as bentonite particles, vermiculite, and the like, preferably in the range of about 2% to about 40% by weight, and desirably mingled with cellulosic fibers or free flowing particulates, described hereafter.

Other components may be combined with the cellulosic materials of the absorbent core or added as separate layers or portions of the article. Such other components include odor absorbing components such as baking soda, talc powder, cyclodextrin, ethylenediamine tetra-acetic acid, zeolites, activated silica, and activated carbon granules, fabrics or fibers; superabsorbent particles and fibers; fluoropolymers; antimicrobial agents including the silver-loaded zeolites of B F Technologies, located in Beverly, Mass., sold under the trademark HEALTHSHIELD™ as well as triclosan products, chitosan or chitin derivatives (useful principles for application of chitosan finishes to nonwoven webs and cellulosic fibers are described by S. Lee et al., "Antimicrobial and Blood Repellent Finishes for Cotton and Nonwoven Fabrics Based on Chitosan and Fluoropolymers," *Textile Research Journal*, 69 (2): 104–112, Feb. 1999); polycarboxylic acids; encapsulated perfumes; emollients such as lanolin; or skin wellness agents such as aloe vera extract (particularly aloe vera powder combined with a polyhydroxy softener) or vitamin E. Thermoplastic binder fibers may be added, with or without subsequent heat treatment for improved stability. Foam layers, foam shape-defining components, or foam particles may also be present. Plastic inserts to define shape or maintain integrity may also be used.

Other Embodiments for the Central Absorbent Member

The central absorbent material may be two or more strips of cellulosic material, such as an upper strip of an airlaid or wetlaid material having a first density or mean pore size and a second lower strip of an airlaid or wetlaid material having a second density or mean pore size. Desirably, the mean pore size of the lower strip is smaller than that of the upper strip such that capillary forces will preferentially remove fluid from the upper strip into the lower strip for an improved dry feel. Desirably, the central absorbent member has a substantially higher basis weight than the outer absorbent member for better efficiency in material usage.

If two or more strips are present in the central absorbent member, the basis weight of the lower strip can be about the same, less than, or greater than that of the upper strip. Two or three layers with differing wicking capacities can be used, as disclosed in U.S. Pat. No. 5,401,267, issued Mar. 28, 1995 to Couture-Dorschner et al., desirably with the lower layer having a higher capillary pressure (smaller pore size).

The central absorbent member can also comprise a central opening or aperture (known as a "port hole," especially in European markets), exemplified by the teachings of German patent application No. 19640451. The port hole may be filled with a pouch of free-flowing particles or may remain open for intake of viscous fluid.

The central absorbent member may be tapered with sides that overlap a portion of the outer absorbent member, with the tapered sides being above or below the outer absorbent member. For example, a central absorbent member comprising a central rising member, such as a pre-shaped pledget of fluff pulp predisposed to flex upward when laterally compressed, may have thin side portions that extend beneath the outer absorbent member (i.e., the transverse width of the central absorbent member can be greater than the transverse width of the central void in the outer absorbent member). In such an embodiment, the wicking barrier can wrap the longitudinal sides of the central absorbent member beneath at least a portion of the outer absorbent member and then rise along the inner walls of the central void in the outer absorbent member to isolate the central absorbent member from the outer absorbent member.

The central absorbent member can comprise multiple layers. In one preferred embodiment, the central absorbent member comprises a top intake layer, which may be a tissue layer or other absorbent material adapted for rapid intake of fluid, a longitudinal wicking layer for effective transfer of liquid in the longitudinal direction, and a lower fluid retention layer, which may comprise superabsorbent material, densified pulp fibers, microstrained pulp sheets, tissue, coform, or peat moss. The longitudinal wicking layer can comprise densified airlaid strips having a longitudinal length greater than their transverse width; wet laid tissue with a mean fiber orientation predominately in the longitudinal direction; a plurality of other absorbent strips or filaments. Other longitudinal strips of absorbent material such as tow can be used to enhance directional transport of the fluid.

The Outer Absorbent Member

Desirably, the outer absorbent member is fibrous with fibers that are essentially discontiguous with the central absorbent member (i.e., the central absorbent member and the outer absorbent member do not share fibers that join the two members). The outer absorbent member desirably has a lower basis weight than the central absorbent member but still provides several important functions. Generally, it is intended that the outer absorbent member remain unwetted except in cases of heavy flow. The unwetted structure of the outer absorbent member does not collapse but maintains high integrity in the dry state, which helps maintain the shape and fit of the article. When it does become wetted, the outer absorbent member can serve as an indicator that the absorbent article needs to be replaced.

For both the outer absorbent member and the central absorbent member, if the absorbent member is comprised of more than one constituent part or material, one part or material of the absorbent member may not be absorbent or liquid permeable, so long as the combination of parts or materials has some degree of absorbency and some degree of the properties set forth above. Desirably, however, the majority of the material by mass is absorbent and more desirably at least about 90% of the material of the absorbent member is inherently absorbent. In one embodiment, substantially all of the absorbent member is composed of absorbent material.

Outer Shaping Member

The use of a wicking barrier between a central absorbent member and an outer absorbent member can reduce the need for the outer absorbent member to actually absorb significant quantities of fluid. Recognizing that the primary absorbent material in the central absorbent member can provide substantially all of the absorbent capacity needed for many absorbent articles such as a feminine care pad (typically 7 milliliters (ml) of fluid will be absorbed, with a high end of about 15 ml), the outer absorbent member can be used to achieve several important functions other than absorbency. Either as a ring of material around the central absorbent member or as a pair of longitudinal bands surrounding the central absorbent member longitudinally, the outer member helps define the shape of the article, particularly when attached adequately to the wearer's panties. In conventional sanitary napkins, the article can become excessively bunched or compressed when wetted, but by maintaining the outer absorbent member in a dry state, it can maintain its shaping and body fit functions throughout use. Thus, the outer absorbent member can serve as a shaping and body fit element as well as a "cradle" to hold the central absorbent member and the wicking barrier in place. In fact, these functions can be achieved whether the outer member is absorbent or not, though it is desirable that the outer member be absorbent to take up fluid that might not be successfully held by the central absorbent member. Nevertheless, in one embodiment of an absorbent article such as a feminine care pad designed to maintain good body fit and provide leakage protection, the outer member need not be absorbent at all but can be a flexible frame member capable of holding the wicking barrier and central absorbent member in place. Thus, an outer shaping member can be used instead of an outer absorbent member, though it is preferred that the outer member be absorbent.

The shaping member can be porous, such as a ring of a polyurethane or a foam rubber material (e.g., foamed styrene butadiene), foamed silicones, or foamed vinyl plastics. Several such foams can be obtained from Woodbridge Foam Fabricating, Inc., located in Chattanooga, Tenn., from the E. N. Murray Company, Inc., located in Denver, Colo., and Astro-Valcour, Inc., located in Glens Falls, N.Y. Foam materials desirably have a density of about 0.02 grams per cubic centimeter (g/cc) to about 0.1 g/cc. The foam material desirably is treated to be absorbent and/or hydrophilic, but need not be hydrophilic. In the case of a closed-cell foam or a foam with an impervious skin on the outer surface, the surface of the foam itself can serve as a wicking barrier having both a vertical component and a horizontal component on the bodyside surface of the shaping member. Thus, in general, the outer shaping member can comprise an integral wicking barrier or can have an additional polymeric barrier provided on its surface, or can be separated from the central absorbent member by a separate layer of barrier material serving as a wicking barrier.

In one related embodiment, the wicking barrier and the outer shaping member are also integral with a backsheet and can be composed from a single piece of impervious material. The backsheet then also can serve as the baffle layer beneath the central absorbent member. For example, a single section of shaped flexible closed cell foam, desirably comprising an external impervious skin, can be shaped to provide a thin central layer under the central absorbent member, expanding away from the longitudinal centerline to provide thicker regions outside the central absorbent member that serve as the outer portions of the outer shaping member. (The thin central portion is a bridging portion between the outer portions.) Since the central absorbent member is contained by the outer shaping member (within the central sides of the outer portions and above the underlying thin bridging region of the foam body), there is no need for an additional backsheet, assuming the foam is truly impervious or comprises an impervious skin.

In general, for embodiments with an impervious or non-absorbent outer shaping member, a separate backsheet is not necessary. Nevertheless, some form of a baffle layer must exist beneath the central absorbent member to prevent leakage. If a substantially liquid impervious outer shaping member is used and is contiguous, e.g., comprises first and second outer portions joined by a relatively thin (thinner than the outer portions) bridging member, then the outer shaping member itself can serve as the baffle layer and can replace the function of a backsheet, if desired. If a complete hole rather than merely a depression exists in the central portion of the outer shaping member for receiving the central absorbent member, then a separate baffle layer must be used. This can be a liquid impervious backsheet, a portion of which serves as the baffle layer beneath the central absorbent member, or it can be the wicking barrier if it runs beneath the central absorbent member to prevent leakage of fluid toward the garment side of the article, or it can be a separate layer of impervious or hydrophobic material such as a flexible polymer film, including material integrally attached to the central absorbent member such as a thermoplastic film, or an impervious coating or layer of adhesive. In any case, the construction of the article generally serves to isolate fluid in the central absorbent member for a true center-fill effect and prevent or reduce substantial fluid contact with the outer shaping member, while providing a conformable article that can fit against the body in use.

An outer shaping member comprising foam or other materials can be preshaped to conform suitably to the body.

Examples of materials and methods for preparing conformable, resilient shaped members are disclosed in U.S. Pat. No. 5,591,150, issued Jan. 7, 1997 to Olsen et al. The outer shaping member can comprise absorbent materials, particularly cellulose, such as a regenerated cellulose foam or stabilized fluff pulp or air laid wood fibers, stabilized with thermoplastic fibers, crosslinkers, or wet strength agents, and may be preshaped or can be planar. Desirably, the outer absorbent member comprises densified fluff pulp, stabilized air laid pulp, or the soft pulp sheets disclosed in U.S. Pat. No. 5,562,645, issued Oct. 8, 1996 to Tanzer et al., and desirably has a density less than 0.2 g/cc and more specifically less than 0.1 g/cc. Coform can also be used. The outer shaping member can be a composite element, such as a layer of cellulosic fibers joined to a polymeric foam layer. In one embodiment, the outer shaping member is extensible such that its size can be adjusted for improved fit. The outer shaping member can also be biodegradable and/or flushable, if desired. Further, the central absorbent member can be detachable from the outer shaping member to permit disposal and replacement with a new central absorbent member, rather than discarding the entire article.

As with the outer absorbent member, the outer shaping member desirably promotes good body conformability. When used in sanitary napkins or feminine pads, for example, the outer shaping member desirably promotes a W-fold geometry in the crotch region when the pad is worn. Thus, the size, thickness, stiffness, and geometry of the outer shaping member should be adjusted to permit it to flex in use into a W-fold when combined with the other components of the absorbent article. Design principles given herein for embodiments comprising an outer absorbent member can generally be applied to embodiments comprising an outer shaping member, in addition to explicit teachings herein for the outer shaping member.

For best comfort, the outer shaping member or outer absorbent member desirably should be soft, resilient and easily compressible. The resiliency should be in the range of about 15 percent to about 60 percent rebound, preferably about 15 percent to about 50 percent and more preferably about 15 percent to about 35 percent, as determined by the ASTM Test Method D3574-91 procedure H. Compressibility should be in the range of about 0.69 kPa (0.1 pounds per square inch (psi)) to about 13.8 kPa (2 psi) at 50% compression, preferably from about 2.1 kPa (0.3 psi) to about 11.7 kPa (1.7 psi) at 50% compression and most preferably from about 3.45 kPa (0.5 psi) to about 10.3 kPa (1.5 psi) at 50% compression, as determined by the ASTM Test Method D3574-91 procedure C.

Generally, the outer shaping member has a thickness of at least about 1 mm, specifically at least about 2 mm, more specifically at least about 3 mm, and most specifically from about 3 mm to about 7 mm. Desirably, the average thickness of the shaping member is at least about 20 percent of the average thickness of the central absorbent member, and more specifically is at least about 30 percent of the average thickness of the central absorbent member. The thickness of the outer shaping member can also be greater than that of the central absorbent member. For example, the average thickness of the central absorbent member can lower by at least about 20 percent or at least about 50 percent than the average thickness of the outer shaping member.

The "edge width" of the outer shaping member, defined herein as the lateral distance along a continuous portion of the outer shaping member along the transverse centerline, specifically from the inner edge (adjacent the central absorbent member) of the outer shaping member to the outer edge thereof, is desirably at least about 2 mm and specifically at least about 3 mm, more specifically at least about 4 mm. For example, a 7 cm wide rectangular foam section with a 5 cm wide central void therein for receiving a central absorbent member would have an edge width of 1 cm.

In a preferred embodiment, the outer shaping member is also an outer absorbent member comprising cellulosic fibers, the outer absorbent member being substantially surrounded by impervious material (e.g., the wicking barrier and the backsheet) such that the absorbent material remains substantially dry in use. In one embodiment, the wicking barrier completely covers the body-side surface of the outer absorbent member and forms a seal with the backsheet in the region between the outer absorbent member and the central absorbent member and, optionally, is attached to the backsheet adjacent the outer periphery of the outer absorbent member. Small apertures may be provided in the wicking barrier to permit some fluid intake into the outer absorbent member when the central absorbent member is heavily saturated, but ordinarily the outer absorbent member will remain dry. The apertures may be provided only near the longitudinal ends of the central absorbent member such that fluid cannot wick directly toward the crotch region of the outer absorbent member. Thus, the outer absorbent member primarily serves to provide comfort and body fit, while providing a substrate on which the wicking barrier can rest to resist fluid flowing out of the article.

The absorbent core can further comprise fluid distribution elements such as the pumping elements of U.S. Pat. No. 5,769,834, issued Jun. 23, 1998 to Reiter et al., wherein tubular elements are used to move fluid from one region of the absorbent core to another. The tubular elements desirably are outside the central absorbent member of the absorbent core and are adapted to intercept liquid that may escape from the longitudinal sides of the central absorbent member and move it toward the longitudinal ends of the absorbent core.

Additional Embodiments for the Wicking Barrier

In embodiments using an apertured film for the wicking barrier, the film should be oriented to hinder flow from the central absorbent member toward the outer absorbent member. Many apertured films provide flow directionality, wherein flow passes through the film most easily when fluid is deposited on one side of the film. For example, many films have tapered or conical apertures with large openings on one side and narrow openings on the other, wherein fluid on the side with the large openings passes readily through the film, whereas fluid on the side with the narrow openings is more likely to be hindered from passing through the film. When a film provides such directionality, it is desirable that the side most likely to hinder fluid flow be placed toward the central absorbent member. In this manner, wicking flow from the central absorbent member to the outer absorbent member may be delayed until the central absorbent member is substantially saturated.

In some embodiments, the wicking barrier need not be hydrophobic and can even be absorbent as long as wicking is substantially hindered by a barrier function provided by the wicking barrier. For example, a liquid impervious film of superabsorbent material such as a polyacrylate film can be used. The film may swell and absorb water without permitting wicking flow to extend beyond the film.

The wicking barrier can comprise a plurality of components, such as two or more sections of polymeric film, or a combination of an impregnated region on the surface of the an absorbent member and a polymeric film, and the like.

In one embodiment, the wicking barrier can comprise two longitudinal sections which descend into a gap between the central absorbent member and the outer absorbent member and contact the backsheet, where two sections of the wicking barrier can individually be joined to the backsheet for stability. Further, a single or unitary wicking barrier can have sections which descend to contact the backsheet and are joined thereto. For example, a single section of wicking barrier material could be provided with central slits in the shape of an I-beam (or the shape of the letter "H" rotated by 90 degrees), yielding two hinged sections that could pass through a slit or gap in the absorbent core (particularly the gap between the central absorbent member and the outer absorbent member in the crotch region) to contact and be joined with the backsheet. The wicking barrier material can further rise back toward the body-side surface of the absorbent core to contact the body-side surface of the central absorbent member.

Bending Lines

As used herein, the word "line" or "lines" in the terms "shaping line" and "crease lines" refer to narrow, elongated sections that promote folding by providing a sudden change in material properties of matter along the line relative to matter on either side of the line. A line can be straight, arcuate, sinusoidal, wavy, angular, or zig-zag-like, and can have multiple elements, such as a line that extends longitudinally followed by a bend or turn toward the center of the article, or can be a series of short segments that define a line. A shaping line or crease line may also be comprised of a series of dots, such as dots formed by adhesives or heat and pressure to create densified, bonded spots spaced apart to define a line. Lines can have a width less than about 10 millimeters (mm), desirably less than about 5 mm, more specifically less than about 3 mm, and most specifically between about 0.5 mm and about 2 mm. Since a shaping line will generally have multiple components, such as longitudinal portions and outwardly spanning segments, the terms "shaping lines" and "shaping line" can generally be used interchangeably.

During laterally inward compression from the longitudinal sides, it is desired that an essentially W-shaped fold be established in the crotch region of the absorbent article due to deflection of the absorbent core. As used herein, a "W-shaped fold" in the absorbent article means that the cross-section of the laterally compressed article along or near the transverse centerline of the article shows a shape approximated by the letter W, with outer valleys around a central mound. The central mound may be rounded, relatively flat at the top, or sharp like an inverted V. A W-shaped fold can be produced with simple lateral compression by proper placement of crease lines and a shaping line or lines. Typically, the crease lines, when used, are located outside the central absorbent member of the absorbent core of an absorbent article. Downward folding along the crease lines is typically associated with upward folding of the longitudinal sides of the article in the crotch region. The crease lines can be coupled with a shaping line or shaping lines closer to the longitudinal axis of the article than the crease lines, typically located in the central absorbent member of the absorbent core of an absorbent article, wherein the shaping line promotes or permits upward folding of the central region of the absorbent core during lateral compression to provide good body fit. The shaping line, closer to the longitudinal centerline of the article than the crease lines, is designed to translate lateral compression into vertical deflection (upward protrusion) of a central region of the absorbent article, resulting, for example, in an upward mound, particularly when combined with the downward deflection of the article along the crease lines.

Desirably, the upward mound, created near the longitudinal centerline of the article by the upward motion of the central regions of the absorbent article as directed by the shaping lines, does not persist throughout the length of the article, but, as influenced by the shaping lines, terminates just outside the crotch region to permit the article to better conform to the regions outside the crotch area, where an inverted V-shape may be useful in the rear of the article to better conform to the buttocks, and where the article generally should be relatively flat in the transverse direction and curled concave up in the longitudinal direction for best body fit in the front of the pad. Proper shaping of regions outside the crotch region during lateral compression can be achieved by providing additional slits, reinforcing elements, elastic components, or attachment elements to the absorbent core.

In one exemplary embodiment, the absorbent article comprises one or more layers of absorbent material with outwardly concave arcuate crease lines in the crotch region formed by embossing the absorbent material near the longitudinal sides of the article, further comprising a central shaping line formed by perforating or notching the absorbent material in the central region of the pad, the shaping lines having a geometry similar to a double headed arrow with reverse arrow heads, or ">—<", centered along the longitudinal centerline of the article between the crease lines, and with the longitudinal axis of the arrow aligned with the longitudinal axis of the article. Such a geometry for the shaping line permits the central region of the absorbent core between the outward "arrow heads" to deflect upward while downward deflection occurs along the crease lines. Another successful geometry for the shaping line is a pair of outwardly concave arcuate lines whose midpoints touch or approach each other, longitudinally aligned and substantially symmetrically placed about both sides of the longitudinal axis in the crotch region between the outer crease lines, and desirably smaller in length than the crease lines. Such arcuate crease lines resemble the shape of a right and left parentheses placed back to back, or ")(", with the vertical axis of the parentheses substantially aligned with the longitudinal axis of the article. Likewise, the shaping line in many embodiments can be described as convex toward the longitudinal centerline of the article and generally contained within the absorbent core and specifically generally contained within the central absorbent member.

The shaping line or crease lines of the absorbent article can generally be created in any way likely to guide the folding of a flexible material having a degree of intrinsic stiffness such as an air laid pad, a mat of fluff pulp, a stack of tissue layers, a web of coform material or other fiber-polymer composites, or a high-loft nonwoven web. The shaping line or crease lines desirably are produced by one of more treatment methods such as embossing, stamping, or other known methods for creating densified regions, as, described in U.S. Pat. No. 4,655,759, issued Apr. 7, 1987 to A. Y. Romans-Hess et al. Other methods for line formation include slitting; slotting; cutting; notching; tearing; thermo-bonding (application of heat to create bonding, particularly with thermoplastic materials or heat-setting resins); hot pressing (simultaneous application of heat and pressure, especially in conjunction with thermoplastic binder materials, thermosetting plastics, or heat setting resins); ultrasonic bonding; perforating; perf-embossing; needling; impregnation by resins, waxes, or thermoplastics; hydraulic cutting by water jets or other fluid jets; pre-folding; creasing;

scoring; or removing material by abrasion, ablation, picking, scraping, or suction.

Crease lines and shaping lines can also be created by bonding a portion of the cover or backsheet to a compressed portion of the absorbent material using the methods described by Mogor in U.S. Pat. No. 3,575,174, issued Apr. 20, 1971. The articles of the present invention can also comprise embossments in the back region of the article to promote an inverted V-shape fold in the rear of the article for more comfortable article placement between the buttocks of a user.

The length spanned by the shaping line or lines in the longitudinal direction can be at least about 1 cm, specifically at least about 2 cm, more specifically from about 3 cm to about 10 cm, more specifically still from about 4 cm to about 8 cm, and most specifically from about 4 cm to about 6 cm. In sanitary napkins and other absorbent articles, a longitudinal slit or notch, if present, desirably can be from about 4 cm to about 6 cm long. The longitudinal length of the crease lines can be smaller than that of the shaping lines, but in most embodiments desirably is about the same as or longer than that of the shaping line. For example, the crease lines can be longer than the shaping lines in the longitudinal direction by at least about 1 cm, more specifically at least about 2 cm, more specifically at least about 3 cm, and most specifically from about 2.5 cm to 5 cm.

Superabsorbent Material

The absorbent cores of the present invention can comprise superabsorbent particles, such as from 5% to 90% by mass superabsorbent particles on a dry mass basis, or from about 30 to about 70% superabsorbent particles, alternatively from about 10% to about 50% superabsorbent particles and more specifically from about 10% to about 40% superabsorbent particles. Superabsorbent material can be incorporated as loose particulates, particles bound to the hydrophilic fibers, superabsorbent fibers, or as a component of the binder material or structuring composition. Superabsorbent material can also be provided in the form of a foam, as disclosed in U.S. Pat. No. 5,506,035, "Superabsorbent Polymer Foam," issued to Van Phan et al., Apr. 9, 1996, or incorporated into the void spaces of an absorbent foam.

In one embodiment, the absorbent core comprises a laminated or layered structure having superabsorbent particles or fibers present in at least one layer. The superabsorbent material can also serve as a binder to hold the fibrous composite in a densified state. For example, European Patent 758,220-B, issued to U. Widlund, Feb. 19, 1997, teaches the use of moistened superabsorbent particles to serve as a binder in creating laminated materials, with densification provided by passing the composite through a heated nip.

Superabsorbent material bonded to cellulosic fibers can also be beneficial for use in the present invention. For example, binders may be used to join the superabsorbent particles to cellulosic fibers, as disclosed by Hansen et al. in U.S. Pat. No. 5,547,745, issued Aug. 20, 1996 and U.S. Pat. No. 5,693,411, issued Dec. 2, 1997. (Such binder systems can also be used to attach many other solids to the fibers of the present invention, including zeolites, baking soda, activated carbon particles, $TiO_2$, clay, bentonite, talc, and the like.)

Superabsorbents can also be attached to specific portions of a cellulosic or nonwoven web, such as the elevated or depressed regions on an imprinted tissue sheet, as disclosed in U.S. Pat. No. 5,487,736 issued to D. Van Phan, Jan. 30, 1996. Fiber-superabsorbent composites can also include combinations of both anionic and cationic superabsorbent polymers, with one or both polymers joined to a substrate such as cellulose fibers via covalent bonds, and particles from the two polymer types joined by ionic bonds, as disclosed in U.S. Pat. No. 5,853,867 issued to N. Harada et al. Dec. 29, 1998. In one embodiment, discrete zones of anionic and cationic superabsorbent particles are provided in the article, such as discrete pockets alternating between cationic and anionic superabsorbent particles. Superabsorbents can also be prepared with both acidic and basic groups or anti-microbial factors to help prevent odors and bacteria growth.

The Topsheet

The topsheet has a body-facing side and a core-facing side. The body-facing side of the topsheet generally forms at least a portion of the body surface of the article. The topsheet should permit liquids to readily transfer through its thickness toward the absorbent core. The topsheet can comprise any fluid pervious cover material known in the art, such as nonwoven webs or apertured films, or other materials such as hydrophilic wet laid basesheets treated with portions of hydrophobic matter, including those of Chen et al. in commonly owned copending application, "Dual-zoned Absorbent Webs", Ser. No. 08/997,287, filed Dec. 22, 1997. Nonwoven webs used to produce a topsheet can include layers of spunbond material, meltblown material, and combinations thereof. The nonwoven webs may be apertured or slitted webs or provided with treatments for improved wettability, including corona discharge treatment, or treatments for improved flow permeability, such as hydroentangling or aperturing or microembossing. Creping of the nonwoven web using methods known in the art can desirably improve softness, appearance, and performance of the topsheet. The topsheet can comprise a layer of a perf-embossed or apertured film on the body side bonded to a layer of a nonwoven web, preferably treated to be hydrophilic, on the core side. Similarly, the topsheet can comprise two or more nonwoven layers or film and nonwoven layers that have been co-apertured to provide apertures suitable for rapid intake of viscous or viscoelastic fluids and to improve wicking contact with underlying absorbent materials.

Exemplary topsheets can be made in accordance with U.S. Pat. No. 5,533,991, issued Jul. 9, 1996 to Kirby et al.; U.S. Pat. No. 4,342,314 issued Aug. 3, 1982 to Radel et al. and U.S. Pat. No. 4,463,045 issued Jul. 31, 1984 to Ahr et al. The topsheet may comprise an additional transfer layer to help direct fluid into the absorbent core, as disclosed, for example, in U.S. Pat. No. 4,397,644, issued Aug. 9, 1983 to Matthews et al.

The topsheet and the backsheet may be adhesively attached to the absorbent core. Useful principles for adhesively attaching topsheets or other lamina to absorbent cores comprising comminuted fibers are disclosed in U.S. Pat. No. 4,573,986, issued Mar. 4, 1986 to Minetola et al.

The topsheet or cover itself can play an important role in preventing wicking contact during bunching of the absorbent article. In one embodiment, the cover can be rendered substantially impervious over the outer absorbent member in the crotch region such that wicking between absorbent members is impeded even when the outer absorbent member is folded into contact with the central absorbent member. An apertured film, for example, can simply be made free of apertures in regions where imperviousness is desired such as over the outer absorbent member in the crotch region or over the entire outer absorbent member. To selectively render an otherwise pervious nonwoven material impervious, it can be coated or sprayed with water repellent materials, including those which form a film or can occlude openings. Waxes, acrylic coating materials, and silicone compounds that form gels or films, for example, may be used.

The topsheet can be treated with a variety of additives for odor control or for skin health and comfort, including anti-microbials, pharmaceuticals, emollients, aloe vera extract or vitamin E, and other known skin treatment compositions.

Additional Embodiments for the Backsheet

Because an impervious wicking barrier such as a polymeric film can be beneath the central absorbent member in many embodiments of the present invention, it is not imperative that the backsheet itself be absolutely impervious to prevent fluid from escaping from the central absorbent member. In fact, the backsheet beneath the central absorbent member in such cases can be a porous material such as a spunbond web having a clothlike feel or an embossed, microperforated film also having a clothlike feel. If the wicking barrier is wrapped around the outer absorbent member to prevent fluid leakage from the outer absorbent member to the backsheet, then all or part of the backsheet in the regions beneath the outer absorbent member may also be porous or clothlike. When the wicking barrier is suitably disposed beneath the central absorbent member and parts of the wicking barrier prevent liquid communicating contact between the outer absorbent member and the backsheet, then a major part or all of the backsheet may be liquid pervious and clothlike. Of course, a backsheet may have a clothlike feel and still be substantially liquid impervious, such as when a porous nonwoven web is laminated with a liquid impervious polymeric film.

Nevertheless, it is frequently desirable that the backsheet be substantially impervious, though it can be breathable to permit transmission of water vapor for comfort. The backsheet can be both breathable and stretchable, and specifically, can have biaxial stretch, as disclosed in commonly owned copending U.S. patent application Ser. No. 60/113,552, filed Dec. 23, 1998 by M. T. Morman et al.

The garment side of the backsheet (the surface contacting the garments of the wearer) can be provided with adhesives or other fasteners for securing the article to the undergarments or other clothing articles of the wearer. Any adhesive or glue used in the art for such purposes can be used, with pressure-sensitive adhesives being preferred. VELCRO® hook material, and other fasteners can be used.

Useful breathable materials can also be made by electrospinning technology, wherein a suspended polymer solution or melt is charged to a high voltage relative to a collection grid (see P. W. Gibson, H. L. Schreuder-Gibson and D. Rivin, "Electrospun Fiber Mats: Transport Properties," AIChE J., 45 (1)" 190–195 (Jan. 1999)). Electrical forces overcome surface tension and allow a fine jet of the polymer solution or melt to move toward the grounded or oppositely charged collection grid. The jet may splay into even finer fiber streams before reaching the target, and may be intercepted by a cloth or fabric that carries the fine fibers away. The dried or solidified fibers can have diameters of 40 nm (0.04 microns), though 200 to 500 nm fibers may be more common. The resulting materials can have small pores that permit vapor transport while inhibiting liquid transport, thus making useful breathable films.

Elastomeric fibers may also be used to create breathable, stretchable films. In one embodiment, a layer of electrospun nanofibers are deposited on film or nonwoven web, such as an apertured film or elasticized web, in order to provide a breathable moisture barrier layer attached to a layer providing other functionality such as texture, elasticity, integrity, or bulk.

Other Configurations and Additional Components

The absorbent articles of the present invention can be combined with other functional materials internally (as by adding material into the absorbent material or on the barrier material) or externally (as by joining with additional layers), including but not limited to odor absorbents, activated carbon fibers and particles, baby powder, zeolites, perfumes, fire retardants, superabsorbent particles, nonwoven materials, closed cell foams, electronic devices such as alarms indicating wetness or leakage and other wetness indicators, opacifiers, fillers, aerogels, sizing agents, antimicrobial agents, enzymes, ion exchange material, or enzyme inhibitors for prevention of damage to skin, including organophilic clays for inhibition of trypsin and other proteolytic enzymes as disclosed by A. A. Schulz and K. Floyds in U.S. Pat. No. 5,869,033, "Method of Preventing Skin Irritation Caused by Fecal Enzymes," issued Feb. 9, 1999.

A variety of specific compounds can be applied for prevention or control of odors, including chelating agents and cyclodextrins, such as those of U.S. Pat. No. 5,874,070, issued Feb. 23, 1999, and U.S. Pat. No. 5,429,628, issued Jul. 4, 1995 to Trinh et al.; aryl acetoxyethanoic acid compounds, as described in U.S. Pat. No. 5,874,071, issued Feb. 23, 1999; and triethyl cytrate and zinc ricinoleate.

For feminine care articles, tabs and wings can be added to the sides of the absorbent article. The wicking barrier can extend to the beginning of the tab or wing or beyond, though desirably the wicking barrier prevents lateral wicking of fluid into the region of the tab or wing. In one embodiment, the wicking barrier comprises a transverse section which extends laterally past the absorbent core to form a component of wings or tabs. Such a section can be an integral part of the wicking barrier or can be a second wicking barrier member in addition to a first wicking barrier member contained within the absorbent core.

For diapers and disposable training pants, a variety of additional components for body fit and comfort can be added. For example, diapers of the present invention preferably can further comprise side panels, elasticized leg cuffs, elasticized waistbands, and a fastening system preferably comprising a pair of securement members and a landing member. For bowel movement containment, the article may also be provided with flaps, void spaces in the absorbent core, raised barriers or dams, or any other systems for bowel movement containment known in the art.

A diaper can have a topsheet and a backsheet with length and width dimensions generally larger than those of the absorbent core. The topsheet and the backsheet extend beyond the edges of the absorbent core to thereby form the periphery of the diaper. While the topsheet, the backsheet, and the absorbent core may be assembled in a variety of well known configurations, several useful diaper configurations are described generally in U.S. Pat. No. 3,860,003 issued to Buell on Jan. 14, 1975 and U.S. Pat. No. 5,151,092 issued to Buell on Sep. 29, 1992.

The entire absorbent article may comprise extensible materials, including corrugated or foreshortened absorbent materials capable of stretch in one or more in-plane directions and an extensible topsheet and backsheet, and optionally an extensible or elastomeric wicking barrier. Several useful configurations for extensible articles are disclosed in U.S. Pat. No. 5,766,213, issued to Hackman et al., Jun. 16, 1998. The absorbent article, in addition to being extensible, can also be stretchable, as hereinafter defined.

Optionally, a surge layer can be disposed between the topsheet and the absorbent core, specifically above the central absorbent member, to enhance intake of fluid, particularly urine and particularly in absorbent articles intended for urine management such as diapers, training pants, or incontinence pads. The surge layer is typically a high-loft nonwoven web, such as a bonded carded web, of synthetic materials such as polyethylene or polypropylene, which does not retain liquid but helps to distribute it into the underlying absorbent core. Exemplary surge layers are described in U.S. Pat. No. 5,562,650, issued Oct. 8, 1996 to Everett et al. and U.S. Pat. No. 5,429,629, issued Jul. 4, 1995 to Latimer.

Means can also be applied to reduce the tendency of a pad or sanitary napkin to bunch or fold over onto itself during transverse compression. Wings, flaps, or tabs extending from the absorbent article in the crotch region can fold over the edge of undergarments of the wearer to provide better fit, stability, and leakage protection, and can reduce undesirable bunching of the article. Wings and related structures are taught in the U.S. Pat. No. 5,267,992, "Shaped Sanitary Napkin with Flaps," issued to K. J. Van Tilburg, Dec. 7, 1993 and World Patent Application 99/00093 "Absorbent Article with Multi-Layered Extensible Wings," R. W. Patterson et al., Jan. 7, 1999.

Methods of Making

Generally, automated equipment can be used similar to the production lines already used for production of sanitary napkins, diapers, and the like, with minor modifications to produce the present invention. Modular systems are especially preferred, wherein the various unit operations in the production line can be moved and replaced with other modules without necessitating a complete rebuild of a machine. Examples of useful machines and methods of using them for the production of absorbent articles are disclosed in U.S. Pat. No. 4,480,516 and U.S. Pat. No. 5,567,260, both of which are herein incorporated by reference.

The production line can include a hammermill for production of comminuted fibers, if fluff pulp is to be used, or absorbent material in roll form can be provided, including airlaid webs, coform, mechanically softened pulp sheets, tissue webs, and the like. Likewise, the nonwoven or film components of the absorbent article are also generally provided in roll form. Roll goods are unwound and cut to shape, using methods such as die cutting, slitters, or water jets, and the components placed in proper relationship one to another, typically with online bonding at selected regions provided by spray adhesive, contact with ultrasonic horns or heated embossing elements, or other bonding means known in the art. Components may be moved on continuous belts from one operation to another, and may be further transported with vacuum pick up shoes, jets of air, mechanical pincers, and the like.

For example, a web of airlaid material, coform, or a microstrained pulp sheet of width suitable for the absorbent core of an absorbent article may be unwound and slit into three strips, the middle strip desirably being wider than either of the two side strips. Alternatively, strips from three rolls of absorbent material may be unwound and brought into proximity to each other. The three strips are directed in the same direction, the machine direction, with two side strips spaced apart by a width approximately equal to or less than the width of the middle strip. The middle strip is elevated relative to the side strips, being guided and positioned by guiding means such as rolls, turning bars, foils, channels, pneumatic jets, vacuum slots or shoes, or the like. A web of barrier material, such as an embossed polyethylene film, a resin-impregnated or sized tissue web, or an apertured film or impervious web with spaced apart openings therein, is also unwound from a roll and is guided by guiding means to be beneath the elevated middle strip and above the side strips, traveling in the same direction. The barrier material web has a width greater than the predetermined final distance between the two outer strips (i.e., a width greater than the width of the central void in the assembled absorbent article), and desirably a width greater than the width of the middle strip, and can be at least as wide as the predetermined final width of the absorbent core or the absorbent article. The combination of the three strips and the moving web of barrier material converge into a low-pressure nip (e.g., peak pressure desirably less than about 50 kPa, more specifically less than about 8 kPa) or joining zone where the middle strip is brought approximately into the same plane as the outer strips or into contacting relationship therewith, with direct contact at least partially blocked by the presence of the wicking barrier. The middle strip may partially overlap the two outer strips, in which case the width of the central void space defined by the inner longitudinal sides of the outer strip would be less than the width of the central absorbent member. In this manner, an absorbent core is assembled having a central absorbent member, an outer absorbent member comprising two longitudinal strips, and a wicking barrier separating the central absorbent member from the outer absorbent member. (In specifying that the middle strip be elevated, it is understood throughout the body of this specification that that the same procedures could be applied upside down to create an upside down absorbent core, in which case the middle strip would be lower than the side strips.)

The three strips and the wicking barrier may then be joined to a section of backsheet material having a central rising member already disposed thereon or attached thereto, and the article may then be attached to a topsheet, or the central rising member may be sandwiched between a backsheet and the absorbent core, with the central rising member being centrally placed to be beneath the central absorbent member (the middle strip). Additional absorbent layers may be joined to the absorbent core, including an absorbent pocket or pouch comprising free-flowing materials such as about 1 gram to about 5 grams of eucalyptus nits wrapped in a liquid pervious encasement, which can be joined above or beneath the middle strip of absorbent material. A topsheet can then be attached to the backsheet and optionally adhesively attached to the absorbent core.

Alternatively, a central rising member such as a cut section of an "e"-folded web may be attached at periodic, spaced apart intervals to the body-side surface of the wicking barrier after it is unwound and before it is joined to the absorbent core, in which case the central rising member will be sandwiched between the wicking barrier and middle strip as the absorbent core passes through a nip or joining zone. In a less preferred embodiment, the wicking barrier could also be attached beneath the wicking barrier to its garment-side surface prior to contacting the backsheet. The absorbent core is sandwiched between a backsheet and topsheet, both of which can be provided in roll form also. Adhesive spray or beads, rotary ultrasonic or thermal bonding devices, and other joining means can be applied to joint the topsheet and backsheet to each other and to the absorbent core, if desired. The assembled article can be cut and provided with other components as needed.

In a related embodiment, three strips cut from one roll or brought together from two or more rolls of absorbent material are brought together as they travel in the machine direction. The three strips may reside on a moving belt or pass through an open draw. The three strips may be side by side in the same plane, or the middle strip may contact and overlap the two side strips, or the middle strip may initially be elevated relative to the side strips, but in any case, the middle strip must at least momentarily be elevated relative to the outer strips while the outer strips are on a moving belt or passing through an open draw. The central strip can be elevated by guide means such as a blast of air or application of vacuum, or by passing over a roll or other device. While the middle strip is elevated relative to the outer strips, a composite insert moving from the side is placed beneath the center strip and over the two side strips. The composite insert comprises a polymeric film having a width greater than the predetermined final distance between the two outer strips (i.e., a width greater than the width of the central void in the assembled absorbent article), and desirably a width greater than the width of the middle strip, and can be at least as wide as the predetermined final width of the absorbent core or the absorbent article. The composite insert desirably is at least as long as the crotch region of the article and can be at least as long as the absorbent core of the absorbent article being produced. Attached to the central portion of the composite insert is a central rising member desirably no wider than the central strip of absorbent material. For example, the composite insert can be a wicking barrier with an "e"-folded resilient, thin, absorbent fibrous web adhesively attached to the upper surface of the polymeric film. Placement of the composite insert under the central strip, such that the central rising member is above the film and directly beneath the central strip, helps establish a central absorbent member (the central strip) with a central rising member there beneath, the central absorbent member being isolated from the surrounding outer absorbent member (the two side strips of absorbent material) by a wicking barrier having a vertical component and a horizontal component. The central strip is then lowered by guiding means and/or depressing means, such as a guide roll, pneumatic jets, a soft, low pressure nip, and the like, and the assembly of three strips, the polymeric film, and the central rising member are placed on moving belt.

A cutter cuts the absorbent core to the proper length and it is then bonded to a backsheet such as a clothlike, breathable film that has been unwound from a roll, cut to the desired shape or length, and treated with adhesive to be joined to the absorbent core. A topsheet, also unwound from a roll, is joined adhesively, thermally, or ultrasonically, for example, to the article, particularly being attached to the backsheet at the periphery of the article. The topsheet and backsheet may then be cut together to define the proper shape for the article. Wings, adhesive tape strips, mechanical fasteners, cuffs, and the like may also be added using methods known in the art.

In one embodiment, an absorbent article according to the present invention can be created by placing a central rising member into a void in an outer absorbent member, followed by insertion of a central absorbent member. The void can be formed by airlaying materials over a template with variable permeability to cause lower basis weight in a central portion, or it can be created by mechanically compressing the central portion of an absorbent layer, or by mechanically removing absorbent material therefrom.

Optionally, a polymeric film to serve as a wicking barrier is placed over the void before addition of the central rising member or after addition of the central rising member. For example, a depression or stamped out region can be formed in an absorbent pad and the depression or stamped out region is lined with a meltblown barrier layer, a polymeric film, or other barrier material, whereafter an "e"-folded or "c"-folded coform web or flattened rubber tubular central rising member is placed over the polymeric film, after which a central absorbent strip such as an airlaid web is placed in the depression or stamped out region to serve as a central absorbent member having a wicking barrier to prevent lateral leakage toward the surrounding outer absorbent member. The barrier material may permit z-direction transport toward the outer absorbent member more readily than it permits lateral flow, as can be achieved, for example, by providing perforations in the middle of an impervious film whose unapertured sides block lateral flow into the surrounding outer absorbent member.

Related embodiments can be produced by simply stamping out the region of the absorbent core in a central region to define an outer absorbent member with a void therein. Under the outer absorbent member a liquid impervious polymeric backsheet is adhesively joined. A relatively flat central rising member is placed in the void above the backsheet, and then a central absorbent member such as a mat of fluff pulp is placed over the central rising member. A topsheet is joined to the article, either by fine adhesive spray over portions of the outer absorbent member and central absorbent member, and/or by adhesive connection to the backsheet along the periphery of the article. Desirably, excess width of the meltblown barrier layer beyond the width required to line the central void will result in a band of barrier material around the central absorbent member, which may offer a visual cue (especially if the meltblown is colored) of a protective ring around the central absorbent area and serve other valuable functions. The band can form a complete ring around the central absorbent zone, or can form longitudinal bands separating the sides of the article from the central target region.

High speed, automated equipment can be used to perform the manufacture of the article. A central absorbent member surrounded on all sides by an outer absorbent member generally must be placed into a central void with precision and good registration, which can be challenging at high speeds but still feasible. However, for ease of manufacture and reduced cost, the central absorbent member is an elongated strip that extends substantially the length of the article and is bound by the outer absorbent member only along the longitudinal sides of the central absorbent member, which sides desirably are substantially straight and parallel. In this case the central absorbent member can be a continuous strip which need only be registered laterally and cut at the ends to place it properly in the central void between an outer absorbent member comprising two discrete portions. In one embodiment, the outer absorbent member and central absorbent member are cut from a single strip of absorbent material, with the central portion (the central absorbent member) being momentarily lifted during manufacture to permit insertion of a central rising member there beneath and optionally insertion of the wicking barrier. However, the central rising member can be centered appropriately on an adhesive-coated backsheet before attachment to the absorbent members of the article, followed by addition of the topsheet, to provide an article within the scope of the present invention.

EXAMPLES

Several examples of absorbent articles were made with the materials listed in Table 1 below:

TABLE 1

Basic materials used in construction of absorbent articles for the Examples.

| Component | Manufacturer | Description |
|---|---|---|
| Topsheet | | |
| Spunbond material | Kimberly-Clark Corp. | 0.6 osy polypropylene spunbond web, "Delta" version, treated with 0.3% add-on of surfactant (described below), pin apertured |
| Surfactant treatment | ICI Americas, Inc. | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less. |
| Fluff | Kimberly-Clark Corp. | Coosa River CR54 debonded softwood pulp comminuted with a hammermill |
| Densified airlaid webs | | |
| Completed web | Concert Fabrication, Ltee | 90% softwood fibers and 10% binder fibers with overall densities of 0.1–0.2 g/cc. |
| Fibers | Weyerhaeuser Co. | NB-416: bleached southern softwood kraft |
| Binder fibers | Hoechst Celanese Corp. (Trevira Company) | Celbond #255: PET core, activated co-polyethylene sheath, 50/50 core/sheath ratio, concentric, 2.8 dpf, with T-255 fiber finish |
| Coform | Kimberly-Clark Corp. | 70% bleached kraft southern softwood, 30% polyethylene, basis weight of 228 gsm |
| Impervious wicking barrier | | |
| Polyolefin film, white | Edison Plastics Co. | A low density polyethylene, 18 gsm, opaque with added white pigment, about 1 mil |
| Pervious wicking barrier | | |
| Spunbond web | Kimberly-Clark Corp | 0.8 osy 2.7 denier, rose color, no surfactant |
| Backsheet | | |
| Polyolefin film | Edison Plastics Co. | A low density polyethylene, 20 gsm, rose color, 2 mil gauge after embossed with pattern MFST (male fine square taffeta), coated with contact adhesive on one side |
| Adhesive | National Starch and Chemical Co. | NS-34-5610, less than 15 gsm added, slot-coated, pinstripe pattern |
| Garment adhesive | National Starch and Chemical Co. | NS-34-5602, less than 45 gsm applied, slot coated, two 15 mm side lines of adhesive with a 19 mm space between them |
| Release paper | Akrosil Inc. | White base sheet, one side coated with silicone release agent, other side printed |

Example 1–3

Examples 1 through 3 were made generally according to FIGS. 20A and 20B, with exceptions noted below, and with the materials described in Table 1 unless otherwise noted.

In Example 1, the central absorbent member comprised a layer of a 250 gsm densified airlaid web with a density of 0.14 g/cc. The outer absorbent member was a densified airlaid web with a basis weight of 175 gsm and a density of 0.1 g/cc.

A central longitudinal slit 100 mm in length was made manually with a rotary blade knife in the central absorbent member.

The central rising member beneath the central absorbent member was a section of densified airlaid web with a basis weight of 175 gsm and a density of 0.1 g/cc, cut to dimensions of 110 mm by 70 mm and folded with two creases normal to the long direction and evenly spaced apart to yield an "e"-folded web with a width of about 40 mm and a length of 70 mm. The creases defining the folds were oriented in the longitudinal direction of the article so that the e-fold shape of the central rising member would be evident in a transverse cross-section, such as is shown in FIG. 20B.

The final pad was 238 mm long and 86 mm wide. The outer absorbent member had external dimensions of 218 mm in length and 65 mm in width. Referring momentarily to FIG. 20A, the first ply 132 of the wicking barrier 24 defined a horizontal ledge around the upper layer 50 of the central absorbent member 18 that spanned a transverse width (edge to edge width, from one longitudinal side to the other, including the width of the upper layer 50) of 51 mm and a longitudinal length of 204 mm. The second ply 134 served as an extended barrier that was 86 mm wide and 120 mm long. The central absorbent member (labeled 18 in FIG. 20A) was 196 mm long and 43 mm wide. (All dimensions are based on the width as seen from a top view; the actual width of the plies in the wicking barrier prior to assembly in the article will be longer.)

The arcuate slits in the upper layer of the central absorbent member were 74 mm long and were substantially as shown in FIG. 20A. The spunbond topsheet with floral pin aperturing (0.081 inch pins spaced about 0.4 mm apart in a continuous pattern over the full length of the pad but only in the central 38 mm of the transverse width) was held in place by light adhesive. Likewise, adhesive joined the backsheet to the wicking barrier components where contact occurred. The backsheet was provided with adhesive strips and release paper for attachment to the garment. The garment-contacting adhesive was provided in two 15-mm wide, 190-mm long longitudinal strips leaving the central 19 mm wide region about the longitudinal centerline free of adhesive. In the crotch region, the width of the adhesive was extended outward an additional 10 mm toward the outer longitudinal sides (reaching the region directly underneath the outer longitudinal sides of the outer absorbent member) such that a 190 mm long rectangular section of adhesive on either side of the longitudinal centerline had a width of 25 mm, still leaving the central 19 mm free of adhesive. The placement of adhesive bands was intended to promote better control of deformation of the pad in use to better establish a W-fold geometry.

When the resulting pad has grasped along the longitudinal sides in the crotch region and laterally compressed, the central absorbent member deflected upward in the crotch region, indicating the potential for good body fit in use. The overall shape of the deformed pad in a transverse cross-section was roughly W-shaped. Vertical deflection in the central portion of the pad was enhanced relative to a similar pad made without the central rising member.

Examples 2 and 3 were generally made according to Example 1, except that the outer rim of the pad was trimmed along the longitudinal sides to give the pad an overall width of 71 mm and to give the extended barrier material a width of 71 mm as well. In Example 2, the central absorbent member was a densified airlaid web with a basis weight of 175 gsm instead of the 250 gsm web of Example 1. The density of the central absorbent member was 0.1 g/cc. The central rising member was an e-folded web of a densified airlaid web having a density of 0.14 g/cc. In the e-folded central rising member, approximately 1 cm space was provided between the terminal ends (40 and 42 in FIG. 5) of the central rising member and the respective opposing longitudinal sides (32' and 32", respectively, in FIG. 5), providing space for significant lateral sliding of the lower portions (36 and 38 in FIG. 5) of the central rising member during lateral compression, and resulting in an e-folded cross-section better characterized by that of the central rising member 30 in FIG. 5 than that of FIG. 20B.

In Example 3, 228-gsm coform was used for the outer absorbent member, the central absorbent member, and the central rising member, which was folded as in Example 2. The longitudinal ends of the central rising member were rounded to have a radius of curvature at the 4 corners of the folded central rising member of about 1 cm.

As with Example 2 and 3, good upward deflection of the central rising member was observed during lateral compression of the article from the longitudinal sides. The additional space between the terminal ends and the longitudinal sides of the central rising member promoted somewhat greater upward deflection in Examples 2 and 3 than in Example 1.

Example 4

Figure 22:
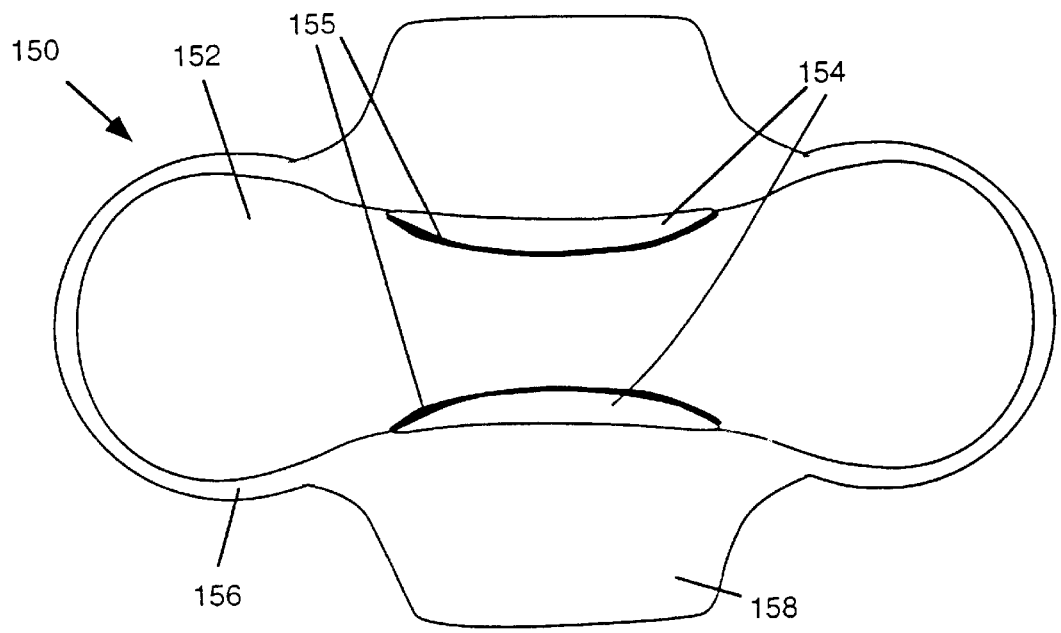
FIG. 22 depicts a commercial maxipad.

Example 4 was made using a commercially available maxipad, the ALWAYS® Maxi with Wings with a DRI-WEAVE™ apertured film cover, manufactured by Procter and Gamble (Cincinnati, Ohio) and taken from a package of 20. This product also features "side channels" which are crescent-shaped, highly densified regions along the longitudinal sides in the crotch region joined to the central high bulk, high thickness fluff pad that extends across the longitudinal length of the article. According to the package, the product was made under one of more of the following U.S. Pat. Nos. 4,342,314; 4,463,045 4,556,146; 4,573,986; 4,589,876; 4,687,478; and 5,267,992. FIG. 22 depicts the original pad 150 as purchased, showing a central high-bulk fluff pad region 152, densified outer zones 154 having a lower basis weight than the central region 152, with highly densified embossment lines 155 joining the central region 152 to the densified outer zone 154. The topsheet (not shown) joins the backsheet to form an outer rim 156, which is also attached to wings 158.

Figure 23:
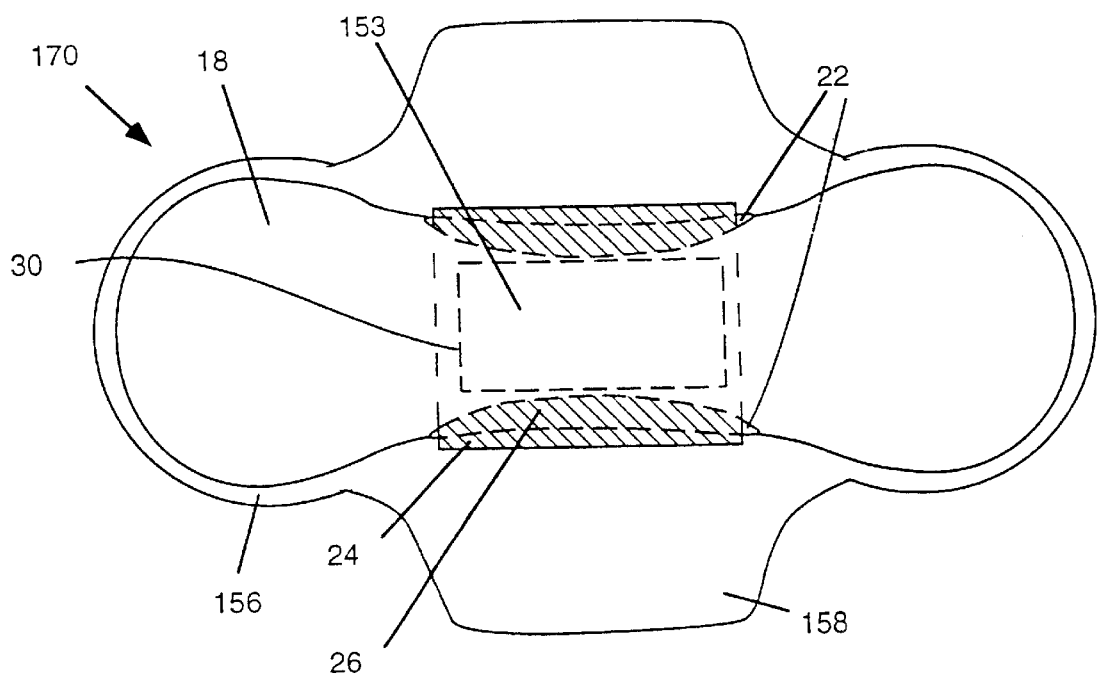
FIG. 23 depicts the modified maxipad of FIG. 22 after a wicking barrier and central rising member have been added, according to the present invention.

To convert the commercial article into a pad with a wicking barrier separating a central absorbent member from an outer absorbent member, the apertured film topsheet was slit near the outer perimeter of the wings 158 of the article, and by hand the densified outer zones 154 were separated from the central high-bulk region 152 by tearing along the embossment lines 155. Then a 20 gsm 1-mil pink poly film with a width of 5 cm was pulled into the slit and placed under the central high-bulk region 153 such that it covered the top surfaces of both of the densified outer zones 154 but went completely beneath the central high-bulk region 153 in the crotch region. The poly film was trimmed to just slightly extend past the outer perimeter of the densified outer zones 154, as depicted in FIG. 23, which follows the numbering scheme of FIG. 22 but shows that the article 170 has a wicking barrier 24 comprising the poly film resting on the body-side surface of the densified outer zones (154 in FIG. 22), which now serve as an outer absorbent member 22. In this embodiment, the outer absorbent member 22 has first and second portions with a void therebetween which effectively has received a central absorbent member 18 (formerly 152 in FIG. 22) comprising the central high-bulk region 153. The wicking barrier 24 has a horizontal component 26 on the outer absorbent member 22 and spans a vertical distance of about 5 mm from the top of the outer absorbent member 22 to the backsheet (not shown) beneath the central high-bulk region 153 in the central portion of the article (the target zone or crotch region).

This modification of a commercial product can effectively reduce leaking as fluid is wicked or otherwise transported from the high-bulk region 153 to the outer absorbent member 22, and can reduce bending stiffness and enhance the folding geometry of the article when worn. Similar modifications may be made with other commercial articles, such as pantiliners. The body fit performance of the modified article can be further enhanced by placing a central rising member 30 beneath the central absorbent member 18 as shown, with the central rising member 30 being placed immediately above or below the wicking barrier 24. The central rising member 30 desirably is a thin, stiff resilient member as shown in FIG. 18 or FIG. 19.

Examples 5–11

Examples 5–9 describe absorbent articles made to demonstrate the advantages of a wicking barrier between central absorbent member and an outer absorbent member. Though a central rising member was not placed under the central absorbent member in Examples 5–9, any of the central rising members described herein could be combined with the following examples to further improve body fit.

Figure 24:
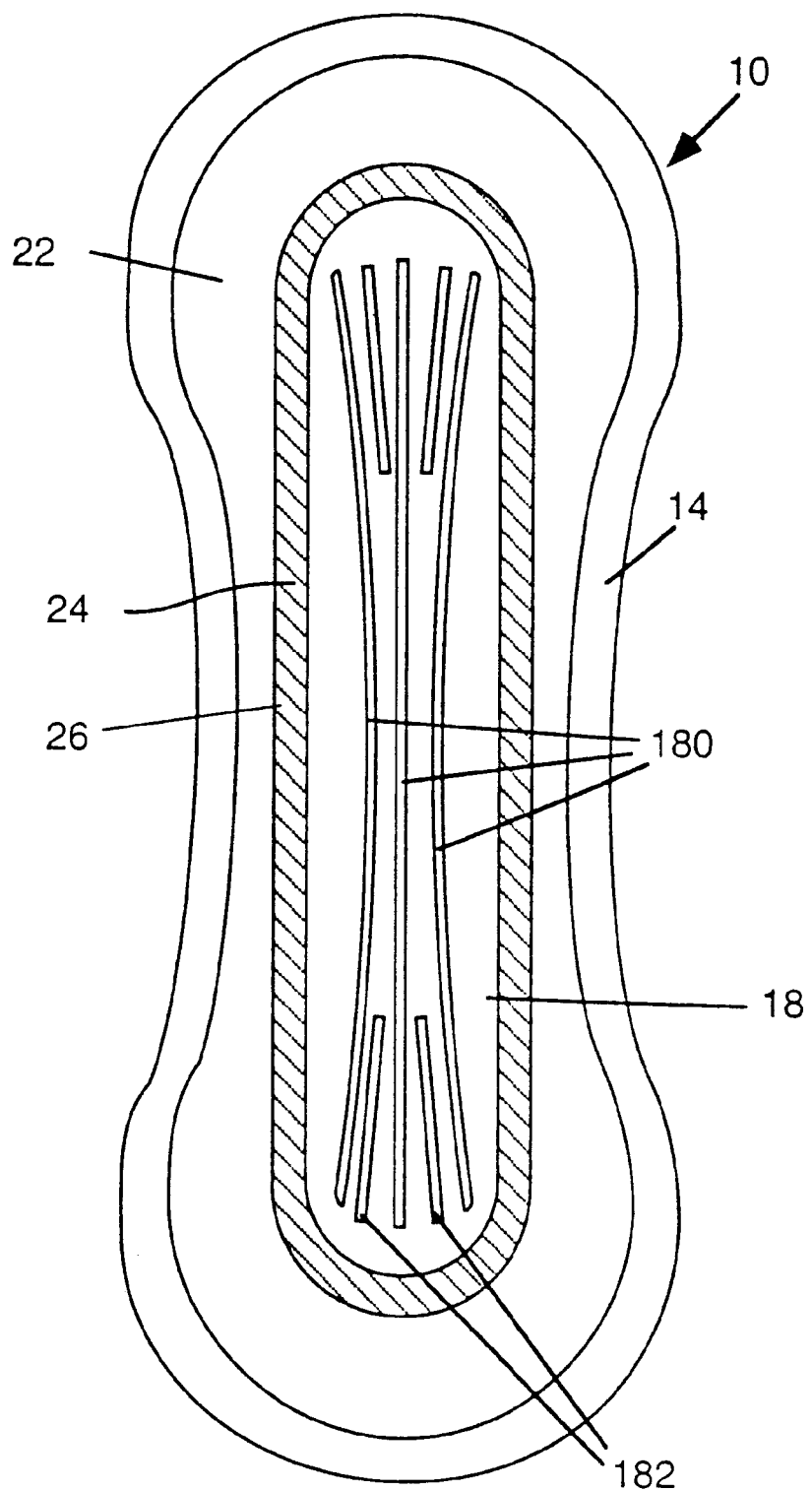
FIG. 24 depicts a top view of an exemplary absorbent article comprising a wicking barrier and embossments in a central absorbent member.

Example 5 was made to have a top view appearance according to FIG. 24. FIG. 24 depicts an absorbent article 10 having a central absorbent member 18 surrounded by a wicking barrier 24 and an outer absorbent member 22. The absorbent members 18, 22 are enclosed by an underlying backsheet 14, with larger dimensions than the outer absorbent member 22 to form a rim therearound, and a topsheet (not shown) which is attached to the backsheet 14 at the rim. Optionally, the central absorbent member 18 can be provided with embossed lines as shown in FIG. 24 comprising three long lines 180 and four short lines 182 each about 2 mm wide and approximately 0.4 mm deep.

Example 5 was a control pad made without a vertical component to the wicking barrier 24 but with a horizontal component 26; i.e., with a polymeric film disposed horizontally between two superposed absorbent layers. Thus, in Example 5, the horizontal component 26 of the wicking barrier 24 is the exposed horizontal component of a substantially horizontal barrier (the impervious wicking barrier of Table 1) which lies in a plane between an upper central absorbent member 18 and an underlying outer absorbent member 22, which is merely a planar absorbent member which lies beneath the central absorbent member 18 (in other examples according to the present invention, the outer absorbent member 22 has a central void into which receives the central absorbent member 18).

In Example 5, a 175-gsm airlaid densified web (as described in Table 1) served as the lower layer of the absorbent core, i.e., as the outer absorbent member 22 but without a central void. The 175-gsm airlaid outer absorbent member 22 was cut to a dumbbell shape with a length of about 21.5 cm and a width at the transverse centerline of about 6 cm. The dumbbell-shaped outer absorbent member 22 was placed on the backsheet 14 (as described in Table 1) comprising a polymer film provided with contact adhesive. Over the central portion of the outer absorbent member 22 of the control samples was placed a cut rounded rectangular section of spunbond film (the same material as the pervious wicking barrier of Table 1) to serve as a horizontal wicking barrier 24. The horizontal wicking barrier 24 had a length of 20.3 cm and a width of 4.7 cm. Above the horizontal wicking barrier 24 was placed a rectangular rounded central strip of a densified airlaid web having dimensions smaller than the cut spunbond film (18.7 cm long and 3.7 cm wide). The densified airlaid strip was as described in Table 1, with a density of about 0.1 g/cc and a basis weight of about 175 gsm. This central strip was provided with the curved embossing lines depicted in FIG. 24 while the underlying outer absorbent member 22 remained unembossed. A slit about 17 cm long was provided through the longitudinal center of the central strip in the longitudinal axis. The spunbond topsheet as described in Table 1 was then placed over the entire article 10, with edges extending well beyond the outer absorbent member 22. The laminated structure was then cut with a dumbbell-shaped die having dimensions greater than the outer absorbent member 22 (24.4 cm long, 8 cm wide at the transverse centerline) to provide a rim of backsheet material and cover material around the outer absorbent member 22 in an absorbent article 10 having good integrity provided in part by the contact adhesive on the polymeric film. After cutting, the pad was heat-embossed to provide several embossing lines 180, 182 in the central strip of the pad as shown in FIG. 24.

Example 5 could be further improved according to the present invention by inserting a central rising member such as an e-folded, resilient web of tissue, coform, or a nonwoven beneath the central absorbent member, either immediately above the wicking barrier 24, immediately below it, or even between the underlying outer absorbent member 18 and the backsheet 14 provided that the central rising member is centrally positioned in the crotch region of the absorbent article 10. The horizontal wicking barrier 24 desirably would be provided with a central hole or apertures to permit fluid in the central absorbent member 18 to pass into the underlying outer absorbent member 22 prior to oversaturation of the central absorbent member 18. Desirably, the wicking barrier 24 is a film with apertures beneath a portion of the central absorbent member 18 but substantial free of apertures in the exposed horizontal component 26 of the wicking barrier 24. In related embodiments, the central absorbent member 18 may have a longitudinal length equal to that of the underlying outer absorbent member 22, with a wider longitudinal strip of wicking barrier material beneath the central absorbent member 18, the wicking barrier 24 having apertures or other openings in the central portion thereof to permit downward wicking from the central absorbent member 18 after it has been partially saturated, the wicking barrier 24 serving primarily to prevent contact between the longitudinal sides of the article and the central absorbent member 18 when the article is worn. Desirably, the wicking barrier 24 in the target region of the article extends to the longitudinal sides thereof.

For Examples 6 to 9, feminine pads according to the present invention were made generally following the procedures above for Example 5, with the exceptions that 1) a central region of the outer absorbent member was removed by a die cutting operation to provide a central void in the outer absorbent member having substantially the same dimensions as the central absorbent member (about 18.7 cm long and 3.7 cm wide); 2) a cut polymer film (the rose-colored impervious wicking barrier of Table 1) die cut to be a rounded rectangle 20.3 cm long by 4.7 cm in width was placed over the central void, replacing the similarly shaped spunbond web of Example 5, thus serving as a barrier material for a wicking barrier; and 3) a an absorbent insert having a shape and dimensions essentially the same as the central void was placed over the cut polymer film to define a central absorbent member in the void surrounded by the remaining portions of the outer absorbent member.

After the topsheet was attached and the entire article was die cut to provide a sealed article having a rim of backsheet and topsheet material surrounding the outer absorbent member, a loop of the colored barrier material was visible through the translucent topsheet (the horizontal component of a vertical wicking barrier). The articles were also heat embossed as with the control to provide several substantially longitudinal embossment lines in the central absorbent member.

Several different combinations of material were used to produce the central absorbent member. For most examples, the lower layer of the central absorbent member consisted of the 175 gsm outer absorbent member material that was cut out of the outer absorbent member while providing a central void therein.

In Example 6, the central absorbent member comprised an upper layer consisting of a 250-gsm densified airlaid mat (as described in Table 1) having a density of 0.14 g/cc and a lower layer consisting of the cut-out portion from the 175-gsm airlaid material of the outer absorbent member having a density of about 0.1 g/cc which was previously removed to provide a central void. As with the control sample (Example 5), the upper layer of the central absorbent member was embossed and provided with a longitudinal slit.

In Example 7, the upper portions of the central absorbent member comprised two layers of an uncreped through-air dried tissue of spruce BCTMP pulp each having a basis weight of 30 gsm and added permanent wet strength agent (Kymene added at about 50 pounds per ton of fiber), molded onto a Lindsay Wire T-116-3 through-air drying fabric and produced with about 27% rush transfer onto a Lindsay Wire T-216-3 transfer fabric (i.e., 27% differential velocity in going from a forming fabric to the textured transfer fabric, from which it was then transferred to the through-drying fabric), according to the teachings of Chen et al. in commonly owned U.S. patent application Ser. No. 08/912,906, "Wet Resilient Webs and Disposable Articles Made Therewith," filed Aug. 15, 1997. The tissue has a bulk of about 33 cc/g (density of 0.03 g/cc) and a wet:dry tensile strength ratio of 43%. Beneath the uncreped tissue layers was the 175 gsm densified airlaid web of the outer absorbent member (0.1 g/cc density) which had been previously cut out from the outer absorbent member.

Example 8 followed Example 7 except that three layers of the uncreped tissue were used in place of the two layers from Example 7 to create the upper layers of the central absorbent member above the 175 gsm airlaid lower layer. The three layers were calendered to provide the same thickness together as the two layers did in Example 7.

In Example 9 a 200-gsm layer of softwood fluff pulp (described in Table 1) with a diamond embossment thereon was placed above the 175 gsm densified airlaid material of the outer absorbent member to form the central absorbent member. No central longitudinal slit was provided in the upper layer of the central absorbent member. The fluff pulp was prepared by splitting a 400-gsm pad of fluff. The formerly interior portion of the 400 gsm appeared substantially uniform, while the opposing surface (formerly an exterior surface of the 400 gsm pad) showed the diamond embossing pattern clearly. The latter side was placed downward, toward the backsheet, in assembling the pad.

In Example 10 a maxipad was prepared with an unembossed 600 gsm fluff pulp pad (described in Table 1) as the absorbent material for both the outer absorbent member and the central absorbent member. The cut out portion from the central void (same dimensions as in previous Examples) was lined with polymeric film (the colored impervious wicking barrier of Table 1) having a width of about 5.5 cm instead of 4.7 cm as in Examples 5–9, and then replaced in the void, with the polymeric film defining a vertical wicking barrier between the central absorbent member and the surrounding outer absorbent member. In this case, the central absorbent member consisted essentially of the same material as the surrounding outer absorbent member.

In Example 11, a control maxi pad was produced using an unembossed 600 gsm fluff pulp mat with no wicking barrier and with no central void provided therein.

Testing of Examples 5–9 was done using insults of saline solution containing a small quantity of blue dye. In one group of tests, a 15 ml insult of the blue fluid were added to the center portion. In another group of tests, the insult was 7 ml. Both insults were applied over a period of about 15 seconds. In both cases, some of the blue fluid escaped from the edges of the central strip in the control pad of Example 5, wetting the surrounding outer absorbent member. For both the 7 ml and 15 ml insult tests, the pads with wicking barriers held the fluid in the central absorbent member without substantial spread of the blue liquid into the surrounding outer absorbent member, thus achieving center-fill performance.

Testing with the maxipads of Example 10 and 11 by insulting blue saline solution into the center of the pad showed that the wicking barrier in Example 10 was successful in preventing fluid from migrating toward the longitudinal sides of the sides compared to Example 11.

Under light compression by hand (estimated at about 0.1 psi) of the wetted pads, the pads of the present invention also showed improved ability to retain their fluid in the central absorbent member compared to the control pad of Example 5.

Central rising members could be placed in the crotch region of any of Examples 5–11 for improved body fit. Further, shaping lines could be provided in the central absorbent member for improved control over deflection toward the body during inwardly lateral compression.

Example 12

Example 12 is a maxipad with fluff pulp as the primary absorbent material made according to Example 10, with the exception that the central absorbent member comprises a strip of a dual-zoned web made according to the principles taught by Chen et al. in Ser. No. 08/997,287, "Dual-zoned Absorbent Webs," filed Dec. 22, 1997. Specifically, a 40 gsm web of uncreped through-air dried tissue made from bleached kraft eucalyptus fibers (Aracruz, Brazil) was textured on a three-dimensional Lindsay Wire T-116-1 through-drying fabric with about 15% rush transfer, resulting in a bulk of about 14 cc/g, largely due to the three-dimensional texture of the web. Kymene 557H wet strength agent (Hercules, Wilmington, Del.) was added at a level of about 7 kg/ton dry fiber. The uppermost portions of the dried web that had contacted the through-drying fabric (the wire-side) were coated with Dow Corning DAP® Silicone Auto/Marine Sealant applied at a total area-averaged level of 5 gsm (estimated to be about 12 gsm on the peaks that received the material). After curing, the coated side of the tissue had a soft, rubbery feel due to the rubbery silicone material being on the highest portions. Though the silicone is impervious and hydrophobic, the coated web is still hydrophilic and able to take liquid in readily due to the untreated lower portions of the web.

The dual-zoned web was provided with an array of spaced apart apertures, each about 0.5 cm apart from its nearest neighbor, each aperture having a diameter of about 0.5 mm. The apertures were stamped by hand into the web, with stamping occurring from the coated side toward the uncoated side. Based on tests with egg white solution as a menses simulant, the apertures were found to be helpful in transporting viscoelastic material through the dual-zoned web to the underlying absorbent material for an improved dry feel on the surface of the article.

A strip of the silicone-treated textured uncreped tissue web was cut to the same size as the central absorbent members of previous examples and placed over the cut-out section of 600 gsm fluff pulp within the central void lined with the wicking barrier (rose-colored impervious wicking barrier as in Table 1). The coated side of the treated web was facing up (toward the body side). To permit the treated dual-zoned web to serve as a cover material as well as an intake layer, a rounded rectangle 3.3 cm wide and 10.5 cm long was cut out of the spunbond web normally used as a topsheet, such that the rounded rectangular hole in the topsheet was centered over the dual-zoned web of the central absorbent member, thus providing direct access to permit the dual-zoned web to touch the body of the wearer and serve as a dry-feel cover material and intake material. The dual-zoned web cover materials of the aforementioned patent application of Chen et al. permit a cover to provide the dry feel of a hydrophobic plastic film while also providing intrinsic hydrophilicity and softness.

The resulting maxipad was thus composed of 600 gsm fluff pulp with a rose-colored wicking barrier surrounding a cut-out section of the fluff pulp, providing a vertical barrier and a visible horizontal ledge around the central absorbent member. The ledge and longitudinal sides of the dual-zoned web were covered by the spunbond topsheet, but most of the area of the dual-zoned web was exposed through the hole cut in the topsheet. Adhesive on the topsheet held the edges of the hole in place on the dual-zoned web.

Example 13

Example 13 was made according to Example 6 except that the central absorbent member was entirely replaced with about 3.3 grams of loose "nits" made of bleached kraft eucalyptus fibers which had been mechanically curled and dispersed to form small dense flocs about 1 mm in diameter. The nits were prepared by taking about 20 grams of dry eucalyptus pulp that had been curled in a Maule disperger, than moistening the pulp to a consistency of 20% and beating in a Hobart mixer for 1.5 hours to create dense nits. The moist nits were then spread out on a surface and air dried. The dry, loose nits were placed over the wicking barrier film inside the void of the outer absorbent member and covered with a topsheet, which served to hold them in place.

Example 14

Example 14 was made according to Example 6 except that the topsheet was pleated to provide longitudinal loops of cover material directly over the edge of the central absorbent member. The air-filled loops were heat sealed with an Impulse Sealer by American Electronics, designed for sealing plastic bags. The heat-sealed loops were thus rendered largely impervious and slightly glossy in appearance, though not uncomfortably stiff. The longitudinal loops raised about 0.4 cm from the surface of the absorbent article.

Central rising members could be placed in the crotch region of any of Examples 12–14 for improved body fit.

Example 15

Figure 25A:
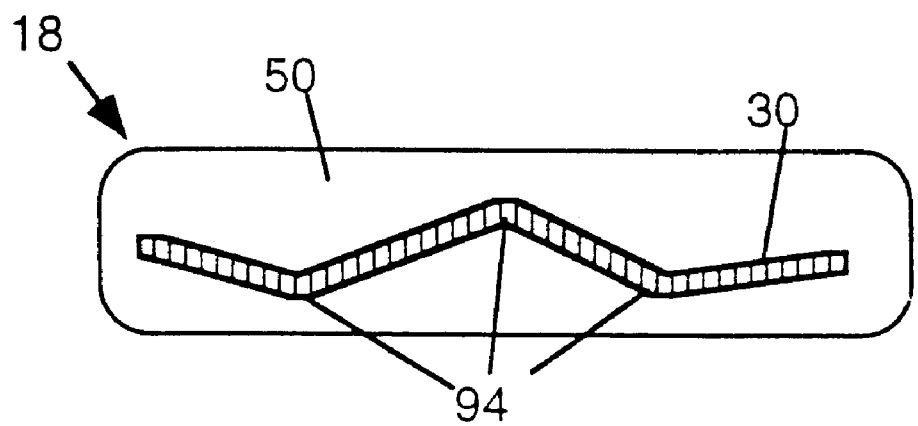
FIGS. 25A–25C depict cross-sections of three central absorbent members with internal central rising members.
Figure 25B:
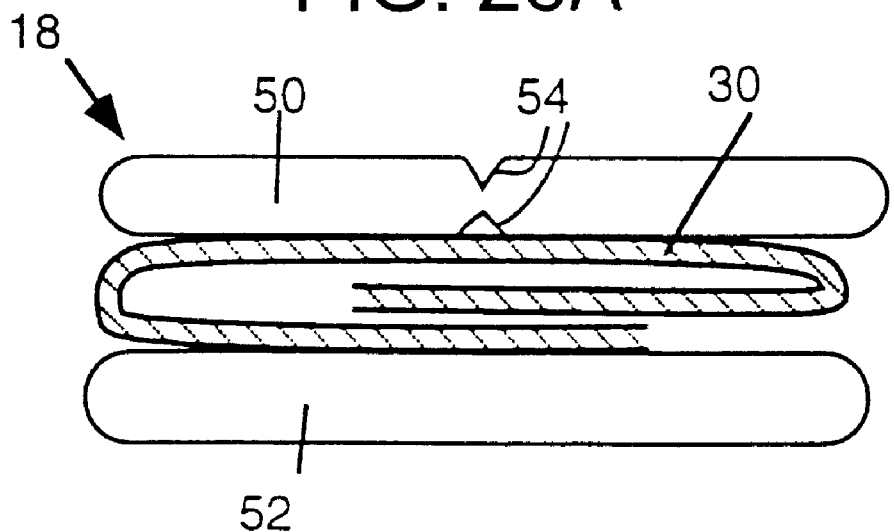
Figure 25C:
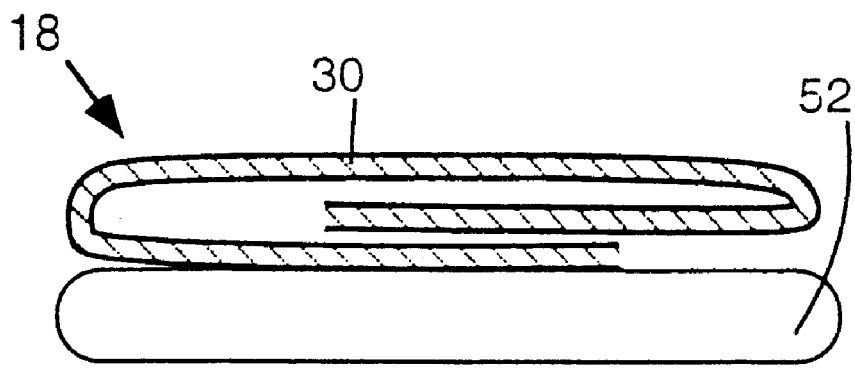

FIGS. 25A–25C provide illustrative embodiments of a central absorbent member 18 with a central rising member 30 disposed therein. In each of these embodiments, the garment-side (lower) surface of the central rising member 30 is above the garment-side (lower) surface of the central absorbent member 18. The central absorbent member 18 comprises a fibrous upper layer 50 and, in FIGS. 25B and 25C, a fibrous lower layer 52. In FIG. 25A the central rising member 30 comprises a flexure-resistant section of material, such as a thermoplastic deformation element or a densified airlaid web, with scoremarks or hinge elements 94 to promote a W-shaped fold upon lateral compression. FIGS. 25B and 25C show the central rising member 30 as an "e"-folded web of material. In FIG. 25B, notches 80 or scoremarks in the upper layer 50 permit enhanced upward deflection of the central absorbent member 18. In FIG. 25C, the absorbent central rising member 30 is the uppermost absorbent component of the central absorbent member 18. Such central rising members within a central absorbent member can be provided with perforations to reduce resistance to incoming fluid flow, particularly if the central rising member is non-absorbent. Perforations in the central rising member desirably are from about 0.2 to 2 mm in diameter and can occupy from 5% to about 30% of the surface area of the central rising member.

Example 16

Figure 26:
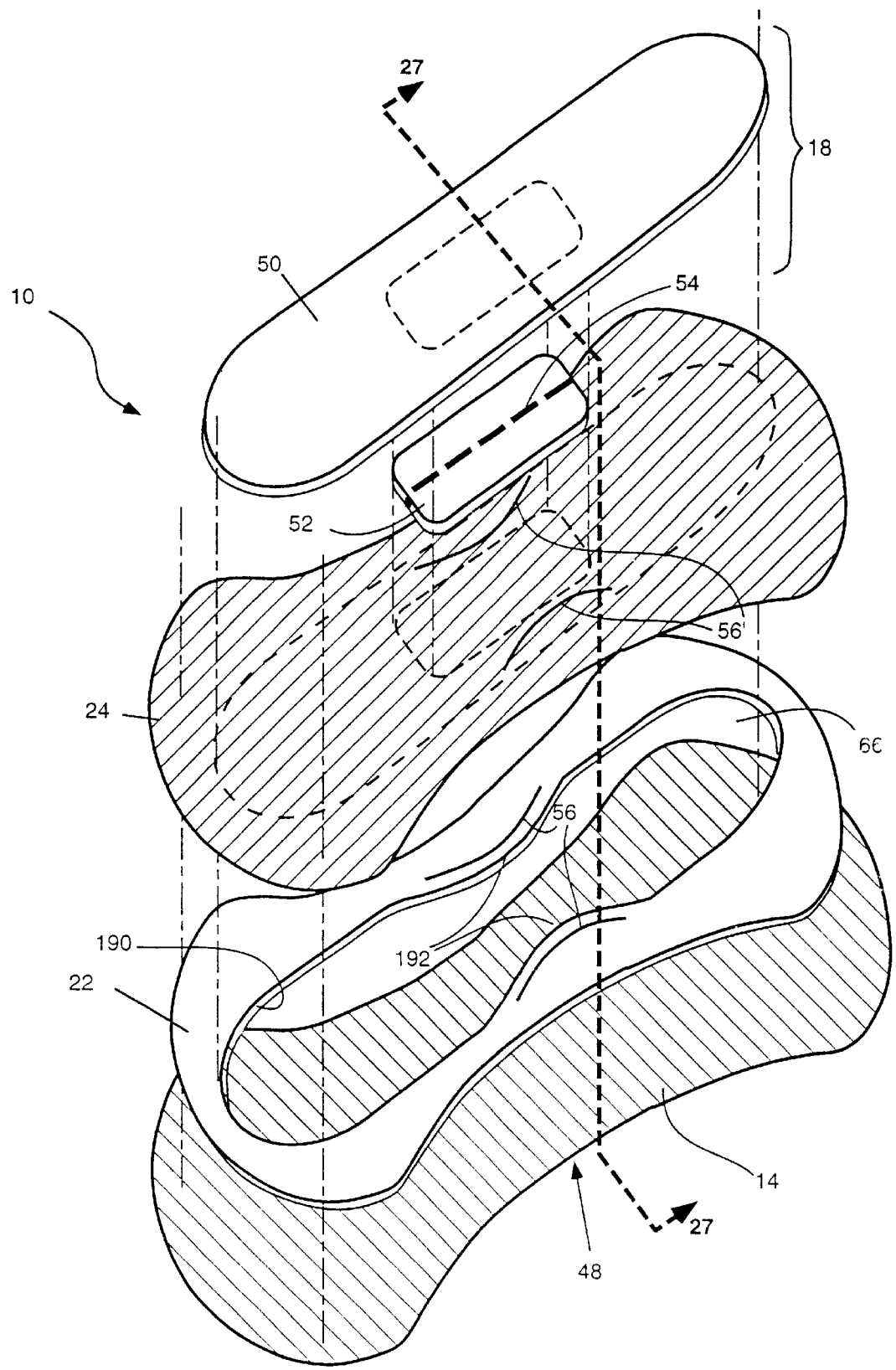
FIG. 26 is an exploded view of an absorbent article having an outer absorbent member with a central void, a wicking barrier, and a two-layered central absorbent member predisposed to flex vertically upward.
Figure 27:
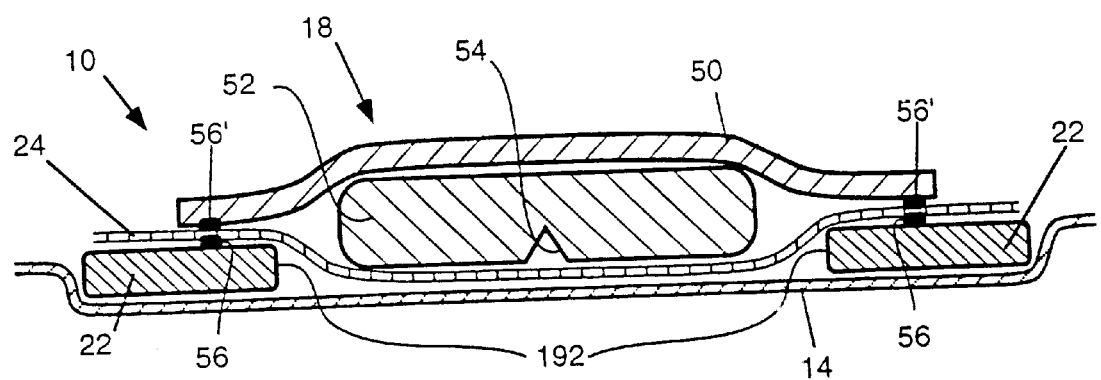
FIG. 27 is a cross-section of the absorbent article of FIG. 26.

FIG. 26 depicts an illustrative hypothetical example of an absorbent article 10 according to the present invention, wherein a dogbone-shaped polymeric backsheet 802 is attached to a superposed section of absorbent material forming an outer absorbent member 22 having a central void 66 passing completely through the outer absorbent member 22 to define inner walls 190. The topsheet (not shown) has been removed for clarity. Above the outer absorbent member 22 is a thin, flexible wicking barrier 24, which has in-plane dimensions larger than the outer absorbent member 22. The wicking barrier 24 can be provided with apertures or holes (not shown). The wicking barrier 24 rests below the centrally located lower layer 52 of the central absorbent member 18. The lower layer 52 is provided with a longitudinal groove defining a shaping line 54 to promote upward folding during lateral compression. Above the lower layer 52 is a flexible upper layer 50 of the central absorbent member 18 which fits inside the central void 66 of the outer absorbent member 22 except in the crotch region 48, where the longitudinal sides of the upper layer 50 overlap with the overlap regions 192 of the outer absorbent member 22, separated still by the wicking barrier 24. Preferably, the overlap regions 192 do not overlap with the lower layer 52 of the central absorbent member 19.

Desirably, bands of adhesive 56 on the body-side surface of the outer absorbent member 22 in the crotch region 48 join the overlap regions 192 to the wicking barrier 24, and additional adhesive bands 56' between the wicking barrier 24 and the upper layer 50 further join the overlap regions 192 to the longitudinal sides of the upper layer 50.

A cross-section of the article 10 along the transverse centerline is shown in FIG. 27, again without a topsheet. The upper layer 50 deforms around the narrower lower layer 52, making the upper layer 50 predisposed to flex upward when the article 10 is compressed laterally from the sides. The shaping line 54 in the lower layer 52 of the central absorbent member 18 also promotes upward deflection under lateral compression.

The wicking barrier 24 spans both a horizontal distance on the surface of the outer absorbent member 22 and vertical distance between the lower layer 52 and the outer absorbent member 22. The lower layer 52 penetrates a distance into the central void 66 of the outer absorbent member 22. When laterally compressed, the outer absorbent member 22 and the longitudinal sides of the upper layer 50 are expected to deflect upward at the longitudinal sides and downward closer to the longitudinal centerline (i.e., forming a valley fold at the juncture between the outer absorbent member 22 and the lower layer 52), while the central portion of the article including the lower layer 52 and the overlying portion of the upper layer 50 will deflect upwards toward the body along the longitudinal centerline (i.e., forming a mountain fold or inverted-U shape along the longitudinal centerline). The absorbent article 10 is an example of an article with a central rising member inherently within the central absorbent member 18.

A variety of similar articles can be constructed according the present invention in which a portion of the central absorbent member fits within a central void of the outer absorbent member but wherein the central absorbent member overlaps with the outer absorbent member in the crotch region, and particularly wherein the central absorbent member comprises a wide upper layer and a narrower lower layer wherein the upper layer is predisposed to flex upwards during lateral compression, and wherein the crotch region of the absorbent article tends to deform during use in a shape providing excellent body fit and good leakage control.

Example 17

Figure 28:
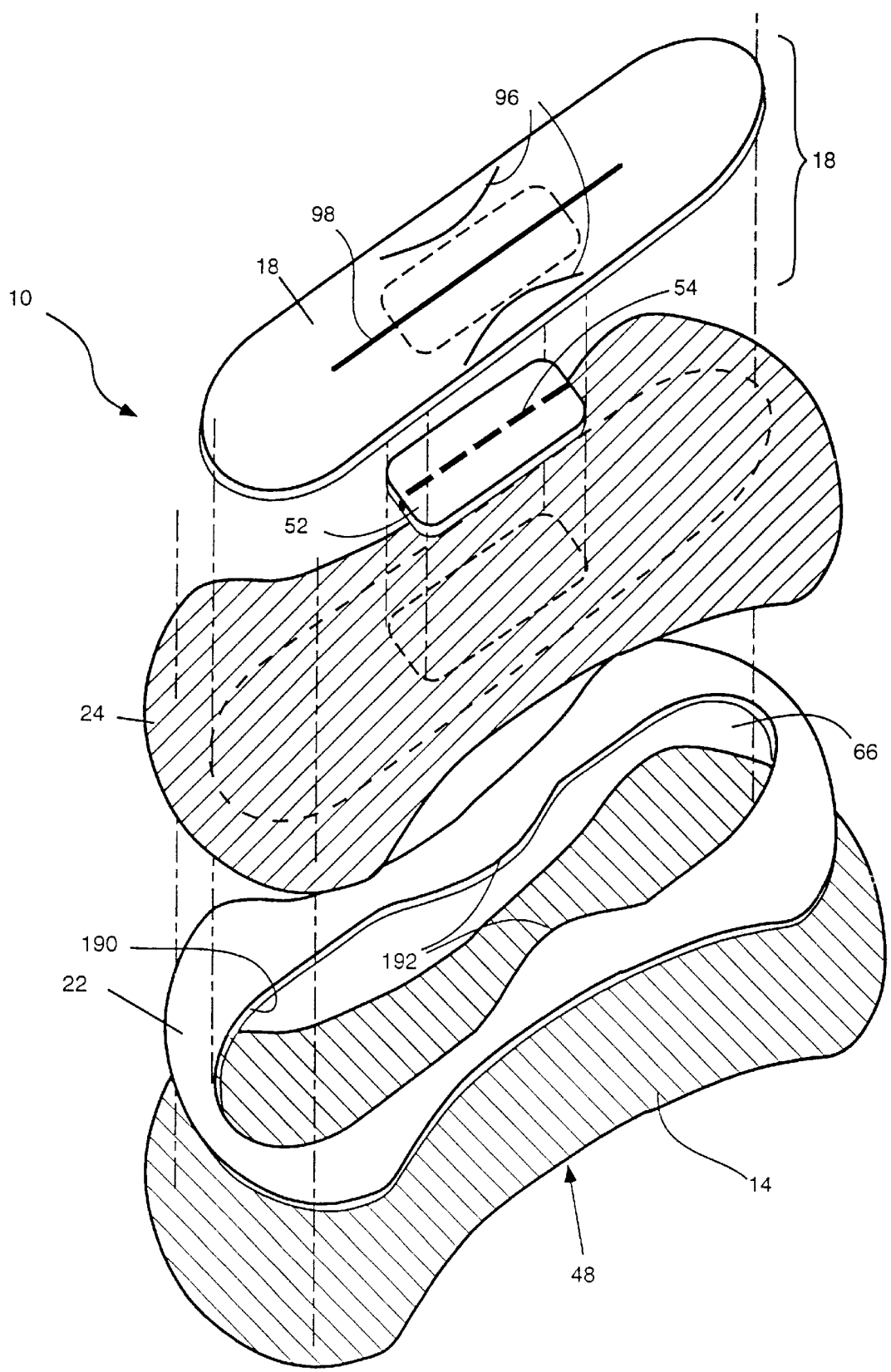
FIG. 28 is an exploded view of an article similar to that of FIG. 26 with shaping lines in the upper absorbent member.

Example 17 was constructed substantially according to FIG. 28, which is similar to FIG. 26 except that arcuate bands of adhesive 56, 56' in FIG. 26 have been replaced with adhesive (not shown) generally distributed on both sides of the wicking barrier 24, and the upper layer 50 of the central absorbent member 18 has been provided with arcuate crease lines 96 and central longitudinal line 98 (a shaping line) in the form of slits.

Thus, for Example 17, an absorbent article 10 was constructed having the general dimensions given in Example 1, and using the materials of Table 1 above. The resulting pad comprised an outer absorbent member 22 made of a 250-gsm densified airlaid web with a density of 0.14 g/cc, a pink impervious polyethylene film as an impervious wicking barrier 24 with adhesive on both sides (not shown), a two-ply central absorbent member 18, and a spunbond topsheet (not shown for simplicity).

The lower layer 52 of the central absorbent member 18 was a pledget of fluff pulp having a basis weight of 656 gsm, a density of 0.14 g/cc, a mass of 1.7 g, and a simple shaping line 54 (a longitudinal embossment) throughout its length to promote upward folding. The lower absorbent 52 was cut to the shape of an ellipse with a major axis of 82 mm (the length) aligned with the longitudinal axis of the article and a minor axis 35 mm wide and comprised essentially 100% Coosa River CR54 pulp, a bleached kraft southern softwood.

The upper layer 50 was 215 mm long and 54 mm wide and was a densified airlaid web with a basis weight of 250 gsm and a density of 0.14 g/cc. The upper layer 50 was further provided with a central slit 98 that is 100 mm long and with two arcuate crease lines 96 formed by crescent-shaped embossments. The arcuate crease lines 98 had an end-to-end linear length of about 8.5 cm and respectively were convex toward the nearby outer longitudinal sides of the article and vertically aligned with the inner sides of the overlap regions 192 in the outer absorbent member 22. The outer absorbent member 22 was provided with a central void 66 having the same dimensions and shape as the upper layer 50 of the central absorbent member 18, except for curved overlap regions 192 in the crotch region 48 which were about 9 cm long, symmetrically placed about the transverse centerline of the article 10, and which diverged inward in the crotch region 48 towards the longitudinal centerline by a maximum of about 10 mm. The outer absorbent member 22 had a length of 225 mm and a maximum width of 75 mm and a minimum width along the transverse centerline of 64 mm. The final article 10 was 238 mm long and 86 mm wide. The wicking barrier 24, the backsheet 14, and the topsheet (not shown) were all cut to the same dogbone shape, 238 mm long and 86 mm wide. The stated dimensions are as seen from a top view.

The article 10 was found to give a body-fitting shape when laterally compressed, exhibiting a desirable W-fold geometry, and with a central portion along the longitudinal of the upper absorbent member 18 exhibiting an inverted V-shape in the crotch region 48. Further, when placed against an anatomically correct model of the torso of an adult female, the deformation of the pad incurred by lateral compression as the article a lowed the front portion of the article to curve upwards toward the body to better fit the pudendal region.

Example 18

Example 18 was generally made according to Example 17 except that no central slit was provided in the upper absorbent member. During lateral compression, the central portion of the absorbent article exhibited more of an inverted-U shape rather than the inverted-V shape of Example 17.

Example 19

Example 19 is a proposed central rising member predisposed to deflect vertically upward when laterally compressed from the longitudinal sides, further provided with attachment means to hold the central rising member in an upwardly deflected position even after the source of lateral compression has been relaxed or removed. Example 19 was made generally according to FIGS. 29A and 29B, which depict a central rising member 30 comprising an absorbent web 194 such as a densified airlaid web, further comprising a central hinge element or scoremark 94 which predisposes the absorbent web 194 to flex upward when inwardly laterally compressed from the longitudinal sides. Attachment means, such as a mechanical attachment means exemplified by a patch of hook material 196 and a patch of loop material 198, for a classic hook-and-loop attachment system, are disposed on opposing sides of the hinge or scoremark 94 of the central rising member 30 on the garment-side surface thereof, such that the opposing attachment means 196, 198 can engage upon inwardly lateral compression and hold the central rising member 30 in a deformed position, as shown in FIG. 29B, even when lateral compressive forces are removed or relaxed.

The attachment means 196, 198 are for holding the two sides of the central rising member 30 together after making contact as the two longitudinal sides are brought closer together during lateral compression. The attachment means preferably are mechanical hook-and-loop systems, exemplified by VELCRO® materials. In one embodiment, the absorbent web 194 is wrapped by or joined on the garment-side surface to a layer of loop material such as a spunbond nonwoven web (not shown), in which case the wrapping or layer of loop material would serve as the patch of loop material 198. An exemplary loop material is that of U.S. Pat. No. 5,773,120, issued Jun. 30, 1998.

Figure 29A:
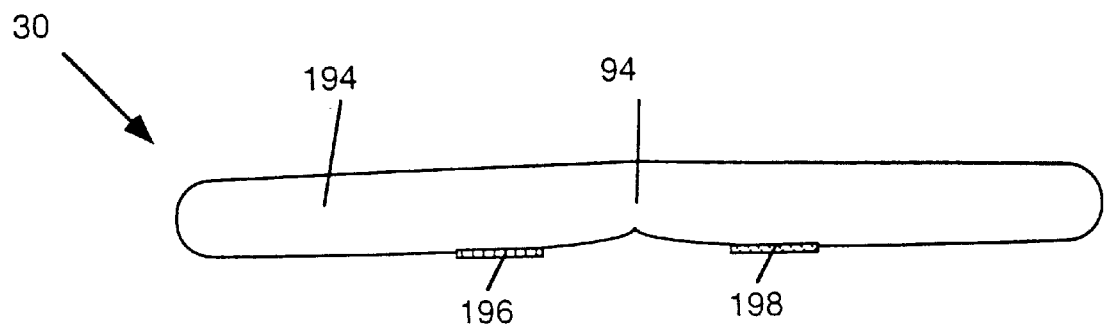
FIGS. 29A and 29B show a central rising member predisposed for upward deflection during lateral compression with fastening means to hold the central rising member in place, with two states being depicted before and after self-attachment has occurred.
Figure 29B:
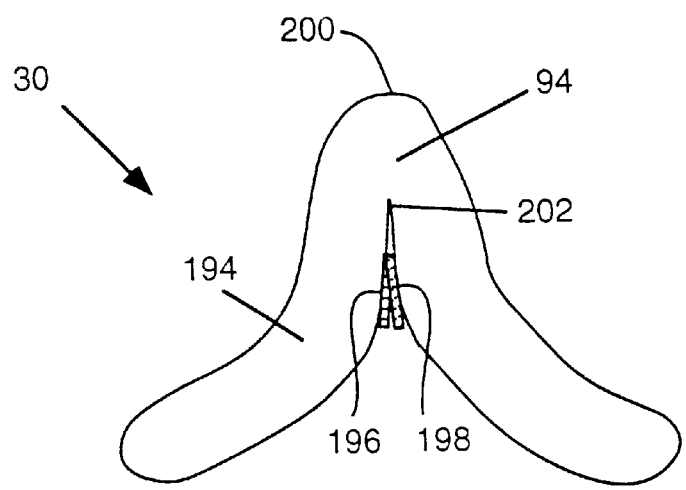

In its deformed state held in place by attachment means 196, 198, as shown in FIG. 29B, the central rising member 30 has a central ridge 200 which is the most elevated portion, and a lower central cusp 202. The central rising member 30 (or any other central rising member described herein) can have a Vertical Deformation of about 3 mm or greater, more specifically about 5 mm or greater, more specifically still about 7 mm or greater, and most specifically from about 10 mm to about 25 mm.

The absorbent web 194 can be an densified airlaid web, paperboard, a foam, a thermoplastic deformation element, and the like.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article having two longitudinal sides and a target zone, the absorbent article comprising:

a) a backsheet;
b) a topsheet attached to the backsheet; and
c) an absorbent core positioned between the topsheet and the backsheet, the absorbent core comprising:
   an outer absorbent member including a body-side surface,
   a central absorbent member having a width in the target zone, the central absorbent member operatively associated with a central rising member, and
   a wicking barrier disposed between the outer absorbent member and the central absorbent member, the wicking barrier at least partially disposed on the body-side surface of the outer absorbent member,
   the outer absorbent member having a width in the target zone greater than the width of the central absorbent member in the target zone, whereby lateral compression of the absorbent core from the longitudinal sides causes the central rising member to deflect the central absorbent member away from the backsheet,
   wherein at least a portion of the wicking barrier underlies at least a portion of the central absorbent member.

2. The absorbent article of claim 1, wherein the central absorbent member overlaps a portion of the outer absorbent member.

3. The absorbent article of claim 2, wherein the central absorbent member overlaps the outer absorbent member in the target zone.

4. The absorbent article of claim 1, wherein the central absorbent member is a folded web.

5. The absorbent article of claim 1, wherein the central rising member is disposed below the wicking barrier.

6. The absorbent article of claim 1, wherein the central rising member is absorbent and comprises a fibrous mat.

7. The absorbent article of claim 1, wherein the central rising member comprises a central inflatable member.

8. The absorbent article of claim 1, wherein the outer absorbent member comprises two spaced apart longitudinal strips of absorbent material having inner walls.

9. The absorbent article of claim 1, wherein the central absorbent member further comprises a stability layer and an expansion layer heterogeneously attached to said stability layer at a discrete number of attachment regions, wherein, upon wetting, said expansion layer expands laterally in at least one direction more than said stability layer.

10. The absorbent article of claim 1, wherein the outer absorbent member has a central void extending partially through the outer absorbent member, a portion of the central absorbent member residing within the central void.

11. The absorbent article of claim 1, wherein the outer absorbent member has a central void extending completely through the outer absorbent member, a portion of the central absorbent member residing within the central void.

12. The absorbent article of claim 1, wherein the central rising member comprises a resilient material folded to have a cross-section in the shape of a rotated letter "C".

13. The absorbent article of claim 1, wherein the central rising member comprises a section of a resilient material in the form of a flattened tube.

14. The absorbent article of claim 1, wherein the central rising member comprises a hinge element.

15. An absorbent article having a target zone, a longitudinal direction, a transverse direction, and a vertical direction substantially normal to both the longitudinal and transverse directions, the absorbent article comprising:

a) an absorbent core having a central absorbent member and an outer shaping member, the outer shaping member defining a central void for receiving at least a portion of the central absorbent member, whereby an interface is defined between the central absorbent member and the outer shaping member, the interface spanning a vertical distance,
b) a wicking barrier disposed along the interface between the central absorbent member and the outer absorbent member; and
c) at least one of a central rising member and a central inflatable member disposed beneath the central absorbent member.

16. The absorbent article of claim 15, wherein the wicking barrier further comprises a horizontal component spanning a horizontal distance on the absorbent core.

17. The absorbent article of claim 15, wherein the wicking barrier is liquid impervious.

18. The absorbent article of claim 15, wherein the wicking barrier is liquid pervious.

19. The absorbent article of claim 15, wherein the wicking barrier has liquid pervious and liquid impervious regions.

20. The absorbent article of claim 15, wherein the wicking barrier is a polymeric film.

21. The absorbent article of claim 20, wherein the wicking barrier is a polymeric film comprising apertures beneath a region covered by the central absorbent member.

22. An absorbent article comprising a topsheet, a backsheet joined to the topsheet, an absorbent core disposed between the backsheet and the topsheet, the absorbent core comprising a central absorbent member operatively associated with a central rising member, the central rising member having longitudinal sides and a longitudinally central hinge dividing the central rising member into a first portion and second portion, the article further comprising attachment means in cooperative relationship with the central rising member, wherein application of inwardly lateral compressive force to the longitudinal sides of the central rising member causes the central rising member to deflect upward along the longitudinally central hinge, and wherein the attachment means holds the central rising member in an upwardly deflected state when the inwardly lateral compressive force is relaxed.

23. The absorbent article of claim 22, wherein the central rising member further comprises a garment-side surface, wherein the attachment means comprise a first attachment section on the garment-side surface of the first portion of the central rising member and a second attachment section on the garment-side surface of the second portion of the central rising member, wherein the first attachment section connects to the second attachment section when the garment-side surface of the first portion of the central rising member is brought into contacting relationship with the garment-side surface of the second portion of the central rising member.

24. The absorbent article of claim 22, wherein the attachment means comprises a mechanical attachment means disposed on the garment-side surface of the central rising member.

25. The absorbent article of claim 22, wherein the attachment means comprises hook-and-loop fasteners.

* * * * *

UNITED STATES PATENT AND TRADEMARK OFFICE
CERTIFICATE OF CORRECTION

PATENT NO.      : 6,677,498 B2
DATED           : January 13, 2004
INVENTOR(S)     : Fung-jou Chen et al.

It is certified that error appears in the above-identified patent and that said Letters Patent is hereby corrected as shown below:

Title page,
Item [63], Related U.S. Application Data, "Pat. No. 6,492,547." should read -- Pat. No. 6,492,574. --

Signed and Sealed this

Twenty-third Day of March, 2004

JON W. DUDAS
*Acting Director of the United States Patent and Trademark Office*